(12) United States Patent
Mazur et al.

(10) Patent No.: US 11,319,584 B2
(45) Date of Patent: *May 3, 2022

(54) POLYMERASE COMPOSITIONS AND METHODS OF MAKING AND USING SAME

(71) Applicant: LIFE TECHNOLOGIES CORPORATION, Carlsbad, CA (US)

(72) Inventors: Daniel Mazur, San Diego, CA (US); Eileen Tozer, San Diego, CA (US); Sihong Chen, Vista, CA (US); Peter Vander Horn, Encinitas, CA (US); Tommie Lincecum, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/947,742

(22) Filed: Aug. 14, 2020

(65) Prior Publication Data

US 2020/0385786 A1 Dec. 10, 2020

Related U.S. Application Data

(60) Continuation of application No. 15/961,206, filed on Apr. 24, 2018, now Pat. No. 10,745,747, which is a division of application No. 14/970,818, filed on Dec. 16, 2015, now Pat. No. 9,976,178.

(60) Provisional application No. 62/092,756, filed on Dec. 16, 2014.

(51) Int. Cl.
  *C12N 9/12* (2006.01)
  *C12Q 1/686* (2018.01)
  *C12Q 1/6869* (2018.01)

(52) U.S. Cl.
  CPC ........... *C12Q 1/686* (2013.01); *C12N 9/1252* (2013.01); *C12Q 1/6869* (2013.01); *C12Q 2521/101* (2013.01); *C12Y 207/07007* (2013.01)

(58) Field of Classification Search
  None
  See application file for complete search history.

(56) References Cited

FOREIGN PATENT DOCUMENTS

| CN | 103266103 A | 8/2013 |
|---|---|---|
| WO | WO-0222869 A2 | 3/2002 |
| WO | WO-2010062777 A2 | 6/2010 |
| WO | WO-2010062779 | 6/2010 |
| WO | WO-2013/023176 | 2/2013 |
| WO | WO-2014062848 | 4/2014 |

OTHER PUBLICATIONS

EP20186874.2, Extended European Search Report, dated May 11, 2021, 13 pages.
EP20186874.2, Partial European Search Report, dated Feb. 23, 2021, 14 pages.
Ngo, et al., "Computational Complexity, Protein Structure Prediction, and the Levinthal Paradox", *The Protein Folding Problem And Tertiary Structure Prediction*, Birkhauser, Boston, 1994, pp. 492-495.
PCT/US2015/065977, , "International Search Report and Written Opinion", dated Jun. 13, 2016.
Database Registry [Online], Chemical Abstracts Service, Columbus, Ohio, US; Sep. 20, 2013 (Sep. 20, 2013), "DNA (Thermus aquaticus Taq DNA polymerase gene)", XP002784348, Database accession No. 1452903-44-4.

*Primary Examiner* — Richard G Hutson
(74) *Attorney, Agent, or Firm* — Klarquist Sparkman, LLP

(57) ABSTRACT

The present disclosure provides compositions, methods, kits, systems and apparatus that are useful for nucleic acid polymerization. In particular, modified polymerases and biologically active fragments thereof, such as modified Taq polymerases, are provided that allow for improved nucleic acid amplification. In some aspects, the disclosure provides modified polymerases having improved thermostability, accuracy, processivity and/or read length as compared to a referenceTaq polymerase. In some aspects, the disclosure relates to modified polymerases or biologically active fragments thereof, useful for amplification methods, and in practically illustrative embodiments, emulsion PCR.

16 Claims, 15 Drawing Sheets

Specification includes a Sequence Listing.

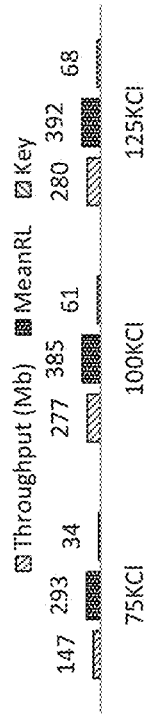
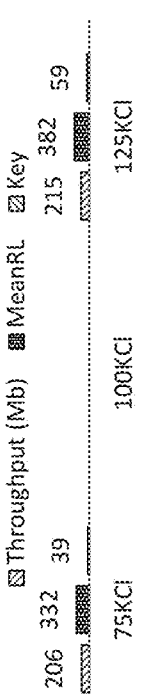
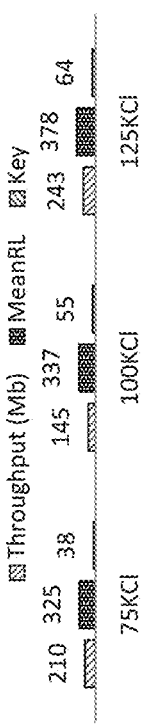
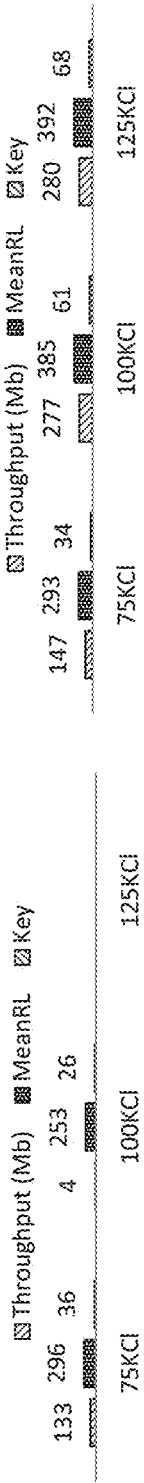
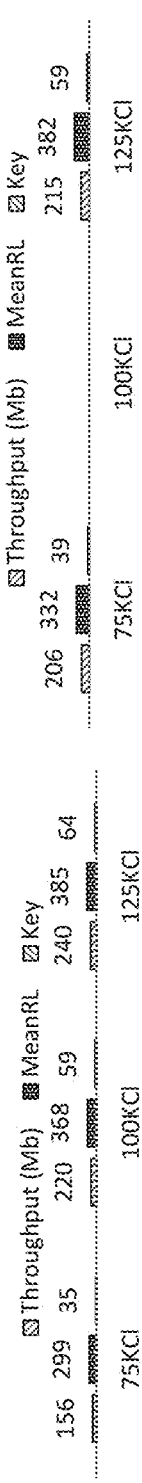
FIG. 1A
FIG. 1B
FIG. 1C
FIG. 1D
FIG. 1E

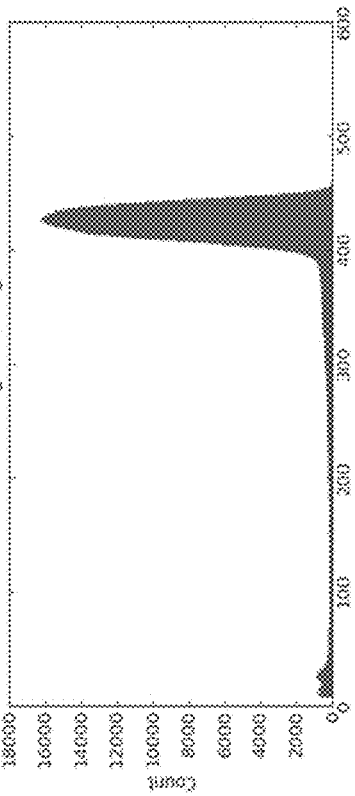
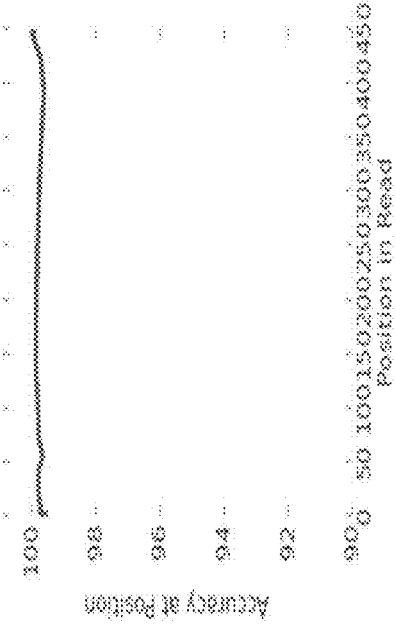
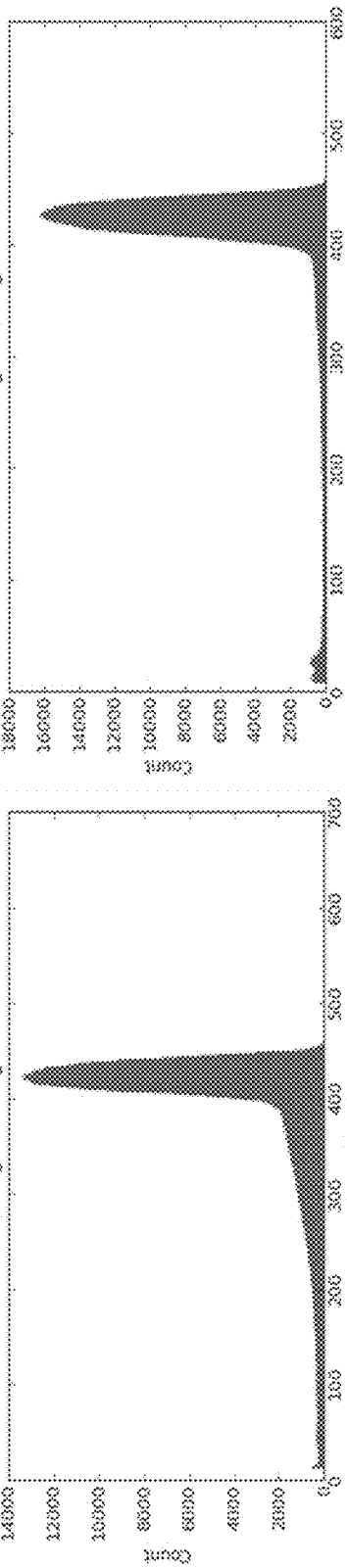
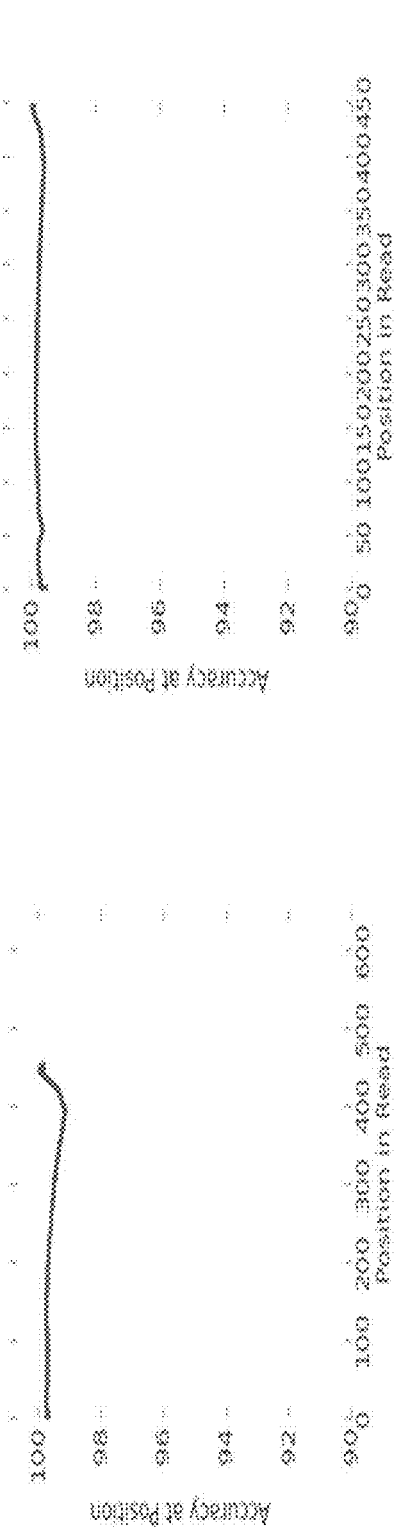
FIG. 2A 1
FIG. 2A 2
FIG. 2B 1
FIG. 2B 2

| | KCl Conc | AQ20 total base count | AQ17 mean (>20bp) | AQ20 mean (>20bp) | 100Q17/50Q 17% | Uniformity of amplicon coverage% | Amplicons reading end-to-end% | Amplicons with no strand bias% |
|---|---|---|---|---|---|---|---|---|
| SEQ ID #34 | 130 | 2180913838 | 154 | 139 | 83.84 | 92.82 | 16 | 89 |
| E713W | 150 | 2133155068 | 161 | 147 | 86.36 | 91.05 | 21 | 90 |
| L490Q | 75 | 2136294606 | 149 | 132 | 82.09 | 94.8 | 14 | 88 |
| L763F | 100 | 1850574878 | 156 | 141 | 84.35 | 94.74 | 20 | 90 |
| G418C | 100 | 2254263879 | 155 | 139 | 83.59 | 94.75 | 20 | 89 |
| E805I | 125 | 1790086930 | 164 | 151 | 86.9 | 93.08 | 28 | 91 |
| E267I | 100 | 1359059761 | 139 | 122 | 78.16 | 94.53 | 6 | 87 |
| E397V | 125 | 2412128331 | 167 | 155 | 88.28 | 93.57 | 32 | 90 |
| E794C | 125 | 2394584550 | 164 | 151 | 87.48 | 93.98 | 28 | 92 |
| R593G | 125 | 3343746482 | 168 | 156 | 88.54 | 93.38 | 33 | 92 |

FIG. 3A

| | KCl Conc | AQ20 total base count | Target bases with no strand bias% | Amplicons with at least 20 reads% | Target base coverage at 20x | SSE | Uniformity of base coverage | Amplicons with 1 read | Target base coverage at 1x |
|---|---|---|---|---|---|---|---|---|---|
| SEQ ID #34 | 130 | 2180913838 | 74 | 84 | 76 | 0.44 | 91.26 | 98.65 | 97.67 |
| E713W | 150 | 2133155068 | 78 | 83 | 76 | 0.36 | 89.52 | 98.2 | 97.08 |
| L490Q | 75 | 2136294606 | 73 | 83 | 73 | 0.62 | 93.23 | 99.48 | 98.92 |
| L763F | 100 | 1850574878 | 76 | 84 | 76 | 0.53 | 93.41 | 99.25 | 98.67 |
| G418C | 100 | 2254263879 | 75 | 88 | 81 | 0.52 | 93.26 | 97.67 | 98.6 |
| E805I | 125 | 1790086930 | 81 | 82 | 75 | 0.45 | 91.8 | 98.27 | 97.43 |
| E267I | 100 | 1359059761 | 69 | 76 | 61 | 0.52 | 92.56 | 99.18 | 98.37 |
| E397V | 125 | 2412128331 | 80 | 87 | 82 | 0.38 | 92.27 | 98.88 | 98.11 |
| E794C | 125 | 2394584550 | 80 | 88 | 83 | 0.39 | 92.7 | 98.91 | 98.18 |
| R593G | 125 | 3343746482 | 82 | 91 | 88 | 0.44 | 92.37 | 99 | 98.35 |

FIG. 3B

TEVO ePCR Enzyme Candidate Improves Coverage for High GC Species Rhodopseudomonas palustris

| Taq Mutant | Read length | Throughput (bases) | Coverage Uniformity | Gaps in Coverage |
|---|---|---|---|---|
| Taqlr1 (1x) SOP | 307 | 132M | 96.62% | >99 |
| Taqli1 (2x) | 292 | 152M | 96.52% | >99 |
| Hit #1 (96°C) | 362 | 240M | 99.75% | 5 |
| Hit #1 (97°C) | 367 | 205M | 99.90% | 4 |

FIG. 4

| Polymerase | aq20bases | loading density | peak signal | aq20 mean | raw Accuracy | snr | SSE | End to End |
|---|---|---|---|---|---|---|---|---|
| SEQ ID NO: 34 | 1,016,373,627 | 0.78 | 54 | 177 | 99.4 | 17.12 | 0.121% | 48.5 |
| SEQ ID NO: 34 | 1,036,034,654 | 0.79 | 58 | 180 | 99.4 | 16.84 | 0.118% | 57 |
| SEQ ID NO: 34 | 837,920,103 | 0.78 | 57 | 152 | 99.3 | 16.61 | 0.159% | 2.2 |
| 397V-745T-763F | 872,453,475 | 0.72 | 57 | 180 | 99.4 | 17.37 | 0.131% | 51.6 |
| 397V-745T-763F | 1,078,943,334 | 0.8 | 58 | 181 | 99.5 | 19.38 | 0.099% | 56.37 |
| 763F-805I | 987,979,596 | 0.76 | 57 | 186 | 99.5 | 18.11 | 0.111% | 70.1 |
| 763F-805I | 853,315,243 | 0.76 | 62 | 174 | 99.4 | 17.53 | 0.145% | 33.15 |
| 763F-805I | 1,089,487,907 | 0.79 | 55 | 182 | 99.5 | 17.15 | 0.120% | 56.27 |
| 397V | 1,112,761,078 | 0.75 | 62 | 193 | 99.6 | 21.02 | 0.109% | 79.5 |
| 397V | 1,045,037,429 | 0.71 | 62 | 194 | 99.6 | 20.3 | 0.115% | 80.3 |

FIG. 6

POLYMERASE COMPOSITIONS AND METHODS OF MAKING AND USING SAME

CROSS-REFERENCE TO RELATED APPLICATIONS

This application is a Continuation of U.S. application Ser. No. 15/961,206, filed Apr. 24, 2018, now allowed, which is incorporated herein by reference in its entirety and which is a Division of U.S. application Ser. No. 14/970,818, filed Dec. 16, 2015, now U.S. Pat. No. 9,976,178, issued May 22, 2018, which claims benefit of U.S. Provisional Application Ser. No. 62/092,756, filed Dec. 16, 2014, the disclosure of each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 11, 2015, is named LT00925_SL.txt and is 247,676 bytes in size.

FIELD OF THE INVENTION

The present invention generally relates to mutant polymerases with improved properties, for example mutant Taq polymerases, as well as nucleic acids encoding the same, and methods and kits using the same.

BACKGROUND

The ability of enzymes to catalyze biological reactions is fundamental to life. A range of biological applications use enzymes to synthesize various biomolecules in vitro. One particularly useful class of enzymes is the polymerases, which can catalyze the polymerization of biomolecules (e.g., nucleotides or amino acids) into biopolymers (e.g., nucleic acids or peptides). For example, polymerases that can polymerize nucleotides into nucleic acids, particularly in a template-dependent fashion, are useful in recombinant DNA technology and nucleic acid detection and nucleic acid sequencing applications. Many nucleic acid sequencing methods monitor nucleotide incorporations during in vitro template-dependent nucleic acid synthesis catalyzed by a polymerase. Single Molecule Sequencing (SMS) and Paired-End Sequencing (PES) typically include a polymerase for template-dependent nucleic acid synthesis. Polymerases are also useful for the generation of nucleic acid libraries, such as nucleic acid libraries created during emulsion PCR or bridge PCR. Nucleic acid libraries created using such polymerases can be used in a variety of downstream processes, such as genotyping, nucleotide polymorphism (SNP) analysis, copy number variation analysis, epigenetic analysis, gene expression analysis, hybridization arrays, analysis of gene mutations including but not limited to detection, prognosis and/or diagnosis of disease states, detection and analysis of rare or low frequency allele mutations, and nucleic acid sequencing including but not limited to de novo sequencing or targeted resequencing.

A desirable quality of a polymerase useful for nucleic acid amplification, synthesis and/or detection is improved incorporation of nucleotides as compared to a reference polymerase. Improved nucleotide incorporation can make processes such as nucleic acid library preparation and/or DNA sequencing more cost effective by reducing the number of nucleic acid templates necessary to sequence a desired target molecule. In another aspect, improved nucleotide incorporation as compared to a reference polymerase can also reduce the number of sequencing reads required to determine the sequence of the desired target molecule.

Additionally, improved nucleotide incorporation (as compared to a reference polymerase) can also improve signal uniformity, leading to increased accuracy in base determination of the desired target molecule. In yet another aspect, improved nucleotide incorporation by a modified polymerase as compared to a reference polymerase can increase the read length of the desired target molecule and thus reduces the likelihood of the modified polymerase stalling or dissociating from the desired target molecule. In yet another aspect, a modified polymerase having improved templating or clonal amplification efficiency as compared to a reference polymerase and thus can improve downstream sequencing of a target molecule that is customarily considered a "difficult" target molecule, such as a target molecule with high GC or AT content. As such, one aspect of invention is to provide a method, system, apparatus, and compositions of matter that improve GC and AT bias in nucleic acid amplification using a modified polymerase having a reduced GC or AT content bias.

Another desirable quality in an enzyme used in nucleic acid library preparation or DNA sequencing is thermal stability. DNA polymerases exhibiting thermal stability have revolutionized many aspects of molecular biology and clinical diagnostics since the development of the polymerase chain reaction (PCR), which uses cycles of thermal denaturation, primer annealing, and enzymatic primer extension to amplify DNA templates. A prototype thermostable DNA polymerase used in the initial PCR experiments was Taq DNA polymerase, originally isolated from the thermophilic eubacterium *Thermus aquaticus*.

There are three major families of DNA polymerases, termed families A, B and C. The classification of a polymerase into one of these three families is based on structural similarity of a given polymerase to *E. coli*; DNA polymerase I (Family A), II (Family B) or III (family C). As examples, Family A DNA polymerases include, but are not limited to Klenow DNA polymerase, *Thermus aquaticus* DNA polymerase I (Taq polymerase) and bacteriophage T7 DNA polymerase; Family B DNA polymerases, formerly known as α-family polymerases (Braithwaite and Ito, 1991, Nuc. Acids Res. 19:405), include, but are not limited to human α, δ and ε DNA polymerases, T4, RB69 and φ29 bacteriophage DNA polymerases, and *Pyrococcus furiosus* DNA polymerase (Pfu polymerase); and family C DNA polymerases include, but are not limited to *Bacillus subtilis* DNA polymerase III and *E. coli* DNA polymerase III and subunits (listed as products of the dnaE and dnaQ genes, respectively, by Braithwaite and Ito. 1993, Nucleic Acids Res. 21: 787). An alignment of DNA polymerase protein sequences of each family across a broad spectrum of archaeal, bacterial, viral and eukaryotic organisms is presented in Braithwaite and Ito (1993, supra), which is incorporated herein by reference in its entirety.

When performing polymerase-dependent nucleic acid synthesis or amplification, it can be useful to modify the polymerase (for example via mutation or chemical modification) so as to alter its catalytic properties. In some instances, it can be useful to modify the polymerase to enhance its catalytic properties. In some embodiments, it can be useful to enhance a polymerase's catalytic properties via site-directed amino acid substitution or deletion. In some embodiments, it can be useful to enhance a polymerase's catalytic properties via site-saturation mutagenesis of one, a plurality, or each, amino acid of the polymerase. In some embodiments, modification of a polymerase may be performed to enhance catalytic properties of the modified polymerase such as read length, accuracy, and/or processivity.

Polymerase performance in various biological assays involving nucleic acid synthesis or detection can be limited by the behavior of the polymerase towards nucleotide substrates, salt concentrations, or thermostable conditions. For example, analysis of polymerase activity can be complicated by undesirable behavior such as the tendency of a given polymerase to dissociate from the template; to bind and/or incorporate the incorrect, e.g., non Watson-Crick base-paired, nucleotide; or to release the correct, e.g., Watson-Crick based paired, nucleotide without incorporation. Additionally, analysis of polymerase activity can be complicated by undesirable behavior of a target molecule from fully denaturing, such as in high AT and GC rich regions or premature attenuation of the target molecule. As demonstrated herein, desirable polymerase properties for improved nucleic acid amplification can be achieved via suitable selection, engineering and/or modification of a polymerase of choice. For example, such modification can be performed to favorably alter the polymerase's affinity of binding to template, processivity, accuracy of nucleotide incorporation, strand bias, and coverage. Such alterations within the polymerase can also increase the amount of sequence information and/or quality of sequencing information obtained directly, or downstream, from the improved amplification workflow utilizing such a modified polymerase.

There remains a need in the art for improved polymerase compositions (and related methods, systems, apparatuses, and kits) exhibiting altered properties, e.g., increased processivity, increased read length (including error-free read length), increased accuracy and/or affinity for DNA template, increased coverage, decreased strand bias and/or decreased systematic error. Such polymerase compositions (and related methods, systems, apparatuses, and kits) can be useful in a wide variety of assays involving polymerase-dependent nucleic acid synthesis, including nucleic acid sequencing and/or the production of nucleic acid libraries, such as nucleic acid libraries prepared by bridge PCR or clonal amplification.

SUMMARY OF THE INVENTION

The present invention in certain embodiments provides a composition that includes an isolated polypeptide, as well as isolated nucleic acids and vectors encoding the same, having at least 50, 75, 100, 150, 175, 200, 250, 300, 350, 400, 500, 600, 700, or 800 contiguous amino acid residues having at least 70%, 75%, 80%, 85%, 90%, 95%, 96%, 97%, 98%, and 99%, identity to SEQ ID NO: 1 or SEQ ID NO: 34, or a biologically active fragment thereof, wherein the polypeptide exhibits polymerase activity. In exemplary embodiments, the isolated polypeptide exhibits an improvement relative to a reference polymerase of SEQ ID NO:1 and/or SEQ ID NO:34, in one or more properties selected from thermostability and/or a sequencing property selected from read length, accuracy, strand bias, systematic error, and total sequencing throughput. In certain embodiments, the isolated polypeptide includes one or more amino acid substitutions selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A. The sequencing properties in certain embodiments, are determined by using the isolated polypeptide in an emulsion PCR template amplification reaction, in certain illustrative embodiments in the presence of 125 mM KCl or 125 mM NaCl, during sample preparation of a nucleic acid sequencing reaction. In certain embodiments, the sequencing property is analyzed using a next-generation (i.e. massively parallel, high throughput) sequencing workflow, such as an Ion Torrent (Life Technologies, Carlsbad, Calif.) sequencing workflow, as exemplified herein. In certain aspects, the isolated polypeptide as well as a modified polymerase used in a method embodiment provided herein, has improved thermostability at 95° C., 96° C., or 97° C. for 2 minutes, 4 minutes, and in illustrative examples 6 minutes as compared to the thermostability of SEQ ID NO: 1 at 95° C. for the same time period and temperature. In illustrative examples, the thermostability can be tested by incubating the on-test and control polymerase under identical conditions that include elevated temperatures, for example 95° C., 96° C., or 97° C. for 2 minutes, 4 minutes, and in illustrative examples 6 minutes in an incubation buffer that includes, for example 15 mM Tris pH 7.5, 100 mM KCl, 30% Trahalose, 0.1% NP40, and 50 mM polymerase enzyme. After incubation at elevated temperature, the solutions can optionally be placed on ice and then transferred to an enzyme reaction mixture that includes 15 mM Tris pH 7.5, 100 mM KCl, 8 mM MgCl$_2$, 150 nm Oligo 221 and 5 nM of polymerase reaction mixture from the heat-treatment step (10 ul). Oligo 221 is a hairpin oligo with a fluorescent dye attached (TTTTTTTGCAGGTGACAGGTTTTTCCTGT-CACCXGC (SEQ ID NO: 50), where X is a fluorescein-dT residue). Upon addition of dATP, oligo 221 is extended, resulting in release of the florescence. Accordingly, as a non-limited example, the thermostability can be tested using the method provided in Example 10 as outlined in FIG. 14) herein. In certain illustrative embodiments, the isolated polypeptide has improved thermostability at 95° C. for 6 minutes as compared to the thermostability of SEQ ID NO: 1 at 95° C. for 6 minutes. In certain illustrative embodiments of these aspects, the thermostable isolated polypeptide, or the biologically active fragment thereof, includes G418C or E397V. In yet further embodiments, in addition to a G418C or in particular aspects, an E397V mutation, the isolated peptide further includes one or more amino acid substitutions selected from the group consisting of E745T, L763F and E805I, wherein the numbering is relative to SEQ ID NO: 1. In certain aspects, the composition includes a reagent for a hot start activation mechanism, such as an oligonucleotide and/or an aptamer. In other aspects, the isolated polypeptide is chemically modified to provide a hot start mechanism.

In one embodiment of the invention one or more properties exhibited by the isolated polypeptide or the biologically active fragment thereof of the composition include at least two, three, four, five, six, or all sequencing workflow properties selected from increased AQ20 mean read length reads, reduced strand bias, increased base coverage, increased accuracy, increased sequencing throughput (Mb) and increased uniformity of coverage, relative to a reference polymerase having a sequence of SEQ ID NO: 34 and/or SEQ ID NO: 1. In some embodiments the isolated polypeptide or biologically active fragment thereof, where one mutation is E397V, another mutation is P6N, E745T and/or L763F. In another embodiment, that may or may not include E397V, the mutations include L763F and/or E805I, P6N and/or E295F, or E745T and/or E794C.

In a further embodiment of the invention the one or more properties of the composition are exhibited when or analyzed or tested by performing an emulsion PCR template amplification reaction on a library constructed from a template having a GC content of 65%. In certain embodiments the reference polymerase is SEQ ID NO:34, and in certain particularly illustrative embodiments, the reference polymerase is SEQ ID NO:1.

In one embodiment of the inventive composition, the isolated polypeptide or biologically active fragment thereof includes a mutation selected from A77E, A97V, K240I, L287T, or K292C relative to a reference polymerase having a sequence of SEQ ID NO:1 and in exemplary aspects of this embodiment, the one or more properties include a sequencing property analyzed using a high throughput nucleic acid sequencing reaction where the polypeptide or biologically active fragment thereof is used to perform an emulsion PCR template amplification reaction on a library constructed from a template with a GC content of 65%.

In another embodiment the isolated polypeptide of the composition includes SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. It will be understood that in illustrative embodiments of the present invention, including composition and method embodiments that include an isolated polypeptide or modified polymerase provided herein, the isolated polypeptide or modified polymerase can be analyzed to determine whether it possesses certain properties, activities, or characteristics using an emulsion PCR reaction to amplify templates as part of a sequencing workflow, for example to amplify templates on a solid support, and in some illustrative embodiments, to clonally amplify templates on a solid support. The nucleic acid sequence of at least a portion of the amplified templates is then determined. This sequence determination in illustrative embodiments is performed using a high throuput sequencing platform such as Ion Torren PGM, as exemplified herein. The results of this sequence determination are compared to results of similar experiments performed using a reference polymerase, such as Taq polymerase (SEQ ID NO:1) or the modified Taq polymerase of SEQ ID NO:34, for an emulsion PCR template amplification step in a high throughput sequencing reaction. In one aspect the test for an isolated polypeptide or a mutant polymerase includes amplifying a library of nucleic acid molecules using emulsion PCR for both an on-test and a reference polymerase, onto a nucleic acid capture support such as Ion Sphere™ particles. The amplified nucleic acid molecules in this embodiment, can then be loaded into a PGM™ 314 sequencing chip, which can then be loaded into an Ion Torrent PGM™ Sequencing system and sequenced. Sequencing results for the on-test and the reference polymerase can then be compared.

In another embodiment, provided herein is a method (and related kits, apparatuses, systems and compositions) for amplifying a nucleic acid, that includes contacting the nucleic acid with a modified polymerase, or a biologically active fragment thereof, under suitable conditions for amplifying the nucleic acid, and amplifying the nucleic acid, wherein the modified polymerase or the biologically active fragment thereof, has at least 70, 75, 80, 85, 90, 95, 96, 97, 98, or 99% sequence identity to SEQ ID NO:1 or SEQ ID NO:34, exhibits polymerase activity and exhibits an improvement relative to a reference polymerase of SEQ ID NO:1 and/or SEQ ID NO:34, in one or more properties selected from thermostability and/or a sequencing property selected from read length, accuracy, strand bias, systematic error, and total sequencing throughput, and wherein the modified polymerase includes one or more amino acid substitutions selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A. In certain particular embodiments the sequencing property is analyzed using an emulsion PCR template amplification reaction, which in especially illustrative embodiments includes 125 mM KCl or 125 mM NaCl, during sample preparation of a nucleic acid sequencing reaction. In certain embodiments, the sequencing reaction under which a sequencing property of the modified polymerase is analyzed is part of a next-generation (i.e. massively parallel, high throughput) sequencing workflow (e.g., a workflow used in an Ion Torrent System, Illumina HiSeq or True Seq or X-10 system). In some embodiments, the sequencing workflow uses an ISFET based sensor. In certain embodiments, the sequencing property is analyzed using an Ion Torrent (Life Technologies, Carlsbad, Calif.) sequencing workflow and system, as exemplified herein. In certain aspects, the modified polymerase used in the method has improved thermostability at 95° C. for 6 minutes as compared to the thermostability of SEQ ID NO: 1 at 95° C. for 6 minutes. In certain illustrative embodiments of these aspects, the thermostable modified polymerase, or the biologically active fragment thereof, used in the method includes G418C or E397V. In yet further embodiments, in addition to a G418C or in particular aspects, an E397V mutation, the isolated peptide further includes one or more amino acid substitutions selected from the group consisting of E745T, L763F and E805I, wherein the numbering is relative to SEQ ID NO: 1. In certain aspects, the method includes a hot start, as is known in the PCR arts. In these methods of the invention that include a hot start, compositions in which the method is performed can include a reagent such as an oligonucleotide and/or an aptamer that is used for the hot start or the modified polymerase can be chemically modified to provide a hot start mechanism.

In one embodiment of the invention one or more properties exhibited by the modified polymerase or the biologically active fragment thereof used in the method, include at least two, three, four, five, six, or all sequencing workflow properties selected from increased AQ20 mean read length reads, reduced strand bias, increased base coverage, increased accuracy, increased sequencing throughput (Mb) and increased uniformity of coverage, relative to a reference polymerase having a sequence of SEQ ID NO: 34 and/or SEQ ID NO: 1. In some embodiments the modified polymerase or biologically active fragment thereof, where one mutation is E397V, another mutation is P6N, E745T and/or L763F. In another embodiment, that may or may not include E397V, the mutations include L763F and/or E805I, P6N and/or E295F, or E745T and/or E794C.

In a further embodiment of the invention the one or more properties of the mutant polymerase used in the method are exhibited when, or can be determined by performing an emulsion PCR template amplification reaction on a library constructed from a template having a GC content of 65%. For the sake of clarity, such steps are not part of the inventive method, but rather are for determining whether a modified polymerase meets the criteria for a modified polymerase that is used in the method. In certain embodiments the reference polymerase used for the polymerase criteria testing is SEQ ID NO:34, and in certain particularly illustrative embodiments, the reference polymerase is SEQ ID NO:1.

In one embodiment of the inventive method, the modified polymerase or biologically active fragment thereof used in the method includes a mutation selected from A77E, A97V, K240I, L287T, or K292C relative to a reference polymerase having a sequence of SEQ ID NO:1. In exemplary aspects of this embodiment, the one or more properties of the modified polypeptide used in the method include a sequencing property analyzed using a next-generation (i.e. massively parallel, high throughput) nucleic acid sequencing reaction where the modified polymerase or biologically active fragment thereof is tested for such properties using an emulsion PCR template amplification reaction on a library constructed from a template with a GC content of 65%.

In certain embodiments, the polymerase used in the method comprises 50, 75, 100, 150, 175, 200, 250, 300, 350, 400, 500, 600, 700, or 800 contiguous amino acid residues of SEQ ID NO:1 or SEQ ID NO:34 and has at least 70%, 75%, 80%, 85%, 90%, 95%, 96%, 97%, 98%, or 99%, identity to SEQ ID NO: 1 or SEQ ID NO: 34, or a biologically active fragment thereof, In certain embodiments the modified polymerase used in the method includes SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments of the method for amplifying a nucleic acid, suitable conditions for performing the amplification are suitable conditions for performing a polymerase chain reaction, an isothermal amplification reaction, a recombinase polymerase amplification reaction, a proximity ligation amplification, a rolling circle amplification, a strand displacement amplification, or an emulsion polymerase chain reaction. Accordingly, in these embodiments, the method for amplifying the nucleic acid is one of the above listed methods for amplification.

In yet another embodiment, the method for amplifying a nucleic acid, includes clonally amplifying the nucleic acid in solution or on a solid support. In a further embodiment of the method includes determining the nucleic acid sequence of at least a portion of the nucleic acid. In some embodiments, the nucleic acid sequence can be determined using any next-generation (i.e. massively parallel, high throughput) sequencing platform (e.g., Ion Torrent Systems, Illumina HiSeq or True Seq or X-10 systems). In some embodiments, the nucleic acid sequence can be determined using any ISFET based sequencing system.

In a further embodiment of the method the nucleic acid comprises at least 65% GC content or at least 65% AT content.

Another embodiment of the invention is a method for performing a nucleic acid polymerization reaction including contacting a modified polymerase, or a biologically active fragment thereof, under suitable conditions for a polymerization reaction, with a nucleic acid template in the presence of one or more nucleotide triphosphates, wherein the modified polymerase or the biologically active fragment thereof, has at least 70, 75, 80, 85, 90, 95, 96, 97, 98, or 99% sequence identity to SEQ ID NO:1 or SEQ ID NO:34, exhibits polymerase activity and exhibits an improvement relative to a reference polymerase of SEQ ID NO:1 and/or SEQ ID NO:34, in one or more properties selected from thermostability and/or a sequencing property selected from read length, accuracy, strand bias, systematic error, and total sequencing throughput, and wherein the modified polymerase includes one or more amino acid substitutions selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A. To analyze the sequencing properties of the modified polymerase of the method of the invention, an emulsion PCR template amplification reaction can be used, and in particular embodiments using conditions that include 125 mM KCl or 125 mM NaCl, as sample preparation followed by a nucleic acid sequencing reaction. For the sake of clarity, the emulsion PCR template amplification reaction and the nucleic acid sequence reaction recited above, are not steps of the method of this embodiment of the invention. Rather, they are part of a method that can be used to determine whether a polymerase is a modified polymerase used in the recited method embodiment of the invention.

In certain embodiments, the sequencing workflow under which a sequencing property of the modified polymerase is analyzed is a next-generation (i.e. massively parallel, high throughput) sequencing workflow (e.g., a workflow used in an Ion Torrent System, Illumina HiSeq or True Seq or X-10 system). In some embodiments, the sequencing workflow uses an ISFET based sequencing system workflow. In certain embodiments, the sequencing property is analyzed using an Ion Torrent (Life Technologies, Carlsbad, Calif.) sequencing workflow and system, as exemplified herein. In certain aspects, the modified polymerase used in the method has improved thermostability at 95° C. for 6 minutes as compared to the thermostability of SEQ ID NO: 1 at 95° C. for 6 minutes. In certain illustrative embodiments of these aspects, the thermostable modified polymerase, or the biologically active fragment thereof, used in the method includes G418C or E397V. In yet further embodiments, in addition to a G418C or in particular aspects, an E397V mutation, the isolated peptide further includes one or more amino acid substitutions selected from the group consisting of E745T, L763F and E805, wherein the numbering is relative to SEQ ID NO: 1. In certain aspects, the method includes a hot start, as is known in the PCR arts. In these methods of the invention that include a hot start, compositions in which the method is performed can include a reagent such as an oligonucleotide and/or an aptamer that is used for the hot start or the modified polymerase can be chemically modified to provide a hot start mechanism.

In one embodiment of the invention one or more properties exhibited by the modified polymerase or the biologically active fragment thereof used in the method, include at least two, three, four, five, six, or all sequencing workflow properties selected from increased AQ20 mean read length reads, reduced strand bias, increased base coverage, increased accuracy, increased sequencing throughput (Mb) and increased uniformity of coverage, relative to a reference polymerase having a sequence of SEQ ID NO: 34 and/or SEQ ID NO: 1. In some embodiments the modified polymerase or biologically active fragment thereof, where one mutation is E397V, another mutation is P6N, E745T and/or L763F. In another embodiment, that may or may not include E397V, the mutations include L763F and/or E805I, P6N and/or E295F, or E745T and/or E794C.

In a further embodiment of the invention the one or more properties of the mutant polymerase used in the method are exhibited when, or can be determined by performing an emulsion PCR template amplification reaction on a library constructed from a template having a GC content of 65%. For the sake of clarity, such steps are not part of the inventive method, but rather are for determining whether a modified polymerase meets the criteria for a modified polymerase that is used in the method. In certain embodiments the reference polymerase used for the polymerase criteria testing is SEQ ID NO:34, and in certain particularly illustrative embodiments, the reference polymerase is SEQ ID NO:1.

In one embodiment of the inventive method, the modified polymerase or biologically active fragment thereof used in the method includes a mutation selected from A77E, A97V, K240I, L287T, or K292C relative to a reference polymerase having a sequence of SEQ ID NO:1. In exemplary aspects of this embodiment, the one or more properties of the modified polypeptide used in the method include a sequencing property analyzed using a next-generation (high throughput) nucleic acid sequencing reaction where the modified polymerase or biologically active fragment thereof is tested for such properties using an emulsion PCR template amplification reaction on a library constructed from a template with a GC content of 65%.

In certain embodiments, the polymerase used in the method comprises 50, 75, 100, 150, 175, 200, 250, 300, 350, 400, 500, 600, 700, or 800 contiguous amino acid residues of SEQ ID NO:1 or SEQ ID NO:34 and has at least 70%, 75%, 80%, 85%, 90%, 95%, 96%, 97%, 98%, or 99%, identity to SEQ ID NO: 1 or SEQ ID NO: 34, or a biologically active fragment thereof, In certain embodiments the modified polymerase used in the method includes SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In yet another embodiment of the invention, provided herein is a method for obtaining sequence information from a nucleic acid template, includes: providing a reaction mixture, including the nucleic acid template hybridized to a sequencing primer and bound to a modified polymerase or a biologically active fragment thereof, contacting the template nucleic acid with at least one type of nucleotide triphosphate, wherein the contacting includes incorporating one or more nucleotides from the at least one type of nucleotide onto the 3' end of the sequencing primer and generating an extended primer product; detecting the presence of the extended primer product in the reaction mixture, thereby determining whether nucleotide incorporation has occurred; and identifying at least one of the one or more nucleotides incorporated from the at least one type of nucleotide triphosphate, wherein the modified polymerase or the biologically active fragment thereof, has at least 70, 75, 80, 85, 90, 95, 96, 97, 98, or 99% sequence identity to SEQ ID NO:1 or SEQ ID NO:34, exhibits polymerase activity and exhibits an improvement, relative to a reference polymerase of SEQ ID NO:1 and/or SEQ ID NO:34, in one or more properties selected from thermostability and/or a sequencing workflow property selected from read length, accuracy, strand bias, systematic error, and total sequencing throughput, and the modified polymerase includes one or more amino acid substitutions selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A. The sequencing workflow properties of the modified polymerase or the biologically active fragment thereof, can be analyzed using an emulsion PCR template amplification reaction, for example that includes 125 mM KCl or 125 mM NaCl, during sample preparation of a nucleic acid sequencing reaction. In certain embodiments, the method is a next-generation sequencing method. In some embodiments, the method uses an ISFET detection system.

In certain aspects, the modified polymerase used in the method has improved thermostability at 95° C. for 6 minutes as compared to the thermostability of SEQ ID NO: 1 at 95° C. for 6 minutes. In certain illustrative embodiments of these aspects, the thermostable modified polymerase, or the biologically active fragment thereof, used in the method includes G418C or E397V. In yet further embodiments, in addition to a G418C or in particular aspects, an E397V mutation, the isolated peptide further includes one or more amino acid substitutions selected from the group consisting of E745T, L763F and E805I, wherein the numbering is relative to SEQ ID NO: 1.

In one embodiment of the invention one or more properties exhibited by the modified polymerase or the biologically active fragment thereof used in the method, include at least two, three, four, five, six, or all sequencing workflow properties selected from increased AQ20 mean read length reads, reduced strand bias, increased base coverage, increased accuracy, increased sequencing throughput (Mb) and increased uniformity of coverage, relative to a reference polymerase having a sequence of SEQ ID NO: 34 and/or SEQ ID NO: 1. In some embodiments the modified polymerase or biologically active fragment thereof, where one mutation is E397V, another mutation is P6N, E745T and/or L763F. In another embodiment, that may or may not include E397V, the mutations include L763F and/or E805I, P6N and/or E295F, or E745T and/or E794C.

In one embodiment of the inventive method, the modified polymerase or biologically active fragment thereof used in the method includes a mutation selected from A77E, A97V, K240I, L287T, or K292C relative to a reference polymerase having a sequence of SEQ ID NO:1. In exemplary aspects of this embodiment, the one or more properties of the modified polypeptide used in the method include a sequencing property analyzed using a next-generation (high throughput) nucleic acid sequencing reaction where the modified polymerase or biologically active fragment thereof is tested for such properties using an emulsion PCR template amplification reaction on a library constructed from a template with a GC content of 65%.

In certain embodiments, the polymerase used in the method comprises 50, 75, 100, 150, 175, 200, 250, 300, 350, 400, 500, 600, 700, or 800 contiguous amino acid residues of SEQ ID NO:1 or SEQ ID NO:34 and has at least 70%, 75%, 80%, 85%, 90%, 95%, 96%, 97%, 98%, and 99%, identity to SEQ ID NO: 1 or SEQ ID NO: 34, or a biologically active fragment thereof, In certain embodiments the modified polymerase used in the method includes SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:

9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In further aspects of the method the contacting, detecting and identifying steps are repeated more than once, thereby identifying a plurality of sequential nucleotide incorporations, wherein at least one of the nucleotides incorporated. In certain aspects, is a reversible terminator nucleotide.

In another embodiment, provided herein is a kit with two or more vessels, where one vessel includes a component for performing a nucleic acid polymerization reaction, and another vessel comprises a modified polymerase, or a biologically active fragment thereof, that has at least 70, 75, 80, 85, 90, 95, 96, 97, 98, or 99% sequence identity to SEQ ID NO:1 or SEQ ID NO:34, that exhibits polymerase activity and an that exhibits an improvement, relative to a reference polymerase of SEQ ID NO:1 and/or Seq ID NO:34, in one or more properties selected from thermostability and/or a sequencing workflow property selected from read length, accuracy, strand bias, systematic error, and total sequencing throughput, and the modified polymerase includes one or more amino acid substitutions selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A. The properties can be measured using an emulsion PCR template amplification reaction, which in certain illustrative embodiments is performed in the presence of 125 mM KCl or 125 mM NaCl, during sample preparation of a nucleic acid sequencing reaction, such as a high throughput or next-generation sequence reaction.

In further embodiments of the invention the kit includes nucleotide tri-phosphates, $MgCl_2$, and/or a buffer for a nucleic acid polymerization reaction. The kit can further include a reagent for a hot start mechanism. In yet a further embodiment the kit includes a component for forming an emulsion.

In some embodiments, the disclosure relates generally to methods (and related kits, systems, apparatuses and compositions) for performing a nucleotide polymerization reaction comprising or consisting of contacting a modified polymerase or a biologically active fragment thereof with a nucleic acid template in the presence of one or more nucleotides, where the modified polymerase or the biologically active fragment thereof includes one or more amino acid modifications relative to a reference polymerase, and where the modified polymerase or the biologically active fragment thereof has improved accuracy, coverage and/or processivity as compared to the reference polymerase, and polymerizing at least one of the one or more nucleotides using the modified polymerase or the biologically active fragment thereof.

In some embodiments, the disclosure relates generally to methods (and related kits, systems, apparatuses and compositions) for performing a nucleotide polymerization reaction comprising or consisting of contacting a modified polymerase or a biologically active fragment thereof with a nucleic acid template in the presence of one or more nucleotides, where the modified polymerase or the biologically active fragment thereof includes one or more amino acid modifications relative to a reference polymerase, and where the modified polymerase or the biologically active fragment thereof has an increased thermostability relative to the reference polymerase, and polymerizing at least one of the one or more nucleotides using the modified polymerase or the biologically active fragment thereof. In some embodiments, the method includes polymerizing at least one of the one or more nucleotides using the modified polymerase or the biologically active fragment thereof in the presence of a high ionic strength solution. In some embodiments, a high ionic strength solution can include a solution in excess of 100 mM KCl. In some embodiments, a high ionic strength solution includes a solution that is at least 120 mM KCl. In some embodiments, a high ionic strength solution includes a solution that is 125 mM to 200 mM KCl.

In some embodiments, the method can further include polymerizing one of the at least one nucleotides in a template-dependent fashion. In some embodiments, the polymerizing is performed under thermocycling conditions. In some embodiments, the method can further include hybridizing a primer to the nucleic acid template prior to, during, or after the contacting, and where the polymerizing includes polymerizing one of the at least one nucleotides onto an end of the primer using the modified polymerase or the biologically active fragment thereof. In some embodiments, the polymerizing is performed in the proximity of a sensor that is capable of detecting the polymerization of the at least one nucleotide by the modified polymerase or the biologically active fragment thereof. In some embodiments, the method can further include detecting a signal indicating the polymerization of the at least one nucleotide by the modified polymerase or the biologically active fragment thereof using a sensor. In some embodiments, the sensor is an ISFET. In some embodiments, the sensor can include a detectable label or detectable reagent within the polymerizing reaction.

In some embodiments, the modified polymerase or the biologically active fragment thereof comprises or consists of at least 80% identity to SEQ ID NO: 1. In some embodiments, the modified polymerase or the biologically active fragment thereof comprises or consists of at least 100 contiguous amino acid residues having at least 90% identity to SEQ ID NO: 1, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 90% identity to SEQ ID NO: 1, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 95% identity to SEQ ID NO: 1, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 95% identity to SEQ ID NO: 1, wherein the modified polymerase or biological active fragment thereof has improved thermostability as compared to SEQ ID NO: 1.

In some embodiments, the modified polymerase or the biologically active fragment thereof comprises or consists of at least 100 contiguous amino acid residues having at least 98% identity to SEQ ID NO: 1, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 98% identity to SEQ ID NO: 1, wherein the modified polymerase or biologically active fragment thereof has improved thermostability as compared to SEQ ID NO: 1.

In some embodiments, the modified polymerase or the biologically active fragment thereof comprises or consists of at least 90% identity to SEQ ID NO: 1. In some embodiments, the modified polymerase or the biologically active fragment thereof comprises or consists of at least 100 contiguous amino acid residues having at least 90% identity to SEQ ID NO: 1, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 90% identity to SEQ ID NO: 1, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 95% identity to SEQ ID NO: 1, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 95% identity to SEQ ID NO: 1, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 98% identity to SEQ ID NO: 1, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 98% identity to SEQ ID NO: 1, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 90% identity to SEQ ID NO: 2, and wherein the modified polymerase or biological active fragment thereof has improved thermostability as compared to SEQ ID NO: 1.

In some embodiments, the modified polymerase or the biologically active fragment thereof comprises or consists of at least 150 contiguous amino acid residues having at least 95% identity to SEQ ID NO: 2, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 90% identity to SEQ ID NO: 3, and wherein the modified polymerase or biological active fragment thereof has improved thermostability as compared to SEQ ID NO: 1.

In some embodiments, the modified polymerase or the biologically active fragment thereof comprises or consists of at least 150 contiguous amino acid residues having at least 95% identity to SEQ ID NO: 3, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 90% identity to SEQ ID NO: 4, and wherein the modified polymerase or biological active fragment thereof has improved thermostability as compared to SEQ ID NO: 1.

In some embodiments, the modified polymerase or the biologically active fragment thereof comprises or consists of at least 150 contiguous amino acid residues having at least 95% identity to SEQ ID NO: 4, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 98% identity to SEQ ID NO: 2, SEQ ID NO: 3 or SEQ ID NO: 4, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 99% identity to SEQ ID NO: 2, SEQ ID NO: 3 or SEQ ID NO: 4, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 98% identity to SEQ ID NO: 2, SEQ ID NO: 3 or SEQ ID NO: 4, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 99% identity to SEQ ID NO: 2, SEQ ID NO: 3 or SEQ ID NO: 4, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 90% identity to SEQ ID NO: 2, SEQ ID NO: 3 or SEQ ID NO: 4, and wherein the modified polymerase or biological active fragment thereof has improved thermostability as compared to SEQ ID NO: 34. In some embodiments, the modified polymerase or the biologically active fragment thereof comprises or consists of at least 150 contiguous amino acid residues having at least 95% identity to SEQ ID NO: 2, SEQ ID NO: 3 or SEQ ID NO: 4, and wherein the modified polymerase or biological active fragment thereof has improved thermostability as compared to SEQ ID NO: 34. In some embodiments, the modified polymerase or the biologically active fragment thereof comprises or consists of at least 100 contiguous amino acid residues having at least 98% identity to SEQ ID NO: 2, SEQ ID NO: 3 or SEQ ID NO: 4, and wherein the modified polymerase or biological active fragment thereof has improved thermostability as compared to SEQ ID NO: 34. In some embodiments, the modified polymerase or the biologically active fragment thereof comprises or consists of at least 150 contiguous amino acid residues having at least 99% identity to SEQ ID NO: 2, SEQ ID NO: 3 or SEQ ID NO: 4, wherein the modified polymerase or biologically active fragment thereof has improved thermostability as compared to SEQ ID NO: 34.

In some embodiments, the modified polymerase or the biologically active fragment thereof comprises or consists of at least 100 contiguous amino acid residues having at least 90% identity to SEQ ID NO: 2, SEQ ID NO: 3 or SEQ ID NO: 4, and wherein the modified polymerase or biological active fragment thereof has improved accuracy as compared to SEQ ID NO: 34. In some embodiments, the modified polymerase or the biologically active fragment thereof comprises or consists of at least 150 contiguous amino acid residues having at least 95% identity to SEQ ID NO: 2, SEQ ID NO: 3 or SEQ ID NO: 4, and wherein the modified polymerase or biological active fragment thereof has improved accuracy as compared to SEQ ID NO: 34. In some embodiments, the modified polymerase or the biologically active fragment thereof comprises or consists of at least 100 contiguous amino acid residues having at least 98% identity to SEQ ID NO: 2, SEQ ID NO: 3 or SEQ ID NO: 4, and wherein the modified polymerase or biological active fragment thereof has improved accuracy as compared to SEQ ID NO: 34. In some embodiments, the modified polymerase or the biologically active fragment thereof comprises or consists of at least 150 contiguous amino acid residues having at least 99% identity to SEQ ID NO: 2, SEQ ID NO: 3 or SEQ ID NO: 4, wherein the modified polymerase or biologically active fragment thereof has improved accuracy as compared to SEQ ID NO: 34.

In some embodiments, the disclosure generally relates to methods (and related kits, apparatus, systems and compositions) for performing nucleic acid amplification comprising or consisting of generating an amplification reaction mixture having a modified polymerase or a biologically active fragment thereof, a primer, a nucleic acid template, and one or more nucleotides, where the modified polymerase or the biologically active fragment thereof includes one or more amino acid modifications relative to a reference polymerase and has improved thermostability relative to the reference polymerase; and subjecting the amplification reaction mixture to amplifying conditions, where at least one of the one or more nucleotides is polymerized onto the end of the primer using the modified polymerase or the biologically active fragment thereof. In some embodiments, the modified polymerase or the biologically active fragment thereof having improved thermostability relative to the reference polymerase (e.g., SEQ ID NO: 1 or SEQ ID NO: 34), comprises or consists of at least 80% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof having improved thermostability relative to the reference polymerase (e.g., SEQ ID NO: 1 or SEQ ID NO: 34), comprises or consists of at least 90% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof having improved thermostability relative to the reference polymerase (e.g., SEQ ID NO: 1 or SEQ ID NO: 34), comprises or consists of at least 95% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof having improved thermostability relative to the reference polymerase (e.g., SEQ ID NO: 1 or SEQ ID NO: 34), comprises or consists of at least 98% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof having improved thermostability relative to the reference polymerase (e.g., SEQ ID NO: 1 or SEQ ID NO: 34), comprises or consists of at least 99% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure generally relates to methods (and related kits, apparatus, systems and compositions) for performing nucleic acid amplification comprising or consisting of generating an amplification reaction mixture having a modified polymerase or a biologically active fragment thereof, a primer, a nucleic acid template, and one or more nucleotides, where the modified polymerase or the biologically active fragment thereof includes one or more amino acid modifications relative to a reference polymerase and has improved accuracy relative to the reference polymerase; and subjecting the amplification reaction mixture to amplifying conditions, where at least one of the one or more nucleotides is polymerized onto the end of the primer using the modified polymerase or the biologically active fragment thereof. In some embodiments, the modified polymerase or the biologically active fragment having improved accuracy relative to the reference polymerase (e.g., SEQ ID NO: 1 or SEQ ID NO: 34) comprises or consists of at least 80% identity SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the method further includes determining the identity of the one or more nucleotides polymerized by the modified polymerase. In some embodiments, the method further includes determining the number of nucleotides polymerized by the modified polymerase. In some embodiments, at least 50% of the one or more nucleotides polymerized by the modified polymerase are identified. In some embodiments, substantially all of the one or more nucleotides polymerized by the modified polymerase are identified. In some embodiments, the polymerization occurs in the presence of a high ionic strength solution. In some embodiments the high ionic strength solution comprises 125 mM to 200 mM salt. In some embodiments, the polymerization occurs in the presence of an ionic strength solution of at least 120 mM salt. In some embodiments, the high ionic strength solution comprises KCl and/or NaCl.

In some embodiments, the modified polymerase or the biologically active fragment thereof having improved accuracy relative to the reference polymerase (e.g., SEQ ID NO: 1 or SEQ ID NO: 34), comprises or consists of at least 90% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof having improved accuracy relative to the reference polymerase (e.g., SEQ ID NO: 1 or SEQ ID NO: 34), comprises or consists of at least 95% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof having improved accuracy relative to the reference polymerase (e.g., SEQ ID NO: 1 or SEQ ID NO: 34), comprises or consists of at least 98% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof having improved accuracy relative to the reference polymerase (e.g., SEQ ID NO: 1 or SEQ ID NO: 34), comprises or consists of at least 99% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof further comprises at least 25 contiguous amino acids of the polymerase DNA binding domain. In some embodiments, the modified polymerase or the biologically active fragment thereof comprises at least 50 contiguous amino acid residues of the polymerase DNA binding domain. In some embodiments, the modified polymerase or the biologically active fragment thereof comprises or consists of at least 100 contiguous amino acid residues of the polymerase DNA binding domain. In some embodiments, the modified polymerase or the biologically active fragment thereof comprises or consists of at least 100 contiguous amino acid residues of the polymerase DNA binding domain, while also having at least 90% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof comprises or consists of at least 150 contiguous amino acid residues of the polymerase DNA binding domain having at least 95% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the methods (and related kits, systems, apparatuses and compositions) include amplifying conditions having a high ionic strength solution. In one embodiment, a high ionic strength solution is a solution having at least 120 mM KCl. In some embodiments, a high ionic strength solution includes a solution that is 125 mM to 200 mM KCl.

In some embodiments, the disclosure generally relates to methods (and related kits, systems, apparatuses and compositions) for performing a nucleotide polymerization reaction comprising or consisting of mixing a modified polymerase or a biologically active fragment thereof with a nucleic acid template in the presence of one or more nucleotides, where the modified polymerase or the biologically active fragment thereof includes one or more amino acid modifications relative to a reference polymerase (such as SEQ ID NO: 1 or SEQ ID NO: 34; and polymerizing at least one of the one or more nucleotides using the modified polymerase or the biologically active fragment thereof in the mixture. In some embodiments, the modified polymerase or the biologically active fragment thereof has increased accuracy as determined by measuring increased accuracy in the presence of a high ionic strength solution. In some embodiments, the high ionic strength solution refers to a reaction mixture for performing nucleotide polymerization having at least 120 mM KC. In some embodiments, a high ionic strength solution includes a solution that is 125 mM to 200 mM KCl.

In some embodiments, the methods (and related kits, apparatus, systems and compositions) comprise a modified polymerase or a biologically active fragment thereof comprising or consisting of at least 80% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof comprises or consists of at least 90% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof comprises or consists of at least 95% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof comprises or consists of at 98% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure generally relates to methods (and related kits, systems, apparatus and compositions) for detecting nucleotide incorporation comprising or consisting of performing a nucleotide incorporation reaction using a modified polymerase or a biologically active fragment thereof having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33, a nucleic acid template, and one or more nucleotide triphosphates; generating the nucleotide incorporation; and detecting the nucleotide incorporation. Detecting nucleotide incorporation can occur via any appropriate means such as PAGE, fluorescence, dPCR quantitation, nucleotide by-product production (e.g., hydrogen ion or pyrophosphate detection; suitable nucleotide by-product detection systems include without limitation, next-generation sequencing platforms such as Rain Dance, Roche 454, and Ion Torrent Systems)) or nucleotide extension product detection (e.g., optical detection of extension products or detection of labelled nucleotide extension products). In some embodiments, the methods (and related kits, systems, apparatus and compositions) for detecting nucleotide incorporation include or consist of detecting nucleotide incorporation using a modified polymerase or a biologically active fragment thereof that includes at least 95% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the method of detecting nucleotide incorporation includes or consists of detecting nucleotide incorporation using a modified polymerase or a biologically active fragment thereof that includes at least 98% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the method of detecting nucleotide incorporation includes or consists of detecting nucleotide incorporation by a modified polymerase or a biologically active fragment thereof that includes at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the method further comprises determining the identity of one or more nucleotides in the nucleotide incorporation. In some embodiments, the byproduct of the nucleotide incorporation is a hydrogen ion. In some embodiments, the byproduct of the nucleotide incorporation is a pyrophosphate. In some embodiments, the byproduct of the nucleotide incorporation is a labeled nucleotide extension product. In some embodiments, the method of detecting nucleotide incorporation includes generating the nucleotide incorporation under emulsion PCR or bridge PCR conditions.

In some embodiments, the disclosure generally relates to methods (and related kits, systems, apparatus and compositions) for detecting a change in ion concentration during a nucleotide polymerization reaction comprising or consisting of performing a first nucleotide polymerization reaction on a nucleic acid template or nucleic acid library in the presence of one or more nucleotides to be incorporated during the first nucleotide polymerization reaction, wherein the first nucleotide polymerization reaction includes a modified polymerase or a biologically active fragment thereof having at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; and performing a second nucleotide polymerization reaction, wherein the second nucleotide polymerization reaction detects at least one type of ion concentration change during the course of the second nucleotide polymerization reaction and provides a signal indicating a change in ion concentration of the at least one type of ion. In some embodiments, the ion is a hydrogen ion. In some embodiments, the ion is a pyrophosphate ion. In some embodiments, the signal indicating a change in ion concentration is a relative increase in the production of hydrogen ions in the polymerization reaction. In some embodiments, detection of at least one type of ion concentration change is monitored using an ISFET. In some embodiments, the modified polymerase or the biologically active fragment from the first nucleotide polymerization reaction comprises or consists of at least 150 contiguous amino acid residues of a polymerase having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the modified polymerase or the biological active fragment from the first nucleotide polymerization reaction comprises or consists of at least 200 contiguous amino acid resides of the polymerase having at least 95% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the modified polymerase or the biological active fragment from the first nucleotide polymerization reaction comprises or consists of at least 250 contiguous amino acid resides of the polymerase having at least 98% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the modified polymerase or the biological active fragment from the first nucleotide polymerization reaction comprises or consists of a polymerase having at least 99% identity to SEQ ID NO:2, SEQ ID NO:3, SEQ ID NO:4, SEQ ID NO:5, SEQ ID NO:6, SEQ ID NO:7, SEQ ID NO:8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure generally relates to methods (and related kits, systems, apparatus and compositions) for amplifying a nucleic acid comprising or consisting of contacting a nucleic acid with a polymerase or a biologically active fragment thereof comprising at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 under suitable conditions for amplification of the nucleic acid; and amplifying the nucleic acid. In some embodiments, the amplifying is performed using a polymerase chain reaction, emulsion polymerase chain reaction, isothermal amplification reaction, recombinase polymerase amplification reaction, proximity ligation amplification, rolling circle amplification or strand displacement amplification. In some embodiments, the amplifying includes clonally amplifying the nucleic acid in solution. In some embodiments, the amplifying includes clonally amplifying the nucleic acid on a solid support such as a nucleic acid bead, flow cell, nucleic acid array, or wells present on the surface of the solid support. In some embodiments, the amplifying is performed using a polymerase or biologically active fragment comprising a thermostable DNA polymerase. In some embodiments, the polymerase or biologically active fragment comprises a DNA polymerase having improved thermostability as compared to a reference polymerase, such as SEQ ID NO: 1 or SEQ ID NO: 34. In some embodiments, the polymerase or biologically active fragment comprises a DNA polymerase having improved accuracy as compared to a reference polymerase, such as SEQ ID NO: 1 or SEQ ID NO: 34.

In some embodiments, the methods (and related kits, systems, apparatus and compositions) for amplifying a nucleic acid comprising contacting a nucleic acid with a polymerase or a biologically active fragment thereof comprising at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 under suitable conditions for amplification of the nucleic acid; and amplifying the nucleic acid. In some embodiments, the polymerase or biologically active fragment comprises a DNA polymerase having an improved average read length as compared to the average read length obtained using a DNA polymerase encoded by SEQ ID NO: 1 or SEQ ID NO: 34 under identical amplification conditions.

In some embodiments, the methods for amplifying a nucleic acid comprise contacting a nucleic acid with a polymerase or a biologically active fragment thereof comprising at least 95% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 under suitable conditions for amplification of the nucleic acid; and amplifying the nucleic acid. In some embodiments, the method includes a polymerase or biologically active fragment having an improved average read length as compared to the average read length obtained using a DNA polymerase encoded by SEQ ID NO: 1 or SEQ ID NO: 34 under identical amplification conditions.

In some embodiments, the methods for amplifying a nucleic acid comprise contacting a nucleic acid with a polymerase or a biologically active fragment thereof comprising at least 98% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 under suitable conditions for amplification of the nucleic acid; and amplifying the nucleic acid. In some embodiments, the method includes a polymerase or biologically active fragment having an improved average read length as compared to the average read length obtained using a DNA polymerase encoded by SEQ ID NO: 1 or SEQ ID NO: 34 under identical amplification conditions.

In some embodiments, the methods for amplifying a nucleic acid comprise contacting a nucleic acid with a polymerase or a biologically active fragment thereof comprising at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 under suitable conditions for amplification of the nucleic acid; and amplifying the nucleic acid. In some embodiments, the method includes a polymerase or biologically active fragment having an improved average read length as compared to the average read length obtained using a DNA polymerase encoded by SEQ ID NO: 1 or SEQ ID NO: 34 under identical amplification conditions.

In some embodiments, average read length is determined by analyzing the read length of the amplified nucleic acids obtained using one or more of the modified polymerase provided herein, across all reads to establish an average read length and comparing the average read length to the average read length obtained using the reference polymerase.

In some embodiments, the disclosure generally relates to methods for amplifying a nucleic acid comprising or consisting of contacting a nucleic acid with a polymerase or a biologically active fragment thereof comprising at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33, under suitable conditions for amplification of the nucleic acid; and amplifying the nucleic acid. In some embodiments, the amplifying is performed by a polymerase or biologically active fragment having improved templating efficiency as compared to a reference sample, such as SEQ ID NO: 1 or SEQ ID NO: 34. In some embodiments the method for amplifying a nucleic acid comprises amplifying the nucleic acid under emulsion PCR conditions. In some embodiments the method for amplifying a nucleic acid comprises amplifying the nucleic acid under bridge PCR conditions. In some embodiments, the bridge PCR conditions include hybridizing one or more of the amplified nucleic acids to a solid support. In some embodiments, the hybridized one or more amplified nucleic acids can be used as a template for further amplification. In some embodiments, the modified polymerase or biologically active fragment thereof comprises a polymerase that is derived from *Thermus aquaticus* DNA polymerase (Taq). SEQ ID NO: 1 is the full-length, wild-type, nucleic acid sequence of the DNA polymerase, *Thermus aquaticus* (Taq). In some embodiments, Taq DNA polymerase can be used as a reference polymerase in the methods, kits, apparatus, systems and compositions described herein.

In some embodiments, the disclosure generally relates to methods (and related kits, systems, apparatus and compositions) for synthesizing a nucleic acid comprising or consisting of incorporating at least one nucleotide onto the end of a primer using a modified polymerase or a biologically active fragment thereof having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. Optionally, the method further comprises detecting incorporation of the at least one nucleotide onto the end of the primer. In some embodiments, the method further includes determining the identity of at least one of the at least one nucleotide incorporated onto the end of the primer. In some embodiments, the method can include determining the identity of all nucleotides incorporated onto the end of the primer. In some embodiments, the method includes synthesizing the nucleic acid in a template-dependent manner. In some embodiments, the method can include synthesizing the nucleic acid in solution, on a solid support, or in an emulsion (such as emPCR).

In some embodiments, the disclosure is generally related to an isolated and purified polypeptide comprising or consisting of at least 80% identity to SEQ ID NO: 1 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 1 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 95% identity to SEQ ID NO: 1 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 97% identity to SEQ ID NO: 1 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 98% identity to SEQ ID NO: 1 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 99% identity to SEQ ID NO: 1 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of SEQ ID NO: 2.

In some embodiments, the disclosure is generally related to an isolated and purified polypeptide comprising or consisting of at least 80% identity to SEQ ID NO: 2 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 2 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 95% identity to SEQ ID NO: 2 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 97% identity to SEQ ID NO: 2 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 98% identity to SEQ ID NO: 2 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 99% identity to SEQ ID NO: 2 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of SEQ ID NO: 3.

In some embodiments, the disclosure is generally related to an isolated and purified polypeptide comprising or consisting of at least 80% identity to SEQ ID NO: 3 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, E790G, E794C and L828A.

In some embodiments, the disclosure is generally related to an isolated and purified polypeptide comprising or consisting of at least 90% identity to SEQ ID NO: 3 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, E790G, E794C and L828A.

In some embodiments, the disclosure is generally related to an isolated and purified polypeptide comprising or consisting of at least 95% identity to SEQ ID NO: 3 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, E790G, E794C and L828A.

In some embodiments, the disclosure is generally related to an isolated and purified polypeptide comprising or consisting of at least 98% identity to SEQ ID NO: 3 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, E790G, E794C and L828A.

In some embodiments, the disclosure is generally related to an isolated and purified polypeptide comprising or consisting of SEQ ID NO: 4.

In some embodiments, disclosure is generally related to an isolated and purified polypeptide comprising or consisting of at least 80% identity to SEQ ID NO: 4 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E790G, E794C, E805I and L828A.

In some embodiments, disclosure is generally related to an isolated and purified polypeptide comprising or consisting of at least 90% identity to SEQ ID NO: 4 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E790G, E794C, E805I and L828A.

In some embodiments, disclosure is generally related to an isolated and purified polypeptide comprising or consisting of at least 95% identity to SEQ ID NO: 4 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E790G, E794C, E805I and L828A.

In some embodiments, disclosure is generally related to an isolated and purified polypeptide comprising or consisting of at least 98% identity to SEQ ID NO: 4 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E790G, E794C, E805I and L828A.

In some embodiments, the disclosure is generally related to an isolated and purified polypeptide comprising or consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to an isolated and purified polypeptide comprising or consisting of at least 90% identity to SEQ ID NO: 5 and having one or more amino acid mutations selected from the group consisting of A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, E790G, E794C, E805I and L828A.

In some embodiments, the disclosure is generally related to an isolated and purified polypeptide comprising or consisting of at least 90% identity to SEQ ID NO: 6 and having one or more amino acid mutations selected from the group consisting of P6N, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 7 and having one or more amino acid mutations selected from the group consisting of P6N, A77E, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 8 and having one or more amino acid mutations selected from the group consisting of P6N, A77E, A97V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 9 and having one or more amino acid mutations selected from the group consisting of P6N, A77E, A97V, L193V, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 10 and having one or more amino acid mutations selected from the group consisting of P6N, A77E, A97V, L193V, K240I, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 11 and having one or more amino acid mutations selected from the group consisting of P6N, A77E, A97V, L193V, K240I, R266Q, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 12 and having one or more amino acid mutations selected from the group consisting of P6N, A77E, A97V, L193V, K240I, R266Q, E267T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 13 and having one or more amino acid mutations selected from the group consisting of P6N, A77E, A97V, L193V, K240I, R266Q, E267T, L287T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 14 and having one or more amino acid mutations selected from the group consisting of P6N, A77E, A97V, L193V, K240I, R266Q, E267T, L287T, P291T, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 15 and having one or more amino acid mutations selected from the group consisting of P6N, A77E, A97V, L193V, K240I, R266Q, E267T, L287T, P291T, K292C, E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 16 and having one or more amino acid mutations selected from the group consisting of P6N, A77E, A97V, L193V, K240I, R266Q, E267T, L287T, P291T, K292C, E295F, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 17 and having one or more amino acid mutations selected from the group consisting of P6N, A77E, A97V, L193V, K240I, R266Q, E267T, L287T, P291T, K292C, E295F or E295N, E397V, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 18 and having one or more amino acid mutations selected from the group consisting of P6N, A77E, A97V, L193V, K240I, R266Q, E267T, L287T, P291T, K292C, E295F or E295N, E397V, G418C, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 19 and having one or more amino acid mutations selected from the group consisting of P6N, A77E, A97V, L193V, K240I, R266Q, E267T, L287T, P291T, K292C, E295F or E295N, E397V, G418C, L490Q, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 20 and having one or more amino acid mutations selected from the group consisting of P6N, A77E, A97V, L193V, K240I, R266Q, E267T, L287T, P291T, K292C, E295F or E295N, E397V, G418C, L490Q, A502S, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 21 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 22 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, L678F or L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 23 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678T, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 24 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F, S699W, E713W, V737A, E745T, L763F, E790G, E794C, E805I and L828A.

In some embodiments, the disclosure is generally related to an isolated and purified polypeptide comprising or consisting of at least 90% identity to SEQ ID NO: 25 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, E713W, V737A, E745T, L763F, E790G, E794C, E805I and L828A.

In some embodiments, the disclosure is generally related to an isolated and purified polypeptide comprising or consisting of at least 90% identity to SEQ ID NO: 26 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, V737A, E745T, L763F, E790G, E794C, E805I and L828A.

In some embodiments, the disclosure is generally related to an isolated and purified polypeptide comprising or consisting of at least 90% identity to SEQ ID NO: 27 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, E745T, L763F, E790G, E794C, E805I and L828A.

In some embodiments, the disclosure is generally related to an isolated and purified polypeptide comprising or consisting of at least 90% identity to SEQ ID NO: 28 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, L763F, E790G, E794C, E805I and L828A.

In some embodiments, the disclosure is generally related to an isolated and purified polypeptide comprising or consisting of at least 90% identity to SEQ ID NO: 29 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, E790G, E794C, E805I and L828A.

In some embodiments, the disclosure is generally related to an isolated and purified polypeptide comprising or consisting of at least 90% identity to SEQ ID NO: 30 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, L763F, E794C, E805I and L828A.

In some embodiments, the disclosure is generally related to an isolated and purified polypeptide comprising or consisting of at least 90% identity to SEQ ID NO: 31 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E805I and L828A.

In some embodiments, the disclosure is generally related to an isolated and purified polypeptide comprising or consisting of at least 90% identity to SEQ ID NO: 32 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C and L828A.

In some embodiments, the disclosure is generally related to an isolated and purified polypeptide comprising or consisting of at least 90% identity to SEQ ID NO: 33 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C and E805I.

In some embodiments, the disclosure is generally related to an isolated nucleic acid sequence comprising or consisting of a nucleic acid sequencing encoding a polypeptide having at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to an isolated nucleic acid sequence comprising or consisting of a nucleic acid sequencing encoding a polypeptide having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to an isolated nucleic acid sequence comprising or consisting of a nucleic acid sequencing encoding a polypeptide having at least 95% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to an isolated nucleic acid sequence comprising or consisting of a nucleic acid sequencing encoding a polypeptide having at least 98% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to an isolated nucleic acid sequence comprising or consisting of a nucleic acid sequencing encoding a polypeptide having at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a composition comprising an isolated nucleic acid sequence comprising or consisting of a nucleic acid sequence encoding a polypeptide having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a composition comprising an isolated nucleic acid sequence comprising or consisting of a nucleic acid sequence encoding a polypeptide having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33, and further comprising one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to a vector comprising an isolated nucleic acid sequence encoding a polypeptide or a biologically active fragment thereof selected from the group consisting of SEQ ID NO:2, SEQ ID NO:3, SEQ ID NO:4, SEQ ID NO:5, SEQ ID NO:6, SEQ ID NO:7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33. In some embodiments, the vector comprising the isolated nucleic acid sequence encoding a polypeptide or biologically active fragment thereof includes a DNA polymerase. In some embodiments, the DNA polymerase is a *Thermus aquaticus* (Taq) polymerase. In some embodiments, the DNA polymerase is a thermostable DNA polymerase. In some embodiments, the DNA polymerase is derived from a thermostable *Thermus aquaticus* (Taq) polymerase.

In some embodiments, the disclosure is generally related to a composition comprising an isolated polypeptide having at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a composition comprising an isolated polypeptide having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a composition comprising an isolated polypeptide having at least 95% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a composition comprising an isolated polypeptide having at least 98% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a composition comprising an isolated polypeptide having at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a composition comprising an isolated nucleic acid having at least 80% identity to SEQ ID NO: 1 and further comprising at least one amino acid substitution selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 and L828, wherein the numbering is specific to amino acid residues of SEQ ID NO: 1.

In some embodiments, the disclosure is generally related to a composition comprising an isolated nucleic acid having at least 80% identity to SEQ ID NO: 1 and further comprising at least one amino acid substitution selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A, wherein the numbering is specific to amino acid residues of SEQ ID NO: 1.

In some embodiments, the composition comprises at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 and further comprises at least one amino acid substitution selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 and L828, wherein the numbering is specific to amino acid residues of SEQ ID NO: 1.

In some embodiments, the composition comprises at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 and further comprises at least one amino acid substitution selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A, wherein the numbering is specific to amino acid residues of SEQ ID NO: 1.

In some embodiments, the composition comprises or consists of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the composition comprises at least 85%, 90%, 95%, 98% or 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33, and further comprising at least one amino acid substitution selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A, wherein the numbering is specific to amino acid residues of SEQ ID NO: 1.

In some embodiments, the disclosure is generally related to a kit comprising an isolated polypeptide having at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the kit comprises an isolated polypeptide having at least 90%, 95%, 96%, 97% 98% or 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the kit comprises an isolated polypeptide selected from the group consisting of SEQ ID NO:2, SEQ ID NO:3, SEQ ID NO:4, SEQ ID NO:5, SEQ ID NO:6, SEQ ID NO:7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the kit comprises an isolated polypeptide comprising or consisting of at least 250 contiguous amino acid residues having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the kit comprises an isolated polypeptide comprising or consisting of at least 450 contiguous amino acid residues having at least 95% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the kit comprises an isolated polypeptide comprising or consisting of at least 650 contiguous amino acid residues having at least 98% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the kits further comprise dNTPs, one of more buffers and/or MgCl.

In some embodiments, the disclosure generally relates to a polymerase or a biologically active fragment thereof having DNA polymerase activity and at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33, wherein the polymerase or the biologically active fragment having DNA polymerase activity includes at least one amino acid substitution as compared to SEQ ID NO: 1 or SEQ ID NO: 34.

In some embodiments, the at least one amino acid substitution as compared to SEQ ID NO: 1 or SEQ ID NO: 34 can impart a beneficial property to the polymerase or biologically active fragment thereof. In some embodiments, the beneficial property imparted to the polymerase or biologically active fragment thereof (as compared to SEQ ID NO: 1 or SEQ ID NO: 34) includes improved thermostability, improved read length, improved templating efficiency, improved performance in a high ionic strength solution or improved accuracy. In some embodiments, the beneficial property imparted to the polymerase or biologically active fragment thereof (as compared to SEQ ID NO: 1 or SEQ ID NO: 34) includes reduced strand bias of GC and AT rich nucleic acids. It will be generally understood that the beneficial property imparted to the polymerase or biological fragment (as compared to the properties of SEQ ID NO: 1 or SEQ ID NO: 34) can be determined by assessing and/or measuring such properties under identical conditions (e.g., comparing the properties of SEQ ID NO: 1 against the polymerase or biologically active fragment thereof, under identical conditions). For example, the accuracy of a DNA polymerase can be measured in terms of the longest perfect read (typically measured in terms of the number of nucleotides correctly included in the read) obtained from a nucleotide polymerization reaction. In some embodiments, the nucleotide polymerization reaction can be conducted using emulsion PCR, bridge PCR or hot-start PCR conditions. In some embodiments, one or more of the beneficial properties imparted to the polymerase or biologically active fragment thereof can be determined by assessing sequencing accuracy. In some embodiments, sequencing accuracy can be determined using any next-generation sequencing platform (e.g., Ion Torrent Systems, Illumina HiSeq or True Seq or X-10 systems). In some embodiments, sequencing accuracy can be determined using any ISFET based sequencing system.

In some embodiments, the disclosure generally relates to a substantially purified polymerase having an amino acid sequence comprising or consisting of at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 and further comprises at least one amino acid substitution selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 and L828, wherein the numbering is relative to SEQ ID NO: 34.

In some embodiments, the disclosure generally relates to a substantially purified polymerase having an amino acid sequence comprising or consisting of a fragment of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 that retains polymerase activity. In some embodiments, the polymerase activity, also referred to herein as polymerase properties or polymerase characteristics is selected from primer extension activity, strand displacement activity, proofreading activity, nick-initiated polymerase activity, reverse transcriptase activity accuracy, average read length, thermostability, processivity, strand bias or nucleotide polymerization activity. In some embodiments, the polymerase activity is selected from one or more sequencing based metrics selected from raw read accuracy, average read length, thermostability or processivity.

In some embodiments, the disclosure generally relates to a substantially purified polymerase having an amino acid sequence comprising or consisting of a biologically active fragment of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 having polymerase activity selected from improved read length, improved accuracy or improved thermostability as compared to polymerase activity of SEQ ID NO: 1 or SEQ ID NO: 34 under identical conditions. In some embodiments, the polymerase activity is determined in the presence of a high ionic strength solution. In some embodiments the high ionic strength solution is at least 120 mM Kcl. In some embodiments, the high ionic strength solution is from 125 mM KCl to 200 mM KCl.

In some embodiments, the disclosure generally relates to a substantially purified polymerase having an amino acid sequence comprising or consisting of at least 80% identity to SEQ ID NO: 1 and further comprising at least one amino acid substitution selected from the group consisting of A97, K240, L287 and K292, wherein the numbering is relative to SEQ ID NO: 1. In some embodiments, the disclosure generally relates to a substantially purified polymerase having an amino acid sequence comprising or consisting of at least 80% identity to SEQ ID NO: 1 and further comprising at least one amino acid substitution selected from the group consisting of A97V, K240I, L287T and K292C, wherein the numbering is relative to SEQ ID NO: 1.

In some embodiments, the disclosure generally relates to a substantially purified polymerase having an amino acid sequence comprising or consisting of at least 90% identity to SEQ ID NO: 1 and further comprising a E397 amino acid substitution, wherein the numbering is relative to SEQ ID NO: 1. In some embodiments, the disclosure generally relates to a substantially purified polymerase having an amino acid sequence comprising or consisting of at least 90% identity to SEQ ID NO: 1 and further comprising a E397V amino acid substitution, wherein the numbering is relative to SEQ ID NO: 1.

In some embodiments, the disclosure generally relates to a substantially purified polymerase having an amino acid sequence comprising or consisting of at least 90% identity to SEQ ID NO: 1 and further comprising a L763 amino acid substitution, wherein the numbering is relative to SEQ ID NO: 1. In some embodiments, the disclosure generally relates to a substantially purified polymerase having an amino acid sequence comprising or consisting of at least 90% identity to SEQ ID NO: 1 and further comprising a L763F amino acid substitution, wherein the numbering is relative to SEQ ID NO: 1.

In some embodiments, the disclosure generally relates to a substantially purified polymerase having an amino acid sequence comprising or consisting of at least 90% identity to SEQ ID NO: 1 and further comprising a E805 amino acid substitution, wherein the numbering is relative to SEQ ID NO: 1. In some embodiments, the disclosure generally relates to a substantially purified polymerase having an amino acid sequence comprising or consisting of at least 90% identity to SEQ ID NO: 1 and further comprising a E805I amino acid substitution, wherein the numbering is relative to SEQ ID NO: 1.

In some embodiments, the disclosure generally relates to a substantially purified polymerase having an amino acid sequence comprising or consisting of at least 90% identity to SEQ ID NO: 1 and further comprising a E745 amino acid substitution, wherein the numbering is relative to SEQ ID NO: 1. In some embodiments, the disclosure generally relates to a substantially purified polymerase having an amino acid sequence comprising or consisting of at least 90% identity to SEQ ID NO: 1 and further comprising a E745T amino acid substitution, wherein the numbering is relative to SEQ ID NO: 1.

In some embodiments, the disclosure generally relates to a substantially purified polymerase having an amino acid sequence comprising or consisting of at least 90% identity to SEQ ID NO: 34 and further comprising a E397 amino acid substitution, wherein the numbering is relative to SEQ ID NO: 34. In some embodiments, the disclosure generally relates to a substantially purified polymerase having an amino acid sequence comprising or consisting of at least 90% identity to SEQ ID NO: 34 and further comprising a E397V amino acid substitution, wherein the numbering is relative to SEQ ID NO: 34.

In some embodiments, the disclosure generally relates to a substantially purified polymerase having an amino acid sequence comprising or consisting of at least 90% identity to SEQ ID NO: 34 and further comprising a L763 amino acid substitution, wherein the numbering is relative to SEQ ID NO: 34. In some embodiments, the disclosure generally relates to a substantially purified polymerase having an amino acid sequence comprising or consisting of at least 90% identity to SEQ ID NO: 34 and further comprising a L763F amino acid substitution, wherein the numbering is relative to SEQ ID NO: 34.

In some embodiments, the disclosure generally relates to a substantially purified polymerase having an amino acid sequence comprising or consisting of at least 90% identity to SEQ ID NO: 34 and further comprising a E805 amino acid substitution, wherein the numbering is relative to SEQ ID NO: 34. In some embodiments, the disclosure generally relates to a substantially purified polymerase having an amino acid sequence comprising or consisting of at least 90% identity to SEQ ID NO: 34 and further comprising a E805 amino acid substitution, wherein the numbering is relative to SEQ ID NO: 34.

In some embodiments, the disclosure generally relates to a substantially purified polymerase having an amino acid sequence comprising or consisting of at least 90% identity to SEQ ID NO: 34 and further comprising a E745 amino acid substitution, wherein the numbering is relative to SEQ ID NO: 34. In some embodiments, the disclosure generally relates to a substantially purified polymerase having an amino acid sequence comprising or consisting of at least 90% identity to SEQ ID NO: 34 and further comprising a E745T amino acid substitution, wherein the numbering is relative to SEQ ID NO: 34.

In some embodiments, the disclosure relates generally to a composition comprising a recombinant polymerase homologous to SEQ ID NO: 1 or a biologically active fragment thereof having at least 90% identity to SEQ ID NO: 1, wherein the recombinant polymerase comprises a mutation or combination of mutations relative to SEQ ID NO: 1 selected from P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I or L828A. In some embodiments, the recombinant polymerase homologous to SEQ ID NO: 1 or a biologically active fragment thereof includes a thermostable DNA polymerase from a species other than *Thermus aquaticus* (Taq).

In some embodiments, the disclosure relates generally to a composition comprising a recombinant polymerase homologous to SEQ ID NO: 34 or a biologically active fragment thereof having at least 90% identity to SEQ ID NO: 34, wherein the recombinant polymerase comprises a mutation or combination of mutations relative to SEQ ID NO: 34 selected from P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I or L828A. In some embodiments, the recombinant polymerase homologous to SEQ ID NO: 34 or a biologically active fragment thereof includes a thermostable DNA polymerase from a species other than *Thermus aquaticus* (Taq). In some embodiments, the recombinant polymerase homologous to SEQ ID NO: 1 or SEQ ID NO: 34 includes a thermostable polymerase selected from the group consisting of Klentaq-235 DNA polymerase, Klentaq-278 DNA polymerase, Stoffel fragment, Klentaq-291 DNA polymerase, *Pyrococcus furiosus* DNA polymerase, *Pyrococcus* GB-D DNA polymerase, *Thermus flavus* DNA polymerase, *Thermus thermophilus* DNA polymerase, *Thermococcus literalis* DNA polymerase and a combination thereof.

In some embodiments, the disclosure relates generally to a composition comprising a recombinant polymerase homologous to SEQ ID NO: 34 or a biologically active fragment thereof having at least 80% identity to SEQ ID NO: 34 or a biologically active fragment thereof and where the recombinant polymerase comprises an E397 mutation. In some embodiments, the recombinant polymerase homologous to SEQ ID NO: 34 comprises a mutation that increases processivity, increases accuracy, increases average read length or improves thermostability, as compared to a reference polymerase lacking the corresponding mutation. In some embodiments, the increased processivity, increased accuracy, increased average read length, or improved thermostability is measured using an ISFET. In some embodiments, the ISFET is coupled to a semiconductor based sequencing platform. In some embodiments, the semiconductor based sequencing platform is a Personal Genome Machine or a Proton Sequencer (Life Technologies Corp., CA).

In some embodiments, the disclosure relates generally to a composition comprising a recombinant polymerase homologous to SEQ ID NO: 34 or a biologically active fragment thereof having at least 80% identity to SEQ ID NO: 34 or a biologically active fragment thereof and where the recombinant polymerase comprises a mutation or combination of mutations relative to SEQ ID NO: 34 selected from E397V, and where the polymerase further includes a mutation at one or more of P6N, A77E, A97V, L193V, K240I, R266Q, E267T, L287T, P291T, K292C, E295F or E295N, G418C, L490Q, A502S, S543V, D578E, R593G, L678F or L678T, E713W, V737A, E745T, L763F, E790G, E794C, E805I and L828A, wherein the numbering is relative to SEQ ID NO: 34.

In some embodiments, the disclosure relates generally to a composition comprising a recombinant polymerase homologous to SEQ ID NO: 34 or a biologically active fragment thereof having at least 80% identity to SEQ ID NO: 34 or a biologically active fragment thereof and where the recombinant polymerase comprises a mutation or combination of mutations relative to SEQ ID NO: 34 selected from E397V, L763F, E805I and E745T, wherein the numbering is relative to SEQ ID NO: 34.

In some embodiments, the disclosure relates generally to a composition comprising a recombinant polymerase homologous to SEQ ID NO: 34 or a biologically active fragment thereof having at least 80% identity to SEQ ID NO: 34 or a biologically active fragment thereof and where the recombinant polymerase comprises a mutation or combination of mutations relative to SEQ ID NO: 34 selected from E397V, L763F, E805I and E745T, and where the polymerase further includes a mutation at one or more of P6N, A77E, A97V, L193V, K240I, R266Q, E267T, L287T, P291T, K292C, E295F or E295N, G418C, L490Q, A502S, S543V, D578E, R593G, L678F or L678T, E713W, V737A, E790G, E794C, and L828A, wherein the numbering is relative to SEQ ID NO: 34.

In some embodiments, the recombinant polymerase homologous to SEQ ID NO: 1 or SEQ ID NO: 34 or the biologically active fragment thereof comprises increased accuracy as compared to a reference polymerase lacking a mutation or combination of mutations relative to SEQ ID NO: 1 or SEQ ID NO: 34; or increased read length as compared to a reference polymerase lacking a mutation or combination of mutations relative to SEQ ID NO: 1 or SEQ ID NO: 34; or increased total sequencing throughput as compared to a reference polymerase lacking a mutation or combination of mutations relative to the recombinant polymerase homologous to SEQ ID NO: 1 or SEQ ID NO: 34; or reduced strand bias as compared to a reference polymerase lacking a mutation or combination of mutations relative to SEQ ID NO: 1 or SEQ ID NO 34. In some embodiments, the increased accuracy, increased read length, increased sequencing throughput or reduced strand bias is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corp., (CA).

In some embodiments, the disclosure relates generally to a composition comprising a polymerase or a biologically active fragment thereof having at least 80% identity to SEQ ID NO: 1 or SEQ ID NO: 34, where the polymerase or biologically active fragment thereof improves sequencing coverage of a GC rich genome, wherein the GC rich genome is at least 60%, 65%, 70%, 75%, 80%, 85% or more GC rich. In some embodiments, the GC rich genome is derived or obtained from a GC rich organism e.g., bacterial genomes such as *Rhodococcus* and the like. In some embodiments, the polymerase or biologically active fragment thereof improves sequencing of a GC rich genome such that upon nucleic acid sequencing the data includes less than 100 nucleic acid gaps per gigabyte of nucleic acid sequencing data. In some embodiments, the polymerase or biologically active fragment thereof having at least 80% identity to SEQ ID NO: 1 or SEQ ID NO: 34 further includes one or more amino acid substitutions relative to SEQ ID NO: 1 or SEQ ID No: 34. In some embodiments, the one or more amino acid substitutions relative to SEQ ID NO: 1 or SEQ ID No: 34 are selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 or L828, wherein the numbering is relative to SEQ ID NO: 1. It will be apparent to one of ordinary skill in the art that any appropriate method to determine GC content is considered sufficient. For example, GC content can be measured by determining the melting temperature of the DNA double helix using spectrophotometry. The absorbance of DNA at 260 nm increases significantly when double-stranded DNA separates to form two single-strands. Other suitable methods to determine GC content include calculating the expected melting temperature using a single GC calculator or using flow cytometry to determine GC ratio's when a large number of samples.

In some embodiments, the disclosure relates generally to a composition comprising a polymerase or a biologically active fragment thereof having at least 80% identity to SEQ ID NO: 1 or SEQ ID NO: 34, where the polymerase or biologically active fragment thereof improves sequencing coverage of a GC rich genome, wherein the GC rich genome is at least 60%, 65%, 70%, 75%, 80%, 85% or more GC rich. In some embodiments, the polymerase or biologically active fragment thereof improves sequencing of a GC rich genome such that upon nucleic acid sequencing the data includes less than 50 nucleic acid gaps per gigabyte of nucleic acid sequencing data. In some embodiments, the polymerase or biologically active fragment thereof having at least 80% identity to SEQ ID NO: 1 or SEQ ID NO: 34 further includes one or more amino acid substitutions relative to SEQ ID NO: 1 or SEQ ID No: 34. In some embodiments, the one or more amino acid substitutions relative to SEQ ID NO: 1 or SEQ ID No: 34 are selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 or L828, wherein the numbering is relative to SEQ ID NO: 1.

In some embodiments, the disclosure relates generally to a composition comprising a polymerase or a biologically active fragment thereof having at least 80% identity to SEQ ID NO: 1 or SEQ ID NO: 34, where the polymerase or biologically active fragment thereof improves sequencing coverage of a GC rich genome, wherein the GC rich genome is at least 60%, 65%, 70%, 75%, 80%, 85% or more GC rich. In some embodiments, the polymerase or biologically active fragment thereof improves sequencing of a GC rich genome such that upon nucleic acid sequencing the data includes less than 20 nucleic acid gaps per gigabyte of nucleic acid sequencing data. In some embodiments, the polymerase or biologically active fragment thereof having at least 80% identity to SEQ ID NO: 1 or SEQ ID NO: 34 further includes one or more amino acid substitutions relative to SEQ ID NO: 1 or SEQ ID No: 34. In some embodiments, the one or more amino acid substitutions relative to SEQ ID NO: 1 or SEQ ID No: 34 are selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 or L828, wherein the numbering is relative to SEQ ID NO: 1.

In some embodiments, the disclosure relates generally to a composition comprising a polymerase or a biologically active fragment thereof having at least 80% identity to SEQ ID NO: 1 or SEQ ID NO: 34, where the polymerase or biologically active fragment thereof improves sequencing coverage of a AT rich genome, wherein the AT rich genome is at least 60%, 65%, 70%, 75%, 80% or more AT rich. In some embodiments, the polymerase or biologically active fragment thereof improves sequencing of an AT rich genome such that upon sequencing the data includes less than 100 nucleic acid gaps per gigabyte of nucleic acid sequencing data. In some embodiments, the polymerase or biologically active fragment thereof having at least 80% identity to SEQ ID NO: 1 or SEQ ID NO: 34 further includes one or more amino acid substitutions relative to SEQ ID NO: 1 or SEQ ID No: 34. In some embodiments, the one or more amino acid substitutions relative to SEQ ID NO: 1 or SEQ ID No: 34 are selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 or L828, wherein the numbering is relative to SEQ ID NO: 1.

In some embodiments, the disclosure relates generally to a composition comprising a polymerase or a biologically active fragment thereof having at least 80% identity to SEQ ID NO: 1 or SEQ ID NO: 34, where the polymerase or biologically active fragment thereof improves sequencing coverage of a AT rich genome, wherein the AT rich genome is at least 60%, 70%, 75% or 80% AT rich. In some embodiments, the polymerase or biologically active fragment thereof improves sequencing of an AT rich genome such that upon sequencing the data includes less than 50 nucleic acid gaps per gigabyte of nucleic acid sequencing data.

In some embodiments, the disclosure relates generally to a composition comprising a polymerase or a biologically active fragment thereof having at least 80% identity to SEQ ID NO: 1 or SEQ ID NO: 34, where the polymerase or biologically active fragment thereof improves sequencing coverage of a AT rich genome, wherein the AT rich genome is at least 60%, 70%, 75% or 80% AT rich. In some embodiments, the polymerase or biologically active fragment thereof improves sequencing of an AT rich genome such that upon sequencing the data includes less than 20 nucleic acid gaps per gigabyte of nucleic acid sequencing data.

In some embodiments, the disclosure relates generally to a method for performing nucleic acid amplification comprising or consisting of contacting a modified polymerase with a nucleic acid template in the presence of one or more nucleotides, where the modified polymerase includes one or more amino acid substitutions relative to SEQ ID NO: 1 or SEQ ID NO: 34 and has an increased accuracy relative to SEQ ID NO: 1 or SEQ ID NO: 34, and polymerizing at least one of the one or more nucleotides using the modified polymerase. In some embodiments, the modified polymerase or the biologically active fragment thereof comprises or consists of at least 150 contiguous amino acid residues having at least 80% identity SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure relates generally to a method for obtaining sequence information from a nucleic acid template comprising providing a reaction mixture including a template nucleic acid hybridized to a sequencing primer and bound to a modified polymerase; contacting the template nucleic acid with at least one type of nucleotide triphosphate, wherein the contacting includes incorporating one or more nucleotides from the at least one type of nucleotide onto the 3' end of the sequencing primer and generating an extended primer product; detecting the presence of the extended primer product in the reaction mixture, thereby determining whether nucleotide incorporation has occurred; and identifying at least one of the one or more nucleotides incorporated from the at least one type of nucleotide. In some embodiments, the method includes a modified polymerase comprising an isolated polypeptide having at least 80% identity to SEQ ID NO: 1 and/or SEQ ID NO: 34, wherein the modified polymerase includes one or more amino acid substitutions selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 or L828, wherein the numbering is relative to SEQ ID NO: 1. In some embodiments, the method can include a modified polymerase comprising an isolated polypeptide having at least 80% identity to SEQ ID NO: 1 and/or SEQ ID NO: 34, wherein the modified polymerase includes one or more amino acid substitutions selected from the group consisting P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I or L828A, wherein the numbering is relative to SEQ ID NO: 1. In some embodiments, the method can include contacting, detecting and identifying steps that are repeated more than once, thereby identifying a plurality of sequential nucleotide incorporations. In some embodiments, the method can include incorporating one or more reversible terminators and/or nucleotide analogs. In some embodiments, the method can include incorporating at least one dNTP (such as dATP, dTTP, dGTP or dCTP).

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIGS. 1A-1E show a graph providing exemplary sequencing throughput and mean read length data obtained using exemplary modified polymerases according to the disclosure.

FIGS. 2A1, 2A2, 2B1, 2B2 area table and a chart providing exemplary nucleic acid sequencing data obtained using exemplary modified polymerases according to the disclosure.

FIGS. 3A-3B are a table providing exemplary nucleic acid sequencing data obtained for modified polymerases obtained according to the disclosure, as compared to a reference polymerase (SEQ ID NO: 34).

FIG. 4 is a table providing exemplary nucleic acid sequencing data with respect to GC content obtained using an exemplary modified polymerase according to the disclosure (SEQ ID NO: 2).

FIG. 6 is a table providing exemplary nucleic acid sequencing data obtained using exemplary modified polymerases according to the disclosure, as compared to a reference polymerase (SEQ ID NO:34).

DETAILED DESCRIPTION

Figure 5A:
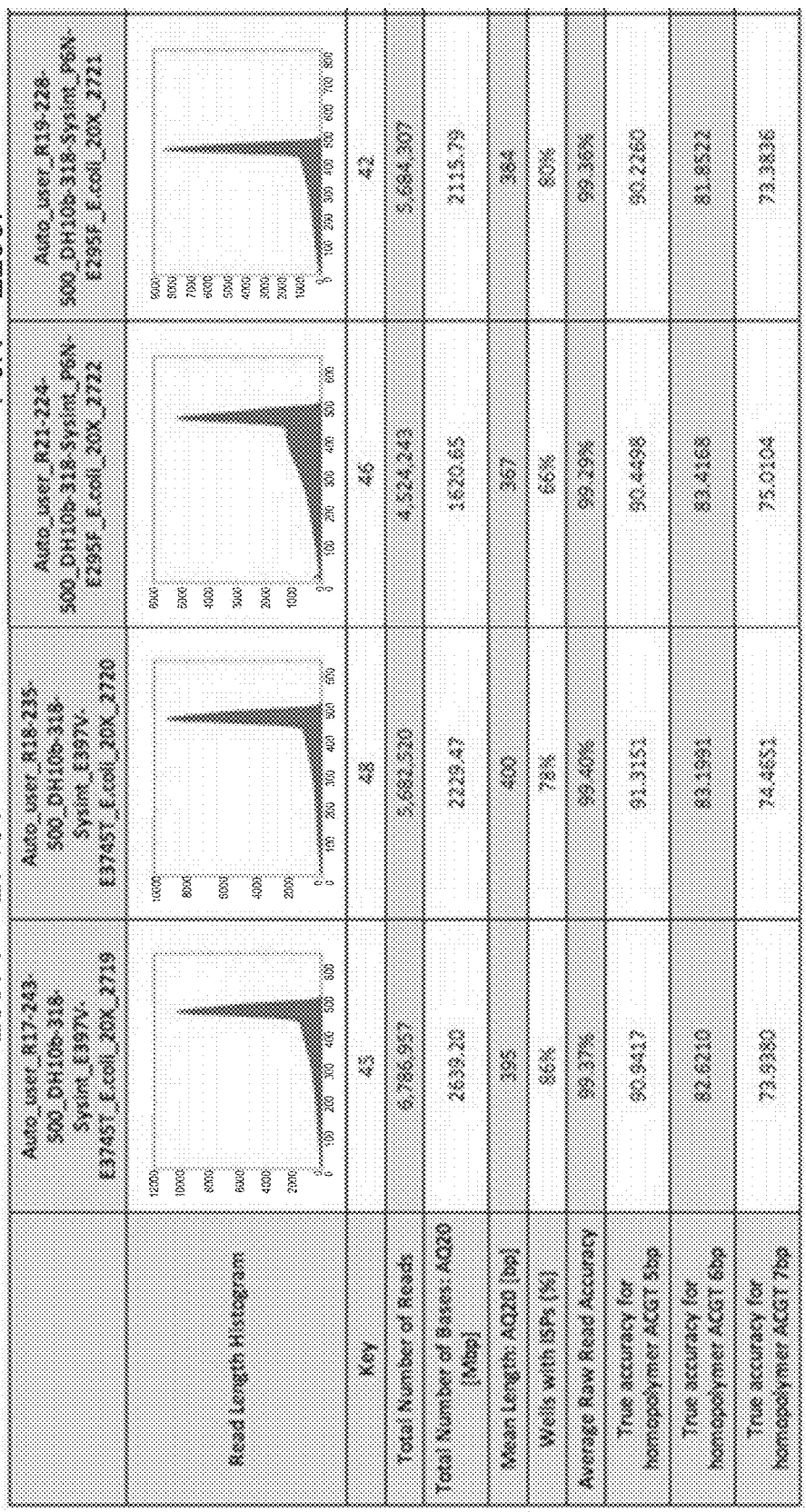
FIGS. 5A-5B are a table and a chart providing exemplary nucleic acid sequencing data obtained using exemplary modified polymerases according to the disclosure, as compared to a reference polymerase (SEQ ID NO:34).

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is explicitly or implicitly set forth herein that is contrary to or otherwise inconsistent with any definition set forth in the patents, patent applications, published applications, and other publications that are herein incorporated by reference, the definition and/or description set forth herein prevails over the definition that is incorporated by reference.

The practice of the disclosure will employ, unless otherwise indicated, conventional techniques of molecular biology, microbiology and recombinant DNA techniques, which are within the skill of the art. Such techniques are explained fully in the literature. See, for example, Sambrook, J., and Russell, D. W., 2001, Molecular Cloning: A Laboratory Manual, Third Edition; Ausubel, F. M., et al., eds., 2002, Short Protocols In Molecular Biology, Fifth Edition.

Note that not all of the activities described in the general description or the examples are required, that a portion of a specific activity may not be required, and that one or more further activities may be performed in addition to those described. Still further, the order in which activities are listed are not necessarily the order in which they are performed.

In some instances, some concepts have been described with reference to specific embodiments. However, one of ordinary skill in the art will appreciate that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprising" (and any form or variant of comprising, such as "comprise" and "comprises"), "having" (and any form or variant of having, such as "have" and "has"), "including" (and any form or variant of including, such as "includes" and "include"), or "containing" (and any form or variant of containing, such as "contains" and "contain"), are inclusive or open-ended and do not exclude additional, unrecited additives, components, integers, elements or method steps. For example, a process, method, article, or apparatus that comprises a list of features is not necessarily limited only to those features but may include other features not expressly listed or inherent to such process, method, article, or apparatus.

Unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Benefits, other advantages, and solutions to problems have been described with regard to specific embodiments. However, such benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features that are, for clarity, described herein in the context of separate embodiments can also be provided in combination in a single embodiment. Conversely, various features that are, for brevity, described in the context of a single embodiment can also be provided separately or in any subcombination. Further, references to values stated in ranges include each and every value within that range.

Also, the use of articles such as "a", "an" or "the" are employed to describe elements and components described herein. This is done merely for convenience and to give a general sense of the scope of the invention. This description should be read to include one or at least one and the singular also includes the plural unless it is obvious that it is meant otherwise. Accordingly, the terms "a," "an," and "the" and similar referents used herein are to be construed to cover both the singular and the plural unless their usage in context indicates otherwise. Accordingly, the use of the word "a" or "an" or "the" when used in the claims or specification, including when used in conjunction with the term "comprising", may mean "one," but it is also consistent with the meaning of "one or more," "at least one," and "one or more than one."

As used herein, the term "polymerase" and its variants comprise any enzyme that can catalyze the polymerization of nucleotides (including analogs thereof) into a nucleic acid strand. Typically, but not necessarily such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, homologs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases, including linking two or more parts from different species or families of polymerases. Typically, the polymerase comprises one or more active sites at which nucleotide binding and/or catalysis of nucleotide polymerization can occur. Some exemplary polymerases include without limitation DNA polymerases (such as for example Phi-29 DNA polymerase, Taq polymerase, reverse transcriptases and *E. coli* DNA polymerase) and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain.

As used herein, the terms "link", "linked", "linkage" and variants thereof comprise any type of fusion, bond, adherence or association that is of sufficient stability to withstand use in the particular biological application of interest. Such linkage can comprise, for example, covalent, ionic, hydrogen, dipole-dipole, hydrophilic, hydrophobic, or affinity bonding, bonds or associations involving van der Waals forces, mechanical bonding, and the like. Optionally, such linkage can occur between a combination of different molecules, including but not limited to: between a nanoparticle and a protein; between a protein and a label; between a linker and a functionalized nanoparticle; between a linker and a protein; between a nucleotide and a label; and the like. Some examples of linkages can be found, for example, in Hermanson, G., *Bioconjugate Techniques*, Second Edition (2008); Aslam, M., Dent, A., *Bioconjugation: Protein Coupling Techniques for the Biomedical Sciences*, London: Macmillan (1998); Aslam, M., Dent, A., *Bioconjugation: Protein Coupling Techniques for the Biomedical Sciences*, London: Macmillan (1998).

The terms "modification" or "modified" and their variants, as used herein with reference to a polypeptide or protein, for example a polymerase, comprise any change in the structural, biological and/or chemical properties of the protein. In some embodiments, the modification can include a change in the amino acid sequence of the protein. For example, the modification can optionally include one or more amino acid mutations, including without limitation amino acid additions, deletions and substitutions (including both conservative and non-conservative substitutions).

The term "conservative" and its variants, as used herein with reference to any change in amino acid sequence, refers to an amino acid mutation wherein one or more amino acids is substituted by another amino acid having highly similar properties. For example, one or more amino acids comprising nonpolar or aliphatic side chains (for example, glycine, alanine, valine, leucine, or isoleucine) can be substituted for each other. Similarly, one or more amino acids comprising polar, uncharged side chains (for example, serine, threonine, cysteine, methionine, asparagine or glutamine) can be substituted for each other. Similarly, one or more amino acids comprising aromatic side chains (for example, phenylalanine, tyrosine or tryptophan) can be substituted for each other. Similarly, one or more amino acids comprising positively charged side chains (for example, lysine, arginine or histidine) can be substituted for each other. Similarly, one or more amino acids comprising negatively charged side chains (for example, aspartic acid or glutamic acid) can be substituted for each other. In some embodiments, the modified polymerase or biologically active fragment thereof is a variant that comprises one or more of these conservative amino acid substitutions, or any combination thereof. In some embodiments, conservative substitutions for leucine include: alanine, isoleucine, valine, phenylalanine, tryptophan, methionine, and cysteine. In other embodiments, conservative substitutions for asparagine include: arginine, lysine, aspartate, glutamate, and glutamine.

Throughout this disclosure, various amino acid mutations, including, for example, amino acid substitutions are referenced using the amino acid single letter code, and indicating the position of the residue within a reference amino acid sequence. In the case of amino acid substitutions, the identity of the substituent is also indicated using the amino acid single letter code. For example, a reference to the hypothetical amino acid substitution "E397V, wherein the numbering is relative to the amino acid sequence of SEQ ID NO: 1" indicates an amino acid substitution wherein an Valine (V) residue is substituted for the normally occurring glutamic acid (E) residue at amino acid position 397 of the amino acid sequence of SEQ ID NO: 1. Some of the amino acid sequences disclosed herein begin with a methionine residue ("M"), which is typically introduced at the beginning of nucleic acid sequences encoding peptides desired to be expressed in bacterial host cells. However, it is to be understood that the disclosure also encompasses all such amino acid sequences beginning from the second amino acid residue onwards, without the inclusion of the first methionine residue.

As used herein, the terms "identical" or "percent identity," and their variants, when used in the context of two or more nucleic acid or polypeptide sequences, refer to two or more sequences (or subsequences such as biologically active fragments) that are the same or have a specified percentage of amino acid residues or nucleotides that are the same, when compared and aligned for maximum correspondence, as measured using any one or more of the following sequence comparison algorithms: Needleman-Wunsch (see, e.g., Needleman, Saul B.; and Wunsch, Christian D. (1970). "*A general method applicable to the search for similarities in the amino acid sequence of two proteins*" *Journal of Molecular Biology* 48 (3):443-53); Smith-Waterman (see, e.g., Smith, Temple F.; and Waterman, Michael S., "*Identification of Common Molecular Subsequences*" (1981) *Journal of Molecular Biology* 147:195-197); or BLAST (Basic Local Alignment Search Tool; see, e.g., Altschul S F, Gish W, Miller W, Myers E W, Lipman D J, "*Basic local alignment search tool*" (1990) *J Mol Biol* 215 (3):403-410).

As used herein, the terms "identical" or "identity", and their variants, when used in the context of two or more nucleic acid or polypeptide sequences, refer to two or more sequences or subsequences (such as biologically active fragments) that have at least 60%, at least 70%, at least 75%, at least 80%, at least 85%, at least 90%, at least 95%, at least 96%, at least 97%, at least 98%, or at least 99% nucleotide or amino acid residue identity, when compared and aligned for maximum correspondence, as measured using a sequence comparison algorithm or by visual inspection. Substantially identical sequences are typically considered to be "homologous" without reference to actual ancestry.

Proteins and/or protein subsequences (such as biologically active fragments) are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or biologically active fragments or sequences thereof). The precise percentage of similarity between sequences that is useful in establishing homology varies with the nucleic acid and protein at issue, but as little as 25% sequence similarity over 25, 50, 100, 150, or more nucleic acids or amino acid residues, is routinely used to establish homology. Higher levels of sequence similarity, e.g., 50%, 60%, 70%, 80%, 85%, 90%, 95%, 98% or 99%, can also be used to establish homology.

Methods for determining sequence similarity percentages (e.g., BLASTP and BLASTN using default parameters) are described herein and are generally available. For sequence comparison and homology determination, typically one sequence acts as a reference sequence to which test sequences are compared. Generally, when using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2004).

One example of an algorithm that is suitable for determining percent sequence identity and sequence similarity (homology) is the BLAST algorithm, which is described in Altschul et al., *J Mol. Biol.* 215:403-410 (1990). Software for performing BLAST analyses is publicly available through the National Center for Biotechnology Information. This algorithm involves first identifying high scoring sequence pairs (HSPs) by identifying short words of length "W" in the query sequence, which either match or satisfy some positive-valued threshold score "T" when aligned with a word of the same length in a database sequence. "T" is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (reward score for a pair of matching residues; always >0) and "N" (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters "W", "T", and "X" determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

The term "primer extension activity" and its variants, as used herein, when used in reference to a given polymerase, comprise any in vivo or in vitro enzymatic activity characteristic of a given polymerase that relates to catalyzing nucleotide incorporation onto the terminal 3'OH end of an extending nucleic acid molecule. Typically, but not necessarily such nucleotide incorporation occurs in a template-dependent fashion. In some embodiments, the primer extension activity of a given polymerase can be quantified as the total number of nucleotides incorporated (as measured by, e.g., radiometric or other suitable assay) by a unit amount of polymerase (in moles) per unit time (seconds) under a particular set of reaction conditions.

The term "thermostability" and its variants, as used herein, when used in reference to a given polymerase, comprise any in vivo or in vitro enzymatic activity characteristic of a given polymerase that relates to catalyzing nucleotide incorporation at moderately high temperature without the loss of properties that relate to catalyzing nucleotide incorporation. Typically, but not necessarily, such nucleotide incorporation occurs in a template-dependent fashion. In some embodiments, the thermostability of a given polymerase can be quantified as the total number of nucleotides incorporated (as measured by, e.g., radiometric or other suitable assay) by a unit amount of polymerase (in moles) per unit time (minute) at a given temperature (° C. or ° F.). In some embodiments, the thermostability of a given polymerase can be quantified by measuring polymerization activity by a unit amount of polymerase (in moles) after incubation at 95° C. for 40 minutes. In one embodiment, the thermostability of a given polymerase can be quantified by measuring polymerization activity based on the half-life of the polymerase. For example, Taq has a half-life of greater than 2 hours at 92.5° C.; 40 minutes at 95° C., and 9 minutes at 97.5° C. (Lawyer et al., (1993) *PCR Methods Appl.*, 2 (4) 275-87. Some of the examples described herein compare the relative amounts of nucleotide polymerization of a reference polymerase to a modified polymerase (e.g., nucleotide polymerization using SEQ ID NO: 1 as compared to nucleotide polymerization using SEQ ID NO: 2). In these examples, the nucleotide polymerization properties of the reference polymerase and the modified polymerase (or biologically active fragment thereof) are assessed under identical conditions that include elevated temperatures, such as, 95° C., 96° C., or 97° C. for various times such as 2 minutes, 4 minutes, 6 minutes or 8 minutes (See e.g. Example 10, FIGS. 11-14) before performing a PCR reaction using the polymerase.

Thermostable polymerases generally have an optimal effect at about 70° C. (for *Thermus aquaticus* (Taq), it is 74° C. and Taq demonstrates insertion of approximately 2800 nucleotides/min at 70° C., 1400 nucleotides/min at 55° C., 90 nucleotides/min at 37° C. and about 15 nucleotides/min at 22° C.). Polymerases from *Pyrococcus furiosus* (Pfu), *Pyrococcus woesei* (Pwo), *Thermatoga maritima* (Tma) and *Thermococcus Litoralis* (Tli or Vent) are also encompassed within the scope of the present disclosure. These polymerases demonstrate substantially higher temperature stability than *Thermus aquaticus* (Taq).

The term "accuracy" and its variants, as used herein (such as "raw read accuracy") when used in reference to a given polymerase, comprises the longest perfect read (typically measured in terms of the number of nucleotides correctly included in the read) obtained from a nucleotide polymerization reaction. Accordingly, average read accuracy, as used herein, when referring to a given polymerase refers to the "average" perfect read obtained from a nucleotide polymerization reaction.

The term "DNA binding activity" and its variants, as used herein, when used in reference to a given polymerase, comprise any in vivo or in vitro enzymatic activity characteristic of a given polymerase that relates to interaction of the polymerase with a DNA sequence in a recognition-based manner. Typically, but not necessarily such interaction includes binding of the polymerase, and more specifically binding of the DNA-binding domain of the polymerase, to the recognized DNA sequence. In some embodiments, recognition includes binding of the polymerase to a sequence-specific or non-sequence specific DNA sequence. In some embodiments, the DNA binding activity of a given polymerase can be quantified as the affinity of the polymerase to recognize and bind to the recognized DNA sequence. For example, DNA binding activity can be monitored and determined using an anistrophy signal change (or other suitable assay) as a protein-DNA complex is formed under a particular set of reaction conditions.

As used herein, the term "biologically active fragment" and its variants, when used in reference to a given biomolecule, refers to any fragment, derivative, homolog or analog of the biomolecule that possesses an in vivo or in vitro activity that is characteristic of the biomolecule itself. For example, a polymerase can be characterized by various biological activities, for example DNA binding activity, nucleotide polymerization activity, primer extension activity, strand displacement activity, reverse transcriptase activity, nick-initiated polymerase activity, 3'-5' exonuclease (proofreading) activity, thermostability, accuracy, processivity, and the like. In some embodiments, a "biologically active fragment" of a polymerase is any fragment, derivative, homolog or analog of the polymerase that can catalyze the polymerization of nucleotides (including homologs and analogs thereof) into a nucleic acid strand. In some embodiments, the biologically active fragment, derivative, homolog or analog of the polymerase possesses 10%, 20%, 30%, 40%, 50%, 60%, 70%, 75%, 80%, 85%, 90% 95%, or 98% or greater of the biological activity of the polymerase in any in vivo or in vitro assay of interest such as, for example, DNA binding assays, nucleotide polymerization assays (which may be template-dependent or template-independent), primer extension assays, strand displacement assays, reverse transcriptase assays, proofreading assays, accuracy assays, thermostability assays and the like.

In some embodiments, the biological activity of a polymerase fragment is assayed by measuring the primer extension activity in vitro of the fragment under defined reaction conditions. In some embodiments, the biological activity of a polymerase fragment is assayed by measuring the polymerization activity in vitro of the fragment under defined reaction conditions. In some embodiments, the biological activity of a polymerase fragment is assayed by measuring the thermostability in vitro of the fragment under defined reaction conditions. In some embodiments, the biological activity of a polymerase fragment is assayed by measuring the accuracy in vitro of the fragment under defined reaction conditions. In some embodiments, the biological activity of a polymerase fragment is assayed by measuring the processivity in vitro of the fragment under defined reaction conditions. In some embodiments, the biological activity of a polymerase fragment is assayed by measuring the strand displacement activity in vitro of the fragment under defined reaction conditions. In some embodiments, the biological activity of a polymerase fragment is assayed by measuring the read-length activity in vitro of the fragment under defined reaction conditions. In some embodiments, the biological activity of a polymerase fragment is assayed by measuring the strand bias activity in vitro of the fragment under defined reaction conditions. In some embodiments, the biological activity of a polymerase fragment is assayed by measuring the proofreading activity in vitro of the fragment under defined reaction conditions. In some embodiments, the biological activity of a polymerase fragment is assayed by measuring the output of an in vitro assay such as sequencing throughput or average read length as performed by the polymerase fragment under defined reaction conditions. In some embodiments, the biological activity of a polymerase fragment is assayed by measuring the output of a nucleotide polymerization reaction in vitro such as raw accuracy of the polymerase fragment to incorporate correct Watson-Crick nucleotides in the nucleotide polymerization reaction under defined reaction conditions. In some embodiments, the biologically active fragment of a polymerase can include measuring the biological activity of any one or more of the polymerase biological activities outlined herein.

In some embodiments, a biologically active fragment can include any part of the DNA binding domain or any part of the catalytic domain of the modified polymerase. In some embodiments, the biologically active fragment can optionally include any 25, 50, 75, 100, 150 or more contiguous amino acid residues of the DNA binding or catalytic domain. In some embodiments, a biologically active fragment of the modified polymerase can include at least 25 contiguous amino acid residues of the catalytic domain or the DNA binding domain having at least 80%, 85%, 90%, 95%, 98%, or 99% identity to any one or more of the polymerases encompassed by the disclosure. In some embodiments, a biologically active fragment of a modified polymerase can include at least 25 contiguous amino acid residues of the catalytic domain or the DNA binding domain having at least 80%, 85%, 90%, 95%, 98%, or 99% identity to any one or more of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33.

Biologically active fragments can optionally exist in vivo, such as, for example, fragments which arise from post transcriptional processing or which arise from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, insect or mammalian cells.

In some embodiments, the disclosure relates generally to not only the specific polymerases disclosed herein, but also to any biologically active fragment of such polymerases, which are encompassed within the scope of the present disclosure. In some embodiments, a biologically active fragment of any polymerase of the disclosure includes any fragment that exhibits primer extension activity in vitro. In some embodiments, a biologically active fragment of any polymerase of the disclosure includes any fragment that exhibits DNA binding activity in vitro. In some embodiments, a biologically active fragment of any polymerase of the disclosure includes any fragment that retains polymerase activity in vitro. Polymerase activity can be determined by any method known in art. For example, determination of polymerase activity can be based on the activity of extending a primer on a template.

In some embodiments, the disclosure generally relates to a modified polymerase having one or more amino acid mutations (such as a deletion, substitution or addition) relative to a reference polymerase lacking the one or more amino acid mutations, and wherein the modified polymerase retains polymerase activity in vitro or exhibits primer extension activity in vitro. In some embodiments, the modified polymerase includes any biologically active fragment of such polymerase that retains processivity in vitro or exhibits thermostability activity in vitro.

In some embodiments, the disclosure generally relates to a modified polymerase having one or more amino acid mutations (such as a deletion, substitution or addition) relative to a reference polymerase lacking the one or more amino acid mutations, and wherein the modified polymerase retains proofreading activity in vitro. Determination of whether a polymerase exhibits exonuclease activity or exhibits reduced exonuclease activity, can be readily determined by standard methods. For example, polynucleotides can be synthesized such that a detectable proportion of the nucleotides are radioactively labeled. These polynucleotides can be incubated in an appropriate buffer in the presence of the polypeptide to be tested. After incubation, the polynucleotide is precipitated and exonuclease activity is detectable as radioactive counts due to free nucleotides in the supernatant. As will be appreciated by the skilled artisan, an appropriate polymerase or biologically active fragment may be selected from those described herein based on any of the above biological activities, or combinations thereof, depending on the application of interest.

As used herein, the term "nucleotide" and its variants comprise any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally-occurring nucleotides but also any analogs, regardless of their structure, that can bind selectively to, or can be polymerized by, a polymerase. While naturally-occurring nucleotides typically comprise base, sugar and phosphate moieties, the nucleotides of the disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. Some examples of nucleotide analogs are described in Xu, U.S. Pat. No. 7,405,281. In some embodiments, the nucleotide comprises a label (e.g., reporter moiety) and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group or substitute phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

As used herein, the term "nucleotide incorporation" and its variants comprise polymerization of one or more nucleotides to form a nucleic acid strand including at least two nucleotides linked to each other, typically but not necessarily via phosphodiester bonds, although alternative linkages may be possible in the context of particular nucleotide analogs.

As used herein, the term "processivity" and its variants comprise the ability of a polymerase to remain bound to a single primer/template hybrid. The term processivity as used herein, when used in reference to a given polymerase, comprises the number of nucleotides that a polymerase attaches to the 3' end of a nucleic acid (e.g., the 3'-OH group of a DNA strand) in a single cycle. This number represents the rate of polymerization and the dissociation constant ($K_d$) of the polymerase. In some embodiments, processivity can be measured by the number of nucleotides that a polymerase incorporates into a nucleic acid (such as a sequencing primer) prior to dissociation of the polymerase from the primer/template hybrid. In some embodiments, the polymerase has a processivity of at least 100 nucleotides, although in other embodiments it has a processivity of at least 200 nucleotides, at least 300 nucleotides, at least 400 nucleotides, at least 500 nucleotides or greater. It will be understood by those of ordinary skill in the art that the higher the processivity of the polymerase, the more nucleotides that can be incorporated prior to dissociation and therefore the longer the sequence (read-length) that can be obtained. In other words, polymerases having low processivity will typically provide shorter average read-lengths than will polymerases having higher processivity. In one embodiment, polymerases of the instant disclosure containing one or more amino acid mutations can possess improved processivity as compared to a polymerase lacking the one or more amino acid mutations In one exemplary assay, the processivity of a given polymerase can be measured by incubating the polymerase with a primer:template duplex under nucleotide incorporation conditions, and resolving the resulting primer extension products using any suitable method, for example via gel electrophoresis. The primer can optionally include a label to enhance detectability of the primer extension products. The nucleotide incorporation reaction mixture typically includes a vast excess of unlabeled competitor template, thereby ensuring that virtually all of the extension products are produced through a single template binding event. Following such resolution, the average amount of full-length extension products can be quantified using any suitable means, including fluorimetric or radiometric detection of full-length extension products. To compare the processivity of two or more different enzymes (e.g., reference and modified polymerases), each enzyme can be employed in a parallel and separate reaction, following which the resulting full-length primer extension products can be resolved and measured, and such measurements compared.

In other exemplary embodiments, the processivity of a given polymerase can be measured using any suitable assay known in the art, including but not limited to the assays described in Von Hippel, P. H., Faireld, F. R. and Dolejsi, M. K., *On the processivity of polymerases*, Ann. NY Acad. Sci., 726:118-131 (1994); Bambara, R. A., Uyemura, D. and Choi, T., *On the processive mechanism of Escherichia coli DNA polymerase I Quantitative assessment of processivity*, J. Biol. Chem., 253:413-423 (1978); Das, S. K. and Fujimura, R. K., *Processiveness of DNA polymerases. A comparative study using a simple procedure*, J. Biol. Chem., 254: 1227-1232 (1979); Nasir, M. S. and Jolley, M. E., *Fluorescence polarization: An Analytical Tool for Immunoassay and Drug Discovery*, Combinational Chemistry and High Throughput Screening, 2:177-190 (1999); Mestas, S. P., Sholders, A. J., and Peersen, O. B., *A Fluorescence Polarization Based Screening Assay for Nucleic Acid Polymerase Elongation Activity*, Anal. Biochem., 365:194-200 (2007); Nikiforov, T. T., *Fluorogenic polymerase, endonuclease, and ligase assays based on DNA substrates labeled with a single fluorophore*, Analytical Biochemistry 412: 229-236; and Yan Wang, Dennis E. Prosen, Li Mei, John C. Sullivan, Michael Finney and Peter B. Vander Horn, Nucleic Acids Research, 32(3):1197-1207 (2004).

The terms "read length" or "read-length" and their variants, as used herein, refer to the number of nucleotides that are polymerized (or incorporated into an existing nucleic acid strand) in a template-dependent manner by a polymerase prior to dissociation from a template nucleic acid strand. In some embodiments, a polymerase that dissociates from the template nucleic acid strand after five incorporations will typically provide a sequence having a read length of 5 nucleotides, while a polymerase that dissociates from the template nucleic acid strand after 500 nucleotide incorporations will typically provide a sequence having a read length of about 500 nucleotides. While the actual or absolute processivity of a given polymerase (or the actual read length of polymerization products produced by the polymerase) can vary from reaction to reaction (or even within a single reaction mixture wherein the polymerase produces different products having different read lengths), the polymerase can be characterized by the average processivity (or average read length of polymerization products) observed under a defined set of reaction conditions. The "error-free read length" comprises the number of nucleotides that are consecutively and contiguously incorporated without error (i.e., without mismatch and/or deviation from an established and predictable set of base pairing rules) into the newly synthesized nucleic acid strand.

The terms "systematic error" or "SE" and its variants, as used herein, refers to the percentage of errors present in a sequence motif containing a homopolymer of a defined length, with systematic deletion occurring on the nucleic acid strand at a specified minimum frequency, and with sequencing coverage occurring at a specified minimum frequency. For example, in some embodiments the systematic error can be measured as the percentage of errors in sequence motifs containing homopolymers of length 1-6, with systematic deletion occurring on strand with a frequency greater than 15%, when coverage (of the sequencing run) is equal to or greater than 20×. In some embodiments, the systematic error is estimated as the percentage of stochastic errors in sequence motifs containing homopolymers of length 1-6, with systematic deletion occurring on strand with a frequency greater than 15%, when coverage (of the sequencing run) is equal to or greater than 20×; such embodiments are the focus of several of the working examples disclosed herein. In some embodiments, the percentage of systematic error is lowered when using a modified polymerase as disclosed herein as compared to a reference polymerase (e.g., a wild-type Taq polymerase) that does not contain one or more amino acid modifications. While the actual systematic error of a given polymerase can vary from reaction to reaction (or even within a single reaction mixture) the polymerase can be characterized by the percentage systematic error observed under a defined set of reaction conditions. In some embodiments, the modified polymerases of the instant application have a lowered systematic error percentage as compared to a corresponding reference polymerase not having the one or more amino acid modifications. In some embodiments, the modified polymerase, as disclosed herein, contains a systematic error percentage of less than 3%. In some embodiments, the modified polymerase, as disclosed herein, contain a systematic error percentage of less than 1%. In some embodiments, the modified polymerases as disclosed herein contain a systematic error percentage of less than 0.9%. In some embodiments, the modified polymerases as disclosed herein contain a systematic error percentage of less than 0.8%. In some embodiments, the modified polymerases as disclosed herein contain a systematic error percentage of less than 0.7%. In some embodiments, the modified polymerases as disclosed herein contain a systematic error percentage of less than 0.6%. In some embodiments, the modified polymerases as disclosed herein contain a systematic error percentage of less than 0.5%. In some embodiments, the modified polymerases as disclosed herein contain a systematic error percentage of less than 0.4%. In some embodiments, the modified polymerases as disclosed herein contain a systematic error percentage of less than 0.3%. In some embodiments, the modified polymerases as disclosed herein contain a systematic error percentage of less than 0.2%. In some embodiments, the modified polymerases as disclosed herein contain a systematic error percentage of less than 0.1%. In some embodiments, the modified polymerases as disclosed herein contain a systematic error percentage of less than 0.09%. In some embodiments, the modified polymerases as disclosed herein contain a systematic error percentage of less than 0.08%. In some embodiments, the modified polymerases as disclosed herein contain a systematic error percentage of less than 0.05%. In some embodiments, the modified polymerases as disclosed herein contain a systematic error percentage of less than 0.04%.

The term "strand bias" as used herein, refers to the percentage of target bases in a sequencing run where the read (genotype) from one strand (e.g., positive strand) is different from the read (genotype) inferred from the other (e.g., negative) strand. The coverage of a given target base can be computed by counting the number of read bases mapped to it in an alignment. The mean coverage can be computed by averaging this value across every base in the target. Then, the relative coverage for a particular base can be computed as the ratio of these values. A relative coverage of 1 indicates that a particular base is covered at the expected average rate. A relative coverage above 1 indicates higher than expected coverage and below 1 indicates lower than expected coverage. Generally, the probability of ambiguous mapping increases as reads become shorter or less accurate. Ambiguous mapping is also more likely for reads that derive from repetitive or low complexity regions of the genome, including some regions with extreme (high) GC content. In some embodiments, the percentage of strand bias is lowered or reduced when using a modified polymerase as disclosed herein, as compared to a reference polymerase (e.g., a wild-type Taq polymerase) that does not contain the corresponding one or more amino acid modifications. In some embodiments, the modified polymerases of the instant application have a decreased (reduced) strand bias as compared to the corresponding non-modified polymerase. While the actual strand bias of a given polymerase can vary from reaction to reaction (or even within a single reaction mixture) the polymerase can be characterized by the percentage of target bases with no strand bias, observed under a defined set of reaction conditions.

In some embodiments, the modified polymerases as disclosed herein comprise a percentage of target bases with no strand bias of above 25%. In some embodiments, the modified polymerases as disclosed herein comprise a percentage of target bases with no strand bias of about 30%. In some embodiments, the modified polymerases as disclosed herein comprise a percentage of target bases with no strand bias of about 40%. In some embodiments, the modified polymerases as disclosed herein comprise a percentage of target bases with no strand bias of about 45%. In some embodiments, the modified polymerases as disclosed herein comprise a percentage of target bases with no strand bias of about 50%. In some embodiments, the modified polymerases as disclosed herein comprise a percentage of target bases with no strand bias of about 60%. In some embodiments, the modified polymerases as disclosed herein comprise a percentage of target bases with no strand bias of about 70%. In some embodiments, the modified polymerases as disclosed herein comprise a percentage of target bases with no strand bias of about 75%. In some embodiments, the modified polymerases as disclosed herein comprise a percentage of target bases with no strand bias of about 80%. In some embodiments, the modified polymerases as disclosed herein comprise a percentage of target bases with no strand bias of about 85%. Conversely, in some embodiments the modified polymerases as disclosed herein can include about 15% percent of target bases with strand bias. In another embodiment, the modified polymerases as disclosed herein can include about 20%, 25%, 30%, 35%, 40%, 45% or 50% percent of target bases with strand bias.

The terms "signal to noise ratio" or "SNR" refer to the ratio of signal power to noise power. Generally, SNR is a method of measuring a desired signal compared to the level of background noise. In some embodiments, "signal to noise ratio" can refer to the ratio of signal power obtained during a sequencing run as compared to background noise of the same sequencing run. In some embodiments, the instant application discloses methods, kits, apparatuses, and compositions that provide a means to increase the signal to noise ratio. In some embodiments, the disclosure relates generally to a method for performing nucleic acid sequencing comprising contacting a modified polymerase with a nucleic acid template in the presence of one or more nucleotides, where the modified polymerase includes one or more amino acid modifications (e.g., a substitution) relative to a reference polymerase and has an increased signal to noise ratio relative to the reference polymerase not having the one or more amino acid modifications, and polymerizing at least one of the one or more nucleotides using the modified polymerase.

In some embodiments, the disclosure relates generally to compositions, methods, systems, apparatuses and kits comprising modified polymerases that are characterized by increased processivity, increased read length (including error-free read length), increased total sequencing throughput, improved thermostability and/or increased accuracy as compared to their unmodified counterpart (e.g., a reference polymerase), as well as to methods for making and using such modified polymerases in a wide range of biological and chemical reactions such as nucleotide polymerization, primer extension, generation of nucleic acid libraries and nucleic acid sequencing reactions.

In some embodiments, the disclosure relates generally to compositions, methods, systems, apparatuses and kits comprising modified polymerases that are characterized by decreased strand bias and/or reduced systematic error as compared to their unmodified counterparts (e.g., a reference polymerase), as well as to methods for making and using such modified polymerases in a wide range of biological and chemical reactions such as nucleotide polymerization, primer extension, generation of nucleic acid libraries and nucleic acid sequencing reactions.

In some embodiments, the modified polymerases encompassed within the scope of the present disclosure include one or more amino acid mutations (e.g., amino acid substitutions, additions or deletions) relative to the corresponding counterpart lacking the identical mutation(s). In some embodiments, the term "accuracy" as used herein can be measured by determining the rate of incorporation of a correct nucleotide during polymerization as compared to the rate of incorporation of an incorrect nucleotide during polymerization. In some embodiments, the rate of incorporation of an incorrect nucleotide can be greater than 0.3, 0.4, 0.5, 0.6, 0.7 seconds or more under elevated salt conditions (e.g., high ionic strength solution) as compared to standard (low ionic strength solution) salt conditions. While not wishing to be bound by any particular theory, it has been found by the applicants that the presence of elevated salt during polymerization slows down the rate of incorrect nucleotide incorporation, thereby producing a slower incorporation constant for the incorrect nucleotide. In some embodiments, a modified polymerase of the disclosure has enhanced accuracy compared to a reference polymerase lacking the corresponding mutation; optionally the modified polymerase or a biological fragment thereof has enhanced accuracy (as compared to a reference polymerase lacking the corresponding amino acid mutation) in the presence of a high ionic strength solution. Generally, a standard ionic strength solution, as used herein, refers to an ionic solution having less than 120 mM salt. In another embodiment, a standard ionic strength solution as used herein refers to an ionic solution having less than 100 mM salt.

In some embodiments, the disclosure relates generally to a modified polymerase that retains polymerase activity and/or primer extension activity in the presence of a high ionic strength solution. In some embodiments, a high ionic strength solution can be at least 120 mM salt concentration. In some embodiments, the high ionic strength solution is 125 mM to 200 mM salt concentration. In some embodiments, the salt can include a potassium and/or sodium salt, such as KCl and/or NaCl. It will be apparent to the skilled artisan that various other suitable salts can be used in place, or in combination with KCl and/or NaCl. In some embodiments, the ionic strength solution can further include a sulfate.

In some embodiments, the modified polymerase can amplify and/or sequence a nucleic acid molecule in the presence of a high ionic strength solution. In some embodiments, a modified polymerase is capable of amplifying (and/or sequencing) a nucleic acid molecule in the presence of a high ionic strength solution to a greater extent (for example as measured by "accuracy") than a reference polymerase lacking one or more of the corresponding mutations (or homologous mutations) under identical conditions. In some embodiments, a modified polymerase is capable of amplifying (and/or sequencing) a nucleic acid molecule in the presence of a high ionic strength solution to a greater capacity (for example as measured by "accuracy") than a reference polymerase lacking one or more of the mutations (or homologous mutations) under standard ionic strength conditions (i.e., low ionic strength as compared to a high ionic strength solution).

In some embodiments, the disclosure generally relates to a modified polymerase or a biologically active fragment thereof that can perform nucleotide polymerization or nucleotide incorporation in the presence of high ionic strength conditions as compared to a reference polymerase under the same conditions.

In some embodiments, the disclosure generally relates to a modified polymerase or a biologically active fragment thereof that has increased accuracy or increased processivity in the presence of high ionic strength conditions as compared to a reference polymerase under the same conditions.

In some embodiments, the disclosure generally relates to a modified polymerase or a biologically fragment thereof that can detect a change in ion concentration during nucleotide polymerization in the presence of a high ionic strength salt conditions as compared to a reference polymerase under the same conditions.

In some embodiments, the disclosure generally relates to a modified polymerase or a biologically active fragment thereof that can amplify or sequence a nucleic acid molecule in the presence of a high ionic strength solution.

In some embodiments, the disclosure generally relates to a modified polymerase or a biologically active fragment thereof that has increased accuracy as compared to a reference polymerase under the same conditions.

In some embodiments, the disclosure relates generally to methods, compositions, systems and kits comprising the use of such modified polymerases in nucleotide polymerization reactions, including nucleotide polymerization reactions wherein sequence information is obtained from a nucleic acid molecule. In some embodiments, the disclosure relates generally to methods, compositions, systems and kits comprising the use of such modified polymerases in clonal amplification reactions, including nucleic acid library synthesis. In some embodiments, the disclosure relates to methods for using such modified polymerases in ion-based nucleic acid sequencing reactions, where sequence information is obtained from a template nucleic acid using the ion-based sequencing system. In some embodiments, the disclosure relates generally to compositions, methods, systems, kits and apparatuses for carrying out a plurality of label-free DNA sequencing reactions (e.g., ion-based sequencing reactions) using a large-scale array of electronic sensors, for example field effect transistors ("FETs").

In some embodiments, the disclosure relates generally to compositions (as well as related methods, systems, kits and apparatuses using such compositions) comprising a modified polymerase including at least one amino acid modification (e.g., amino acid substitution, addition, deletion or chemical modification) relative to a reference polymerase (where the reference polymerase does not include the at least one amino acid modification), where the modified polymerase is optionally characterized by a change (e.g., increase or decrease) in any one or more of the following properties relative to the reference polymerase: thermostability, read length, accuracy, strand bias, systematic error, total sequencing throughput, performance in salt (i.e., ionic strength) and processivity.

As used herein, the terms "Q17" or "Q20" and their variants, when used in reference to a given polymerase, refer to certain aspects of polymerase performance, particularly accuracy, in a given polymerase reaction, for example in a polymerase-based sequencing by synthesis reaction. For example, in a particular sequencing reaction, accuracy metrics can be calculated either through prediction algorithms or through actual alignment to a known reference genome. Predicted quality scores ("Q scores") can be derived from algorithms that look at the inherent properties of the input signal and make fairly accurate estimates regarding if a given single base included in the sequencing "read" will align. In some embodiments, such predicted quality scores can be useful to filter and remove lower quality reads prior to downstream alignment. In some embodiments, the accuracy can be reported in terms of a Phred-like Q score that measures accuracy on logarithmic scale such that: Q10=90%, Q17=98%, Q20=99%, Q30=99.9%, Q40=99.99%, and Q50=99.999%. Phred quality scores ("Q") are defined as a property which is logarithmically related to the base-calling error probabilities ("P"). Often the formula given for calculating "Q" is $Q=10*\log^{10}(1/\text{error rate})$. In some embodiments, the data obtained from a given polymerase reaction can be filtered to measure only polymerase reads measuring "N" nucleotides or longer and having a Q score that passes a certain threshold, e.g., Q10, Q17, Q100 (referred to herein as the "NQ17" score). For example, the 100Q20 score can indicate the number of reads obtained from a given reaction that are at least 100 nucleotides in length and have Q scores of Q20 (99%) or greater. Similarly, the 200Q20 score can indicate the number of reads that are at least 200 nucleotides in length and have Q scores of Q20 (99%) or greater.

In some embodiments, accuracy can also be calculated based on proper alignment using a reference genomic sequence, referred to herein as the "raw" accuracy. This is single pass accuracy, involving measurement of the "true" per base error associated with a single read, as opposed to consensus accuracy, which measures the error rate from the consensus sequence which is the result of multiple reads. Raw accuracy measurements can be reported in terms of "AQ" scores (for aligned quality). In some embodiments, the data obtained from a given polymerase reaction can be filtered to measure only polymerase reads measuring "N" nucleotides or longer having a AQ score that passes a certain threshold, e.g., AQ10, AQ17, AQ100 (referred to herein as the "NAQ17" score). For example, the 100AQ20 score can indicate the number of reads obtained from a given polymerase reaction that are at least 100 nucleotides in length and have AQ scores of AQ20 (99%) or greater. Similarly, the 200AQ20 score can indicate the number of reads that are at least 200 nucleotides in length and have AQ scores of AQ20 (99%) or greater.

In some embodiments, the accuracy of the polymerase (including for example accuracy in a given sequencing reaction) can be measured in terms of the total number of "perfect" (i.e., zero-error) reads obtained from a polymerase reaction that are greater than 100, 200, 300, 400, 500, 750, 1000, 5000, 10000, 100000 nucleotides in length.

In some embodiments, the accuracy of the polymerase can be measured in terms of the longest perfect read (typically measured in terms of number of nucleotides included in the read) that is obtained from a polymerase reaction.

In some embodiments, the accuracy of the polymerase can be measured in terms of fold-increase in sequencing throughput obtained in a given sequencing reaction. For example, in some embodiments an exemplary modified polymerase encompassed by the scope of the present disclosure may have an increased accuracy of 2-fold, 5-fold, 10-fold, 20-fold, 50-fold, 75-fold, 100-fold, 150-fold, 200-fold, 400-fold, 500-fold, or greater, accuracy than a reference polymerase (or an unmodified, naturally occurring polymerase).

In some embodiments, the accuracy of the polymerase can be measured in terms of percentage increase in templating efficiency obtained in a given polymerization reaction. For example, in some embodiments an exemplary modified polymerase encompassed within the scope of the present disclosure may have an increased accuracy of 10%, 15%, 20%, 25%, 30%, 35%, 40%, 45%, 50%, or greater, accuracy than a reference polymerase under identical polymerization conditions.

Some exemplary non-limiting descriptions of accuracy metrics can be found in: Ewing B, Hillier L, Wendl M C, Green P. (1998): Base-calling of automated sequencer traces using phred. I. Accuracy assessment. *Genome Res.* 8(3):175-185; Ewing B, Green P. (1998): Base-calling of automated sequencer traces using phred. II. Error probabilities. *Genome Res.* 8(3):186-194; Dear S, Staden R (1992): A standard file format for data from DNA sequencing instruments. *DNA Sequence,* 3, 107-110; Bonfield J K, Staden R (1995): The application of numerical estimates of base calling accuracy to DNA sequencing projects. *Nucleic Acids Res.* 1995 Apr. 25; 23(8):1406-10, herein incorporated by reference in their entireties.

In some embodiments, the accuracy of a given polymerase (including any of the reference and/or modified polymerases described herein) can be measured in an ion based sequencing reaction; such accuracies can optionally be compared with each other to determine whether a given amino acid mutation increases or decreases the sequencing accuracy relative to a reference and/or unmodified polymerase. In some embodiments, the accuracy of one or more polymerases can be measured using any ion-based sequencing apparatus supplied by Ion Torrent Technologies (Life Technologies Corp., CA), including for example the Ion Torrent PGM™ or Proton™ Sequencer, optionally using the sequencing protocols and reagents provided by Ion Torrent Systems. Some examples of accuracy calculations using an ion-based sequencing systems are described in the Ion Torrent Application Note titled "Ion Torrent: Ion Personal Genome Machine™ Performance Overview, Performance Spring 2011" (Life Technologies Corporation, South San Francisco, Calif.), hereby incorporated by reference in its entirety. In some embodiments, the accuracy of one or more modified polymerases prepared according to the present disclosure can be determined using any appropriate method and/or any appropriate next-generation sequencing platform (such as Roche 454 GS or Illumina HiSeq, MiSeq or HiSeq X Ten platform).

As used herein, the terms "dissociation rate constant" and "dissociation time constant", when used in reference to a given polymerase, refer to the time constant for dissociation ("koff") of a polymerase from a nucleic acid template under a defined set of reaction conditions. Some exemplary assays for measuring the dissociation time constant of a polymerase are described further below. In some embodiments, the dissociation time constant can be measured in units of inverse time, e.g., $sec^{-1}$ or $min^{-1}$.

In some embodiments, the disclosure relates generally to methods (and related kits, systems, apparatus and compositions) for using an isolated modified polymerase including at least one amino acid modification relative to a reference polymerase lacking the at least one amino acid modification and for providing an increase in average read length of primer extension products in a primer extension reaction using the modified polymerase relative to the average read length of primer extension products obtained using the reference polymerase under identical conditions. In some embodiments, the isolated modified polymerase provides an increase in average error-free read length of primer extension products in a primer extension reaction using the modified polymerase, relative to the average error-free read length of primer extension products obtained using a corresponding polymerase lacking the one or more amino acid modifications. In some embodiments, the isolated polymerase having at least one amino acid modification relative to the reference polymerase, provides an increase in average error-free read length of at least 10%, 15%, 20%, 25%, 30%, 35%, 40%, 45%, 50%, 55%, 60%, 65%, 70%, or greater, increase in average error-free read length as compared to the reference polymerase lacking the at least one amino acid modification under identical conditions. Optionally, the modified polymerase includes one or more amino acid substitutions relative to the unmodified polymerase. In some embodiments, the modified polymerase includes two or more amino acid substitutions relative to a reference polymerase lacking the two or more amino acid substitutions. In some embodiments, the primer extension reaction is an ion-based sequencing reaction. In some embodiments, the primer extension reaction is an emPCR based amplification reaction. In some embodiments, the primer extension reaction is a bridge PCR amplification reaction. In some embodiments, the primer extension reaction includes a label such as a reversible terminator in the primer extension reaction.

In some embodiments, the reference polymerase is a naturally occurring or wild type polymerase. In some embodiments, the reference polymerase is a naturally occurring thermostable DNA polymerase. In some embodiments, the reference polymerase is a full-length wild-type Taq DNA polymerase. In some embodiments, the reference polymerase is a truncated but amino acid unmodified Taq DNA polymerase (such as Klentaq-235 DNA polymerase). In other embodiments, the reference polymerase includes a derivative, truncated, mutant or variant form of a naturally occurring polymerase that is different from the modified polymerase. For example, a reference polymerase may omit one or more amino acid mutations (e.g., one or more substitutions, deletions, or additions) as compared to the modified polymerase.

In some embodiments, the disclosure relates generally to methods for performing a nucleotide polymerization reaction, comprising: contacting a modified polymerase with a nucleic acid template in the presence of one or more nucleotides; and polymerizing at least one of the one or more nucleotides using the modified polymerase. The polymerizing optionally further includes polymerizing the at least one nucleotide in a template-dependent fashion. In some embodiments, the modified polymerase includes one or more amino acid substitutions relative to a reference polymerase that does not include the one or more amino acid substitutions.

In some embodiments, the method further includes hybridizing a primer to the template prior to, during, or after the contacting. The polymerizing can include polymerizing the at least one nucleotide onto an end of the primer using the modified polymerase.

In some embodiments, the polymerizing is performed in the proximity of a sensor that is capable of detecting the polymerization of the at least one nucleotide by the modified polymerase.

In some embodiments, the method further includes detecting a signal indicating the polymerization of the at least one of the one or more nucleotides by the modified polymerase using the sensor.

In some embodiments, the modified polymerase, the reference polymerase, or both are a DNA polymerase. The DNA polymerase can include, without limitation, a bacterial DNA polymerase, prokaryotic DNA polymerase, eukaryotic DNA polymerase, archaeal DNA polymerase, viral DNA polymerase or phage DNA polymerase.

In some embodiments, the DNA polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as E. coli DNA polymerase, the Klenow fragment of E. coli DNA polymerase, Bst DNA polymerase, Taq DNA polymerase, Platinum Taq DNA polymerase series, Omni Klen Taq DNA polymerase series, Klen Taq DNA polymerase series, T7 DNA polymerase, and Tth DNA polymerase. In some embodiments, the DNA polymerase is Bst DNA polymerase. In other embodiments, the DNA polymerase is E. coli DNA polymerase I. In some embodiments, the DNA polymerase is the Klenow fragment of E. coli DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Bst polymerase, Tli polymerase, Pfu polymerase, Pfu turbo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, Therminator™ polymerase, phage Phi29 polymerase, and phage B103 polymerase. In some embodiments, the polymerase is KOD polymerase. In some embodiments, the polymerase is Therminator™ polymerase. In some embodiments, the polymerase is phage Phi29 DNA polymerase. In some embodiments the polymerase is phage B103 polymerase, including, for example, the variants disclosed in U.S. Patent Publication No. 20110014612 which is incorporated by reference herein in its entirety.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is a reverse transcriptase (RT) polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity and/or primer extension activity.

Suitable bacterial DNA polymerases include without limitation E. coli DNA polymerases I, II and III, IV and V, the Klenow fragment of E. coli DNA polymerase, Clostridium stercorarium (Cst) DNA polymerase, Clostridium thermocellum (Cth) DNA polymerase, Bacillus stearothermophilus (Bst) DNA polymerase and Sulfolobus solfataricus (Sso) DNA polymerase.

Suitable eukaryotic DNA polymerases include without limitation the DNA polymerases α, δ, ε, η, ζ, γ, β, σ, λ, μ, and κ, as well as the Rev1 polymerase (terminal deoxycytidyl transferase) and terminal deoxynucleotidyl transferase (TdT).

Suitable viral and/or phage DNA polymerases include without limitation T4 DNA polymerase, T5 DNA polymerase, T7 DNA polymerase, Phi-15 DNA polymerase, Phi-29 DNA polymerase (see, e.g., U.S. Pat. No. 5,198,543; also referred to variously as Φ29 polymerase, phi29 polymerase, phi 29 polymerase, Phi 29 polymerase, and Phi29 polymerase); Φ15 polymerase (also referred to herein as Phi-15 polymerase); Φ21 polymerase (Phi-21 polymerase); PZA polymerase; PZE polymerase, PRD1 polymerase; Nf polymerase; M2Y polymerase; SF5 polymerase; f1 DNA polymerase, Cp-1 polymerase; Cp-5 polymerase; Cp-7 polymerase; PR4 polymerase; PR5 polymerase; PR722 polymerase; L17 polymerase; M13 DNA polymerase, RB69 DNA polymerase, G1 polymerase; GA-1 polymerase, BS32 polymerase; B103 polymerase; a polymerase obtained from any phi-29 like phage or derivatives thereof, etc. See, e.g., U.S. Pat. No. 5,576,204, filed Feb. 11, 1993; U.S. Pat. Appl. No. 2007/0196846, published Aug. 23, 2007.

Suitable archaeal DNA polymerases include without limitation the thermostable and/or thermophilic DNA polymerases such as, for example, DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase as well as Turbo Pfu DNA polymerase, *Thermococcus litoralis* (Tli) DNA polymerase or Vent DNA polymerase, *Pyrococcus* sp. GB-D polymerase, "Deep Vent" DNA polymerase, New England Biolabs), *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. 9° N-7 DNA polymerase; *Thermococcus* sp. NA1; *Pyrodictium occultum* DNA polymerase; *Methanococcus voltae* DNA polymerase; *Methanococcus thermoautotrophicum* DNA polymerase; *Methanococcus jannaschii* DNA polymerase; Desulfurococcus strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; the heterodimeric DNA polymerase DP1/DP2, etc.

In some embodiments, the modified polymerase is an RNA polymerase. Suitable RNA polymerases include, without limitation, T3, T5, T7, and SP6 RNA polymerases.

In some embodiments, the polymerase is a reverse transcriptase (RT). Suitable reverse transcriptases include without limitation reverse transcriptases from HIV, HTLV-I, HTLV-II, FeLV, FIV, SIV, AMV, MMTV and MoMuLV, as well as the commercially available "Superscript" reverse transcriptases, (Life Technologies Corp., CA) and telomerases.

In some embodiments, the modified polymerase is derived from a known DNA polymerase. DNA polymerases have been classified into seven different families, based upon both amino acid sequence comparisons and three-dimensional structure analyses. The DNA polymerase I (pol I) or type A polymerase family includes the repair polymerases *E. coli* DNA pol I, *Thermus aquaticus* pol I, and *Bacillus stearothermophilus* pol I, replicative DNA polymerases from some bacteriophages (T3, T5 and T7) and eukaryotic mitochondrial DNA polymerases. The DNA polymerase α (pol α) or type B polymerase family includes all eukaryotic replicating DNA polymerases as well as archaebacterial DNA polymerases, viral DNA polymerases, DNA polymerases encoded in mitochondrial plasmids of various fungi and plants, and the polymerases from bacteriophages T4 and RB69. Family C polymerases are the primary bacterial chromosome replicative enzymes. These are sometimes considered a subset of family Y, which contains the eukaryotic polymerase pol β, as well as other eukaryotic polymerases such as pol σ, pol λ, pol μ, and terminal deoxynucleotidyl transferase (TdT). Family D polymerases are all found in the Euryarchaeota subdomain of Archaea and are thought to be replicative polymerases. The family Y polymerases are called translesion synthesis (TLS) polymerases due to their ability to replicate through damaged DNA. They are also known as error-prone polymerases since they have a low fidelity on undamaged templates. This family includes Pol η, Pol ζ, Pol ι(iota), Pol κ (kappa), and Rev1, and Pol IV and PolV from *E. coli*. Finally, the reverse transcriptase family includes reverse transcriptases from retroviruses and eukaryotic polymerases, usually restricted to telomerases. These polymerases use an RNA template to synthesize the DNA strand, and are also known as RNA-dependent DNA polymerases.

In some embodiments, a modified polymerase or biologically active fragment thereof can be prepared using any suitable method or assay known to one of skill in the art. In some embodiments, any suitable method of protein engineering to obtain a modified polymerase or biologically active fragment thereof is encompassed within the scope of the present disclosure. For example, site-directed mutagenesis is a technique that can be used to introduce one or more known or random mutations within a DNA construct. The introduction of the one or more amino acid mutations can be verified for example, against a standard or reference polymerase or via nucleic acid sequencing. Once verified, the construct containing the one or more of the amino acid mutations can be transformed into bacterial cells and expressed.

Typically, colonies containing mutant expression constructs are inoculated in media, induced, and grown to a desired optical density before collection (often via centrifugation) and purification of the supernatant. It will be readily apparent to the skilled artisan that the supernatant can be purified by any suitable means. Typically, a column for analytical or preparative protein purification is selected. In some embodiments, a modified polymerase or biologically active fragment thereof prepared using the methods can be purified, without limitation, over a heparin column essentially according to the manufacturer's instructions.

Once purified, the modified polymerase or biologically active fragment thereof can be assessed using any suitable method for various polymerase activities, properties, or characteristics. In some embodiments, the polymerase activity, property, or characteristic being assessed will depend on the application of interest. For example, a polymerase used to amplify or sequence a nucleic acid molecule of about 300 to about 600 bp in length can be analyzed for properties such as increased processivity and/or increased read length relative to a reference polymerase lacking the one or more amino acid modifications (e.g., a substitution, deletion or addition). In another example, an application requiring deep targeted-resequencing of a nucleic acid molecule of about 100 bp in length may include polymerase properties such as increased raw accuracy, increased total sequencing throughout, decreased strand bias or reduced systematic error. In some embodiments, the one or more polymerase properties assessed can be related to polymerase performance or polymerase activity in the presence of a high ionic strength solution such as at least 120 mM salt.

In some embodiments, a modified polymerase or biologically active fragment thereof prepared according to the methods disclosed herein can be assessed for DNA binding activity, nucleotide polymerization activity, primer extension activity, strand displacement activity, reverse transcriptase activity, 3'-5' exonuclease (proofreading) activity, and the like.

In some embodiments, a modified polymerase or biologically active fragment thereof prepared according to the methods can be assessed for increased accuracy, increased processivity, increased average read length, increased minimum read length, increased total sequencing throughput, reduced strand bias, reduced systematic error, increased AQ20, increased 200Q17 value or the ability to perform nucleotide polymerization as compared to a reference polymerase under the same conditions. In some embodiments, the modified polymerase or the biologically active fragment thereof can be assessed for any one of the polymerase activities in the presence of a high ionic strength solution (e.g., a salt solution having at least 120 mM salt such as NaCl and/or KCl.

In some embodiments, the modified polymerase or biologically active fragment thereof is optionally characterized by a change (e.g., increase or decrease) in any one or more of the following properties (often, relative to a polymerase lacking the corresponding one or more amino acid mutations): dissociation time constant, rate of dissociation of polymerase from a given nucleic acid template, binding affinity of the polymerase for a given nucleic acid template, as well as for properties that are associated with a nucleic acid sequencing reactions such as average read length, minimum read length, accuracy, total number of perfect reads, total sequencing throughput, strand bias, systematic error, fold-increase in throughput of a sequencing reaction, performance in salt (i.e., ionic strength), AQ20, average error-free read length, error-rate, 100Q17 value, 200Q17 value, Q score, raw read accuracy, and processivity. It will be understood that in illustrative embodiments of the present invention, the modified polymerase is used in an emulsion PCR reaction to amplify templates as part of a sequencing workflow, for example to amplify templates on a solid support, and in some illustrative embodiments, to clonally amplify templates on a solid support. Methods for making emulions and performing emulsion PCR are known in the art. Compounds for making emulsions such as biocompatible oils and emulsion stabilizers are available commercially (e.g. Sigma, St. Louis Mo.; Unigema, New Jersey). The nucleic acid sequence of at least a portion of the amplified templates is then determined. The results of this sequence determination are compared to results of similar experiments performed with a reference polymerase, such as Taq polymerase (SEQ ID NO:1) or the modified Taq polymerase of SEQ ID:34, for an emulsion PCR template amplification step. The examples provided herein demonstrate the performance of a specific example of such comparative test. A library of nucleic acid molecules can be amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463), except that an on-test or reference polymerase can be used in place of the polymerase provided in the kit and the results of the on-test polymerase can be compared to those generated with the reference polymerase. The amplified nucleic acid molecules are then loaded into a PGM™ 314 sequencing chip. The chip is loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923).

In some embodiments, the modified polymerase or biologically active fragment thereof can be assessed individually with respect to known values in the art for an analogous polymerase. In some embodiments, a modified polymerase or biologically active fragment thereof prepared according to the methods disclosed herein can be assessed against a known or reference polymerase under similar or identical conditions. In some embodiments, the conditions can include amplifying or sequencing a nucleic acid molecule in the presence of a high ionic strength solution.

In some embodiments, the disclosure relates generally to methods for producing a plurality of modified polymerases or biologically active fragments. In some embodiments, the disclosure relates generally to methods for producing a plurality of modified polymerases or biologically active fragments using a high-throughput or automated system. In some embodiments, the methods comprise mixing a plurality of modified polymerases or biologically active fragments with a series of reagents necessary for protein purification and extracting the purified polymerases or biologically active fragments from the mixture. In one example, a plurality of random or site-directed mutagenesis reactions can be prepared in a 96- or 384-well plate. Optionally, the contents of the 96- or 384-well plate can undergo an initial screen to identify polymerase mutant constructs. The contents of each individual well (or the contents of each well from an initial screen) can be delivered to a series of flasks, tubes or shakers for inoculation and induction. Once at the required optical density, the flask, tubes or shakers can be centrifuged and the supernatants recovered. Each supernatant can undergo protein purification, for example via fully automated column purification (for example see, Camper and Viola, Analytical Biochemistry, 2009, p 176-181). The purified modified polymerases or biologically active fragments can be assessed for one, or a combination of polymerase activities, such as DNA binding, primer extension, strand displacement, reverse transcriptase activity, and the like. It is envisaged that the skilled artisan can use the method (or variations of the methods that are within the scope of the disclosure) to identify a plurality of modified polymerases or biologically active fragments. In some aspects, the methods can be used to identify a plurality of modified polymerases or biologically active fragments having enhanced accuracy as compared to a reference polymerase under the same conditions. In some embodiments, the methods can be used to identify a plurality of modified polymerases or biologically active fragments thereof having enhanced accuracy in the presence of a high ionic strength solution. In some aspects, the methods can be used to identify a plurality of modified polymerases or biologically active fragments having enhanced read length as compared to a reference polymerase under the same conditions. In some embodiments, the methods can be used to identify a plurality of modified polymerases or biologically active fragments thereof having enhanced read length in the presence of a high ionic strength solution. In some aspects, the methods can be used to identify a plurality of modified polymerases or biologically active fragments having enhanced thermostability as compared to a reference polymerase under the same conditions. In some embodiments, the methods can be used to identify a plurality of modified polymerases or biologically active fragments thereof having enhanced thermostability in the presence of a high ionic strength solution. In some aspects, the methods can be used to identify a plurality of modified polymerases or biologically active fragments having reduced strand bias and/or reduced systematic error as compared to a reference polymerase under the same conditions. In some embodiments, the methods can be used to identify a plurality of modified polymerases or biologically active fragments thereof having reduced strand bias and/or reduced systematic error in the presence of a high ionic strength solution. In some embodiments, the high ionic strength solution can include a KCl and/or NaCl salt. In some embodiments, the high ionic strength solution can be at least 120 mM salt. In some embodiments, the high ionic strength solution can be from 125 mM to 200 mM salt. In some embodiments, the high ionic strength solution can be about 130 mM, 150 mM, 200 mM, 225 mM, 250 mM, 275 mM, 300 mM, 350 mM, 400 mM, 450 mM, 500 mM, or greater salt concentration. In some embodiments, the high ionic strength solution can be about 125 mM to about 400 mM salt. In some embodiments, the high ionic strength solution can be about 150 mM to about 275 mM salt. In some embodiments, the high ionic strength solution can be about 200 mM to about 250 mM salt. It will be apparent to the skilled artisan that various other suitable salts can be used in place, or in combination with KCl and/or NaCl. In some embodiments, the ionic strength solution can further include a sulfate.

As will be readily apparent to the skilled artisan, the disclosure outlines an exemplary automated and high-throughput method to generate a library of modified polymerases or biological active fragments. The disclosure also outlines methods to assess such modified polymerases or biologically active fragments for polymerase activities. It is also encompassed by the disclosure that the skilled artisan can readily produce a mutagenized library of constructs where every amino acid of the polymerase of interest can be mutated. In some embodiments, a mutagenized library can be prepared wherein each amino acid residue within the polymerase is mutated by every possible amino acid combination. In some embodiments, a mutagenized library can be prepared where each amino acid residue within the polymerase is mutated, and where the combination of possible amino acid mutations is limited to conservative or non-conservative amino acid substitutions. In both examples, mutagenized libraries can be created containing vast numbers of mutant constructs that can be applied through an automated or high-throughput system for purification or for initial screening. In some embodiments, plates of 96- or 384-library constructs representing a mutagenized library can be assessed for one or more polymerase activities using an ISFET based sequencing polymerase screen, using a next generation (i.e. high-throughput) platform (e.g., Ion Torrent Systems Personal Genome Machine and a Ion based ISFET Sequencing Chip (Life Technologies Corp, CA). In one example, the polymerase screen can include one or more 96- or 384-plates representing a mutagenized library; where each well of the plate consists of a different construct (modified polymerase) containing at least one, or more, amino acid mutations as compared to a reference polymerase in at least one well on the same plate (lacking the at least one or more amino acid mutations). In some embodiments, the reference polymerase acts as a control sample within the 96- or 384-plate to assess polymerase activity of each modified polymerase within the wells of the same plate. In some embodiments, the library of constructs and reference polymerase within the plate can further include a unique barcode for each modified polymerase within the plate. Thus, a 96-well plate may contain 96 barcodes if each well in the plate contains either a reference polymerase or a modified polymerase construct. Once purified, the mutagenized library of proteins can be assessed for one, or a combination of polymerase activities, such as DNA binding, primer extension, strand displacement, reverse transcriptase, nick-initiated polymerase activity, raw accuracy, increase total sequencing throughput, reduced strand bias, lowered systematic error, increased read length, increased processivity, increased thermostability, and the like. In some embodiments, the template libraries can further include template libraries that are known to perform well under the proposed amplification conditions, so that the well-performing template libraries can act as a baseline or control reading.

Optionally, the purified modified polymerases or biologically active fragments thereof can be further assessed for other properties such as the ability to amplify or sequence a nucleic acid molecule in the presence of high salt. The source or origin of the polymerase to be mutated is generally not considered critical. For example, eukaryotic, prokaryotic, archaeal, bacterial, phage or viral polymerases can be used in the methods. In some embodiments, the polymerase can be a DNA or RNA polymerase. In some embodiments, the DNA polymerase can include a family A or family B polymerase. In some embodiments, the DNA polymerase can include a thermostable DNA polymerase. The exemplary methods provided herein are to be considered illustrative in view of the field of protein engineering and enzymatics and should not be construed as in any way limiting.

In some embodiments, the modified polymerase or a biologically active fragment thereof, includes one or more amino acid mutations that are located inside the catalytic domain of the modified polymerase. In some embodiments, the modified polymerase or biologically active fragment thereof can include at least 25, 50, 75, 100, 150, or more amino acid residues of the catalytic domain. In some embodiments, the modified polymerase or biologically active fragment thereof can include any part of the catalytic domain that comprises at least 25, 50, 75, 100, 150, or more contiguous amino acid residues. In some embodiments, the modified polymerase or biologically active fragment thereof can include at least 25 contiguous amino acid residues of the catalytic domain and can optionally include one or more amino acid residues at the C-terminal or the N-terminal that are outside the catalytic domain. In some embodiments, the modified polymerase or a biologically active fragment can include any 25, 50, 75, 100, 150, or more contiguous amino acid residues of the catalytic domain coupled to any one or more non-catalytic domain amino acid residues.

In some embodiments, the modified polymerase (or biologically active fragment thereof) includes one or more amino acid mutations that are located inside the catalytic domain of the modified polymerase, and wherein the polymerase has at least 80%, 85%, 90%, 95%, 96%, 97%, 98%, 99%, or more identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 25 or 50 contiguous amino acid residues of the catalytic domain and has at least 80% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO:

In some embodiments, the modified polymerase or biologically active fragment thereof includes at least 75 contiguous amino acid residues of the catalytic domain and has at least 85% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 25 or 50 contiguous amino acid residues of the catalytic domain and has at least 90% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 25 contiguous amino acid residues of the catalytic domain and has at least 95% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 25 or 50 contiguous amino acid residues of the catalytic domain and has at least 98% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 25 or 50 contiguous amino acid residues of the catalytic domain and has at least 99% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or a biologically active fragment thereof, includes one or more amino acid mutations that are located inside the DNA binding domain of the polymerase. In some embodiments, the modified polymerase or biologically active fragment thereof can include at least 25, 50, 75, 100, 150, or more amino acid residues of the DNA binding domain of the modified polymerase. In some embodiments, the modified polymerase or biologically active fragment thereof can include any part of the DNA binding domain that comprises at least 25, 50, 75, 100, 150, or more contiguous amino acid residues. In some embodiments, the modified polymerase or biologically active fragment thereof can include at least 25 contiguous amino acid residues of the binding domain and can optionally include one or more amino acid residues at the C-terminal or the N-terminal that are outside of the binding domain. In some embodiments, the modified polymerase or a biologically active fragment can include any 25, 50, 75, 100, 150 or more contiguous amino acid residues of the binding domain coupled to any one or more non-binding domain amino acid residues. In some embodiments, the modified polymerase (or biologically active fragment thereof) includes one or more amino acid mutations that are located inside the DNA binding domain of the modified polymerase, and wherein the polymerase has at least 80%, 85%, 90%, 95%, 96%, 97%, 98%, 99%, or more identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 25 contiguous amino acid residues of the DNA binding domain and has at least 80% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 25 contiguous amino acid residues of the DNA binding domain and has at least 85% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 25 contiguous amino acid residues of the DNA binding domain and has at least 90% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 25 contiguous amino acid residues of the DNA binding domain and has at least 95% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 25 contiguous amino acid residues of the DNA binding domain and has at least 98% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33. In some embodiments, the modified polymerase or biologically active fragment thereof includes at least 50 contiguous amino acid residues of the DNA binding domain and has at least 80%, 85%, 90%, 95%, 98%, or 99% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or a biologically active fragment thereof, includes one or more amino acid mutations that are located outside the catalytic domain (also referred to herein as the DNA binding cleft) of the polymerase. The catalytic domains of the A family DNA polymerases, B family DNA polymerases and reverse transcriptases, as well as the RNA-dependent RNA polymerases are well known; all share a common overall structure and catalytic mechanism. The catalytic domains of all these polymerases have a shape that has been compared to a right hand and consists of "palm", "thumb" and "finger" domains. The palm domain typically contains the catalytic site for the phosphoryl transfer reaction. The thumb is thought to play a role positioning the duplex DNA and in processivity and translocation. The fingers interact with the incoming nucleotide as well as the template base with which it is paired. The palm domains are homologous in the A, B and RT families, but the arrangements of the fingers and thumb are different.

The thumb domains of the different polymerase families do share common features, containing parallel or anti-parallel α-helices, with at least one α-helix interacting with the minor groove of the primer-template complex. The fingers domain also conserves an α-helix positioned at the blunt end of the primer-template complex. This helix contains highly conserved side chains (the B motif).

Three conserved motifs, A, B, and C have been identified for the A family polymerases. The A and C motifs are typically conserved in both the B family polymerases and the RT polymerases. (Delarue et al., Protein Engineering 3: 461-467 (1990)).

In some embodiments, for the A family polymerases, the A motif comprises the consensus sequence:

a. DXSXXE.   (SEQ ID NO: 35)

In some embodiments, for the A family polymerases, the B motif comprises the consensus sequence:

a. KXXXXXXYG   (SEQ ID NO: 36)

In some embodiments, for the A family polymerases, the C motif comprises the consensus sequence:

a. VHDE   (SEQ ID NO: 37)

In some embodiments, the polymerase optionally comprises any A family polymerase, or biologically active fragment, mutant, variant or truncation thereof, wherein the linking moiety is linked to any amino acid residue of the A family polymerase, or biologically active fragment mutant, variant or truncation thereof, that is situated outside the A, B or C motifs. In some embodiments, the linking moiety is linked to any amino acid residue of the A family polymerase, or biologically active fragment, that is situated outside the A motif, the B motif or the C motif.

The A and C motifs typically form part of the palm domain, and each motif typically contains a strictly conserved aspartic acid residue, which are involved in the catalytic mechanism common to all the DNA polymerases. DNA synthesis can be mediated by transfer of a phosphoryl group from the incoming nucleotide to the 3' OH of the DNA, releasing a polyphosphate moiety and forming a new DNA phosphodiester bond. This reaction is typically catalyzed by a mechanism involving two metal ions, normally $Mg^{2+}$, and the two conserved aspartic acid residues.

In some embodiments, the conserved glutamic acid residue in motif A of the A family DNA polymerases plays an important role in incorporation of the correct nucleotide, as does the corresponding conserved tyrosine in B family members (Minnick et al., Proc. Natl. Acad. Sci. USA 99: 1194-1199 (2002); Parsell et al, Nucleic Acids Res. 35: 3076-3086 (2002). Mutations at the conserved Leu of motif A affect replication fidelity (Venkatesan et al., J. Biol. Chem. 281: 4486-4494 (2006)).

In some embodiments, the B motif contains conserved lysine, tyrosine and glycine residues. The B motif of *E coli* pol I has been shown to bind nucleotide substrates and contains a conserved tyrosine which has been shown to be in the active site.

In some embodiments, for the B family polymerases, the A motif comprises the consensus sequence:

DXXSLYPS. (SEQ ID NO: 38)

In some embodiments, for the B family polymerases, the B motif comprises the consensus sequence:

KXXXNSXYG (SEQ ID NO: 39)

In some embodiments, for the B family polymerases, the C motif comprises the consensus sequence:

a. YGDTDS (SEQ ID NO: 40)

The residues in bold indicate invariant residues.

In some embodiments, the modified polymerase optionally comprises any B family polymerase, or biologically active fragment, mutant, variant or truncation thereof, wherein the linking moiety is linked to any amino acid residue of the B family polymerase, or biologically active fragment, mutant, variant or truncation thereof that is situated outside the A, B or C motifs. In some embodiments, the linking moiety is linked to any amino acid residue of the B family polymerase, or biologically active fragment, that is situated outside the A motif, the B motif or the C motif.

In some embodiments, the B family polymerases contain six conserved motifs, of which regions I and II correspond to the A and C motifs of the A family. Region III is involved in nucleotide binding and is functionally homologous to motif B. Regions I, II and III converge at the center of the active site from the palm (I), the fingers (II), and base of the thumb (III) to produce a contiguous conserved surface. Within these regions, a set of highly conserved residues form three chemically distinct clusters consisting of exposed aromatic residues, negatively charged residues, and positively charged residues, respectively. For example, in the replication polymerase of the bacteriophage RB69, these three clusters correspond to the following amino acid residues: Y416, Y567, and Y391 (exposed aromatic residues), D621, D623, D411, D684, and E686 (negatively charged residues), and K560, R482, and K486 (positively charged residues). See Wang et al, Cell 89: 1087-1099 (1997). These three clusters typically encompass the region in which the primer terminus and the incoming nucleotide would be expected to bind. In some embodiments, the modified polymerase optionally comprises any B family polymerase, or biologically active fragment, mutant, variant or truncation thereof, wherein the linking moiety is linked to any amino acid residue of the B family polymerase, or biologically active fragment, mutant, variant or truncation thereof that is situated outside one or more of these conserved amino acid clusters or motifs. In some embodiments, the linking moiety is linked to any amino acid residue of the B family polymerase, or biologically active fragment, mutant, variant or truncation thereof that is situated outside any of these conserved amino acid clusters or motifs.

The RT polymerases contain four conserved sequence motifs (Poch et al., EMBO J. 12: 3867-3874 (1989)), with motifs A and C containing the conserved catalytic aspartates. The integrity of motif B is also required for reverse transcriptase function.

The consensus sequence for motif A is DXXXXF/Y (SEQ ID NO: 41)

The consensus sequence for motif B is FXGXXXS/A (SEQ ID NO: 42)

The consensus sequence for motif C is YXDD (SEQ ID NO: 43)

The consensus sequence for motif D is GXXXXXXXK (SEQ ID NO: 44).

Mutations in the YXDD motif (motif C), the most highly conserved of these motifs, can abolish polymerase activity and alter the processivity and fidelity (Sharma et al., Antiviral Chemistry and Chemotherapy 16: 169-182 (2005)). In addition, the conserved lysine residue in motif D, a loop that is unique to the RT polymerases, is an invariant residue important for nucleotide binding (Canard et al., J. Biol. Chem. 274: 35768-35776 (1999)).

In some embodiments, the modified polymerase optionally comprises any RT polymerase, or biologically active fragment, mutant, variant or truncation thereof, wherein the linking moiety is linked to any amino acid residue of the RT polymerase, or biologically active fragment, mutant, variant or truncation thereof that is situated outside one or more of the A, B, C and D motifs. In some embodiments, the linking moiety is linked to any amino acid residue of the RT polymerase, or biologically active fragment, mutant, variant or truncation thereof that is situated outside any of these motifs.

In some embodiments, the modified polymerase includes one or more modifications (including amino acid substitutions, deletions, additions or chemical modifications) located at any position other than at the conserved or invariant residues.

In some embodiments, the modified polymerase or biologically active fragment thereof includes at least 25, 50, 75, or 100 contiguous amino acid residues having at least 80% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 50, 75, 100, 150, 175, 200 contiguous amino acid residues having at least 85% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 225, 250, 275, 300, 325, 350, 375, 400 contiguous amino acid residues having at least 85% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 50, 75, 100, 150, 200, 250, 300, 350, 400, 450, 500, or more contiguous amino acid residues having at least 90% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 100, 200, 300, 400, 500, 600, 700, or more contiguous amino acid residues having at least 95% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 100 contiguous amino acid residues having at least 98% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 150 contiguous amino acid residues having at least 99% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 200 contiguous amino acid residues having at least 99% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, the modified polymerase or biologically active fragment thereof includes at least 400 contiguous amino acid residues having at least 99% identity to any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO:33.

In some embodiments, in addition to the polymerase domains, the modified polymerase can include one or more additional functional domains, including domains required for 3'→5' (reverse) exonuclease activity that mediates proofreading of the newly synthesized DNA strand, or for 5'→3' (forward) exonuclease activity that mediates nick translation during DNA repair, or for FLAP endonuclease activity. In some embodiments, the modified polymerase has strand-displacing activity, and can catalyze nucleic acid synthesis by polymerizing nucleotides into the 3' end of a nick within a double stranded nucleic acid template while simultaneously displacing the nucleic acid located downstream of the nick. It will be appreciated to one of skill in the art, that a modified polymerase as encompassed by the present disclosure optionally has any one or more of these activities as well.

The 3' to 5' exonuclease proofreading domains of both A and B family DNA polymerases contain three conserved motifs, called Exo I, Exo II and Exo III, each of which contains an invariant aspartic acid residue essential for metal binding and exonuclease function. Alterations of these conserved aspartic acid residues result in proteins which retain polymerase activity, but are deficient in exonuclease activity (Hall et al., J. Gen. Virol. 76: 2999-3008 (1995)). Conserved motifs in the 5' to 3' exonuclease domains and amino acid alterations that affect exonuclease activity have also been identified (U.S. Pat. No. 5,466,591).

Representative examples of A family enzymes are *E. coli*. Pol I, or the Klenow fragment of *E coli*. Pol I, Bst DNA polymerase, Taq DNA polymerase, T7 DNA polymerase and Tth DNA polymerase. A family enzymes also include the Platinum Taq DNA polymerase series.

In some embodiments, the A family enzymes are characterized by high DNA elongation rates but can have poor fidelity because of the lack of 3'-5' exonuclease activity. In some embodiments, the B family enzymes can have high fidelity owing to their 3'-5' exonuclease activity but can achieve low DNA elongation rates.

Other types of polymerases include, for example, Tbr polymerase, Tfl polymerase, Tru polymerase, Tac polymerase, Tne polymerase, Tma polymerase, Tih polymerase, Tfi polymerase and the like. RT polymerases include HIV reverse transcriptase, Moloney Murine Leukemia Virus (M-MLV) reverse transcriptase, Avian Myeloblastosis Virus (AMV) reverse transcriptase or Rous Sarcoma Virus (RSV) reverse transcriptase. Variants, modified products and derivatives thereof are also usable. Similarly, Taq, Platinum Taq, Tth, Tli, Pfu, Pfutubo, Pyrobest, Pwo and KOD, VENT, DEEPVENT, EX-Taq, LA-Taq, Therminator™ the Expand series and Platinum Taq Hi-Fi are all commercially available. Other enzymes can be readily isolated from specific bacteria by those of ordinary skill in the art.

One exemplary polymerase, E. coli DNA polymerase I ("Pol I") possesses three enzymatic activities: a 5' to 3' DNA polymerase activity; a 3' to 5' exonuclease activity that mediates proofreading; and a 5' to 3' exonuclease activity mediating nick translation during DNA repair. The Klenow fragment is a large protein fragment produced when E. coli Pol I is proteolytically cleaved by subtilisin. It retains the polymerase and proofreading exonuclease activities, but lacks the 5' to 3' exonuclease activity. An exo-Klenow fragment which has been mutated to remove the proofreading exonuclease activity is also available. The structure of the Klenow fragment shows that highly conserved residues that interact with DNA include N675, N678, K635, R631, E611, T609, R835, D827, S562 and N579 (Beese et al, Science 260: 352-355 (1993)).

Arg682 in the Klenow fragment of E. coli DNA polymerase I (pol I) is important for the template-dependent nucleotide-binding function, and appears to maintain high processivity of the DNA polymerase (Pandey et al., European Journal of Biochemistry, 214:59-65 (1993)).

In some embodiments, the modified polymerase can be derived from Taq DNA polymerase, which is an A family DNA polymerase derived from the thermophilic bacterium Thermus aquaticus. It is best known for its use in the polymerase chain reaction. Taq polymerase lacks a proofreading activity, and thus has a relatively low replication fidelity (Kim et al., Nature 376: 612-616 (2002).

In some embodiments, the polymerase can be derived from the T7 DNA polymerase of bacteriophage T7, which is an A family DNA polymerase that consists of a 1:1 complex of the viral T7 gene 5 protein (80 k Da) and the E. coli thioredoxin (12 k Da). It lacks a 5'→3' exonuclease domain, but the 3'→5' exonuclease activity is approximately 1000-fold greater than that of E coli Klenow fragment. The exonuclease activity appears to be responsible for the high fidelity of this enzyme and prevents strand displacement synthesis. This polymerase typically exhibits high levels of processivity.

In some embodiments, the polymerase can be derived from KOD DNA polymerase, which is a B family DNA polymerase derived from Thermococcus kodakaraensis. KOD polymerase is a thermostable DNA polymerase with high fidelity and processivity.

In some embodiments, the polymerase can be derived from the Therminator™ DNA polymerase, which is also a B family DNA polymerase. Therminator™ is an A485L point mutation of the DNA polymerase from Thermococcus species 9oN-7 (Ichida et al., Nucleic Acids Res. 33: 5214-5222 (2005)). Therminator™ polymerase has an enhanced ability to incorporate modified substrates such as dideoxynucleotides, ribonucleotides, and acyclonucleotides.

In some embodiments, the polymerase can be derived from a Phi29 polymerase or a Phi29-type polymerase, for example a polymerase derived from the bacteriophage B103. The Phi29 and B103 DNA polymerases are B family polymerases from related bacteriophages. In addition to the A, B and C motifs, the Phi29 family of DNA polymerases contain an additional conserved motif, KXY in region Y (Blanco et al., J. Biol. Chem. 268: 16763-16770 (1993). Mutations to Phi29 and B103 polymerases that affect polymerase activity and nucleotide binding affinity are described in U.S. Patent Publication No. 20110014612 and its priority documents U.S. Provisional Application Nos. 61/307,356; 61/299,917; 61/299,919; 61/293,616; 61/293,618; 61/289, 388; 61/263,974; 61/245,457; 61/242,771; 61/184,770; and 61/164,324, herein incorporated by reference in their entireties.

In some embodiments, the polymerase is derived from the reverse transcriptase from human immunodeficiency virus type 1 (HIV-1), which is a heterodimer consisting of one 66-kDa and one 51-kDa subunit. The p66 subunit contains both a polymerase and an RNase H domain; proteolytic cleavage of p66 removes the RNase H domain to yield the p51 subunit (Wang et al., PNAS 91:7242-7246 (1994)). The structure of the HIV-1 reverse transcriptase shows multiple interactions between the 2'-OH groups of the RNA template and the reverse transcriptase. Residues Ser280 and Arg284 of helix I in the p66 thumb are involved in the RNA-RT interactions, as well as residues Glu89 and Gln91 of the template grip in the p66 palm. The p51 subunit also plays a role in the interactions between the RNA-DNA duplex and the RT, with residues Lys395, Glu396, Lys22 and Lys390 of the p51 subunit also interacting with the DNA:RNA duplex (Kohlstaedt et al, Science 256: 1783-1790 (1992) and Safarianos et al, The EMBO Journal 20:1449-1461 (2001)).

In some embodiments, the polymerase is derived from the Bst DNA polymerase of Bacillus stearothermophilus, or any biologically active fragment thereof. The Bst polymerase can be a family A DNA polymerase. The large fragment of the naturally occurring Bst DNA polymerase is equivalent to the Klenow fragment of E. coli Pol I, retaining the polymerase and proofreading exonuclease activities while lacking the 5' to 3' exonuclease activity. In some embodiments, the polymerase derived from Bst DNA polymerase can lack 3' to 5' exonuclease activity. As used herein, the term "Bst DNA polymerase" may refer to a full length Bst protein or to a Bst large fragment.

In some embodiments, the modified polymerase consists of or comprises an isolated variant of a polymerase having or comprising an amino acid sequence that is at least 80% identical to the amino acid sequence of a wild type full length or wild type large fragment Bst DNA polymerase. In some embodiments, the modified polymerase is an isolated variant of a Bst DNA polymerase comprising a variant having an amino acid sequence that is at least 85%, at least 90%, at least 91%, at least 92%, at least 93%, at least 94%, at least 95%, at least 96%, at least 97%, at least 98%, or at least 99% identical to the amino acid sequence of wild type Bst or large fragment Bst DNA polymerase. In some embodiments, the modified Bst polymerase includes one or more amino acid modifications (e.g., amino acid substitutions, deletions, additions or chemical modifications) relative to a Bst polymerase corresponding to a reference polymerase (e.g., wild-type Bst DNA polymerase).

In some embodiments, the modified polymerase consists of or comprises an isolated variant of a Bst DNA polymerase having or comprising the amino acid sequence of wild type full length Bst DNA polymerase further comprising one or more of the following amino acid substitutions: His46Arg (H46R), Glu446Gln (E446Q), and His572Arg (H572R), wherein the numbering is relative to the wild type amino acid sequence of Bst DNA polymerase.

In some embodiments, the modified polymerase consists of or comprises an isolated variant of a polymerase having or comprising an amino acid sequence that is at least 90%, at least 91%, at least 92%, at least 93%, at least 94%, at least 95%, at least 96%, at least 97%, at least 98%, or at least 99% identical to the amino acid sequence of wild type full length Bst DNA polymerase further comprising one or more of each of the following amino acid substitutions: His46Arg (H46R), Glu446Gln (E446Q), and His572Arg (H572R), wherein the numbering is relative to the wild type full length amino acid sequence of Bst DNA polymerase. In some embodiments, the modified polymerase includes one or more amino acid modifications (e.g., amino acid substitutions, deletions, additions or chemical modifications) relative to the reference polymerase (e.g., a polymerase lacking the one or more amino acid modifications).

In some embodiments, the modified polymerase or the biologically active fragment thereof comprises or consists of at least 80% identity to SEQ ID NO: 1. In some embodiments, the modified polymerase or the biologically active fragment thereof comprises or consists of at least 100 contiguous amino acid residues having at least 90% identity to SEQ ID NO: 1, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 90% identity to SEQ ID NO: 1, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 95% identity to SEQ ID NO: 1, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 95% identity to SEQ ID NO: 1, wherein the modified polymerase or biological active fragment thereof has improved thermostability as compared to SEQ ID NO: 1.

In some embodiments, the modified polymerase or the biologically active fragment thereof comprises or consists of at least 100 contiguous amino acid residues having at least 98% identity to SEQ ID NO: 1, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 98% identity to SEQ ID NO: 1, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 99% identity to SEQ ID NO: 1, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 99% identity to SEQ ID NO: 1, wherein the modified polymerase or biologically active fragment thereof has improved thermostability as compared to SEQ ID NO: 1.

In some embodiments, the modified polymerase or the biologically active fragment thereof comprises or consists of at least 90% identity to SEQ ID NO: 1. In some embodiments, the modified polymerase or the biologically active fragment thereof comprises or consists of at least 100 contiguous amino acid residues having at least 90% identity to SEQ ID NO: 1, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 90% identity to SEQ ID NO: 1, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 95% identity to SEQ ID NO: 1, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 95% identity to SEQ ID NO: 1, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 98% identity to SEQ ID NO: 1, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 98% identity to SEQ ID NO: 1, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 99% identity to SEQ ID NO: 1, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 99% identity to SEQ ID NO: 1, wherein the modified polymerase or biologically active fragment thereof has improved accuracy as compared to SEQ ID NO: 1.

In some embodiments, the modified polymerase consists of or comprises an isolated variant of a polymerase having or comprising an amino acid sequence that is at least 80% identical to the amino acid sequence of SEQ ID NO: 2. In some embodiments, the polymerase is a variant of a Taq DNA polymerase comprising an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2. In some embodiments, the reference polymerase is a Taq DNA polymerase consisting of the amino acid sequence of SEQ ID NO: 2 and the modified polymerase includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 2.

In some embodiments, the modified polymerase or the biologically active fragment thereof comprises or consists of at least 100 contiguous amino acid residues having at least 90% identity to SEQ ID NO: 2, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 95% identity to SEQ ID NO: 2, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 98% identity to SEQ ID NO: 2, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 99% identity to SEQ ID NO: 2, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 90% identity to SEQ ID NO: 2, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 95% identity to SEQ ID NO: 2, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 98% identity to SEQ ID NO: 2, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 99% identity to SEQ ID NO: 2, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 90% identity to SEQ ID NO: 2, and wherein the modified polymerase or biological active fragment thereof has improved thermostability as compared to SEQ ID NO: 34. In some embodiments, the modified polymerase or the biologically active fragment thereof comprises or consists of at least 150 contiguous amino acid residues having at least 95% identity to SEQ ID NO: 2, wherein the modified polymerase or biologically active fragment thereof has improved thermostability as compared to SEQ ID NO: 34.

In some embodiments, the modified polymerase or the biologically active fragment thereof comprises or consists of at least 100 contiguous amino acid residues having at least 98% identity to SEQ ID NO: 2, and wherein the modified polymerase or biological active fragment thereof has improved thermostability as compared to SEQ ID NO: 34. In some embodiments, the modified polymerase or the biologically active fragment thereof comprises or consists of at least 150 contiguous amino acid residues having at least 99% identity to SEQ ID NO: 2, wherein the modified polymerase or biologically active fragment thereof has improved thermostability as compared to SEQ ID NO: 34.

In some embodiments, the modified polymerase or the biologically active fragment thereof comprises or consists of at least 100 contiguous amino acid residues having at least 90% identity to SEQ ID NO: 2, and wherein the modified polymerase or biological active fragment thereof has improved accuracy as compared to SEQ ID NO: 34. In some embodiments, the modified polymerase or the biologically active fragment thereof comprises or consists of at least 150 contiguous amino acid residues having at least 95% identity to SEQ ID NO: 2, wherein the modified polymerase or biologically active fragment thereof has improved accuracy as compared to SEQ ID NO: 34.

In some embodiments, the modified polymerase or the biologically active fragment thereof comprises or consists of at least 100 contiguous amino acid residues having at least 98% identity to SEQ ID NO: 2, and wherein the modified polymerase or biological active fragment thereof has improved accuracy as compared to SEQ ID NO: 34. In some embodiments, the modified polymerase or the biologically active fragment thereof comprises or consists of at least 150 contiguous amino acid residues having at least 99% identity to SEQ ID NO: 2, wherein the modified polymerase or biologically active fragment thereof has improved accuracy as compared to SEQ ID NO: 34.

In some embodiments, the modified polymerase can include an amino acid sequence or any biologically active fragment thereof having or comprising the amino acid sequence of SEQ ID NO: 3. In some embodiments, the modified polymerase can include an amino acid sequence of any biologically active fragment of a polymerase having or comprising an amino acid sequence that is at least 80%, at least 85%, at least 90%, at least 95%, at least 96%, at least 97%, at least 98%, or at least 99% identical to the amino acid sequence of SEQ ID NO: 3. In some embodiments, the reference polymerase is a Taq DNA polymerase consisting of the amino acid sequence of SEQ ID NO: 3 and the modified polymerase includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 3.

In some embodiments, the modified polymerase or the biologically active fragment thereof comprises or consists of at least 100 contiguous amino acid residues having at least 90% identity to SEQ ID NO: 3, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 95% identity to SEQ ID NO: 3, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 98% identity to SEQ ID NO: 3, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 99% identity to SEQ ID NO: 3, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 90% identity to SEQ ID NO: 3, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 95% identity to SEQ ID NO: 3, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 98% identity to SEQ ID NO: 3, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 99% identity to SEQ ID NO: 3, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 90% identity to SEQ ID NO: 3, and wherein the modified polymerase or biological active fragment thereof has improved thermostability as compared to SEQ ID NO: 34. In some embodiments, the modified polymerase or the biologically active fragment thereof comprises or consists of at least 150 contiguous amino acid residues having at least 95% identity to SEQ ID NO: 3, wherein the modified polymerase or biologically active fragment thereof has improved thermostability as compared to SEQ ID NO: 34.

In some embodiments, the modified polymerase or the biologically active fragment thereof comprises or consists of at least 100 contiguous amino acid residues having at least 98% identity to SEQ ID NO: 3, and wherein the modified polymerase or biological active fragment thereof has improved thermostability as compared to SEQ ID NO: 34. In some embodiments, the modified polymerase or the biologically active fragment thereof comprises or consists of at least 150 contiguous amino acid residues having at least 99% identity to SEQ ID NO: 3, wherein the modified polymerase or biologically active fragment thereof has improved thermostability as compared to SEQ ID NO: 34.

In some embodiments, the modified polymerase or the biologically active fragment thereof comprises or consists of at least 100 contiguous amino acid residues having at least 90% identity to SEQ ID NO: 3, and wherein the modified polymerase or biological active fragment thereof has improved accuracy as compared to SEQ ID NO: 34. In some embodiments, the modified polymerase or the biologically active fragment thereof comprises or consists of at least 150 contiguous amino acid residues having at least 95% identity to SEQ ID NO: 3, wherein the modified polymerase or biologically active fragment thereof has improved accuracy as compared to SEQ ID NO: 34.

In some embodiments, the modified polymerase or the biologically active fragment thereof comprises or consists of at least 100 contiguous amino acid residues having at least 98% identity to SEQ ID NO: 3, and wherein the modified polymerase or biological active fragment thereof has improved accuracy as compared to SEQ ID NO: 34. In some embodiments, the modified polymerase or the biologically active fragment thereof comprises or consists of at least 150 contiguous amino acid residues having at least 99% identity to SEQ ID NO: 3, wherein the modified polymerase or biologically active fragment thereof has improved accuracy as compared to SEQ ID NO: 34.

In some embodiments, the modified polymerase consists of or comprises an isolated variant of a polymerase having or comprising an amino acid sequence that is at least 80% identical to the amino acid sequence of SEQ ID NO: 4. In some embodiments, the polymerase is a variant of a Taq DNA polymerase comprising an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4. In some embodiments, the reference polymerase is a Taq DNA polymerase consisting of the amino acid sequence of SEQ ID NO: 4 and the modified polymerase includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 4.

In some embodiments, the modified polymerase or the biologically active fragment thereof comprises or consists of at least 100 contiguous amino acid residues having at least 90% identity to SEQ ID NO: 4, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 95% identity to SEQ ID NO: 4, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 98% identity to SEQ ID NO: 4, and wherein the modified polymerase or biological active fragment thereof has improved thermostability as compared to SEQ ID NO: 1. In some embodiments, the modified polymerase or the biologically active fragment thereof comprises or consists of at least 150 contiguous amino acid residues having at least 99% identity to SEQ ID NO: 4, wherein the modified polymerase or biologically active fragment thereof has improved thermostability as compared to SEQ ID NO: 1.

In some embodiments, the modified polymerase or the biologically active fragment thereof comprises or consists of at least 100 contiguous amino acid residues having at least 90% identity to SEQ ID NO: 4, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 95% identity to SEQ ID NO: 4, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 98% identity to SEQ ID NO: 4, and wherein the modified polymerase or biological active fragment thereof has improved accuracy as compared to SEQ ID NO: 1. In some embodiments, the modified polymerase or the biologically active fragment thereof comprises or consists of at least 150 contiguous amino acid residues having at least 99% identity to SEQ ID NO: 4, wherein the modified polymerase or biologically active fragment thereof has improved accuracy as compared to SEQ ID NO: 1.

In some embodiments, the modified polymerase or the biologically active fragment thereof comprises or consists of at least 100 contiguous amino acid residues having at least 90% identity to SEQ ID NO: 4, and wherein the modified polymerase or biological active fragment thereof has improved thermostability as compared to SEQ ID NO: 34. In some embodiments, the modified polymerase or the biologically active fragment thereof comprises or consists of at least 150 contiguous amino acid residues having at least 95% identity to SEQ ID NO: 4, wherein the modified polymerase or biologically active fragment thereof has improved thermostability as compared to SEQ ID NO: 34.

In some embodiments, the modified polymerase or the biologically active fragment thereof comprises or consists of at least 100 contiguous amino acid residues having at least 98% identity to SEQ ID NO: 4, and wherein the modified polymerase or biological active fragment thereof has improved thermostability as compared to SEQ ID NO: 34. In some embodiments, the modified polymerase or the biologically active fragment thereof comprises or consists of at least 150 contiguous amino acid residues having at least 99% identity to SEQ ID NO: 4, wherein the modified polymerase or biologically active fragment thereof has improved thermostability as compared to SEQ ID NO: 34.

In some embodiments, the modified polymerase or the biologically active fragment thereof comprises or consists of at least 100 contiguous amino acid residues having at least 90% identity to SEQ ID NO: 4, and wherein the modified polymerase or biological active fragment thereof has improved accuracy as compared to SEQ ID NO: 34. In some embodiments, the modified polymerase or the biologically active fragment thereof comprises or consists of at least 150 contiguous amino acid residues having at least 95% identity to SEQ ID NO: 4, wherein the modified polymerase or biologically active fragment thereof has improved accuracy as compared to SEQ ID NO: 34.

In some embodiments, the modified polymerase or the biologically active fragment thereof comprises or consists of at least 100 contiguous amino acid residues having at least 98% identity to SEQ ID NO: 4, and wherein the modified polymerase or biological active fragment thereof has improved accuracy as compared to SEQ ID NO: 34. In some embodiments, the modified polymerase or the biologically active fragment thereof comprises or consists of at least 150 contiguous amino acid residues having at least 99% identity to SEQ ID NO: 4, wherein the modified polymerase or biologically active fragment thereof has improved accuracy as compared to SEQ ID NO: 34.

In some embodiments, the disclosure relates generally to a modified polymerase that includes an isolated variant of a Taq DNA polymerase comprising an amino acid sequence selected from the group consisting of: SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure relates generally to a modified polymerase that includes an isolated variant of a Taq DNA polymerase comprising an amino acid sequence selected from the group consisting of: SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33, and further including one or more amino acid substitutions that a not naturally occurring. Optionally, the modified polymerase includes one, two, three, four, five, or more amino acid substitutions relative to the amino acid sequence of SEQ ID NO: 1 or 34.

In some embodiments, the reference polymerase can include a Taq DNA polymerase having, or comprising the amino acid sequence of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; where the modified polymerase comprises a variant of the reference polymerase, thereby the modified polymerase further includes one, two, three, four, five, or more amino acid substitutions relative to the reference polymerase. In some embodiments, the modified polymerase comprises or consists of an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase but is typically less than 100% identical with respect to amino acid sequence. In some embodiments, the one, two, three, four, five, or more amino acid substitutions relative to the reference polymerase can include at least one conservative amino acid substitution.

In some embodiments, the modified polymerase or the biologically active fragment thereof having improved thermostability and/or improved accuracy relative to the reference polymerase (e.g., SEQ ID NO: 1 or SEQ ID NO: 34), comprises or consists of at least 80%, at least 85%, at least 90%, at least 95%, at least 96%, at least 97%, at least 98%, or at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof further comprises at least 25 contiguous amino acids of the polymerase DNA binding domain. In some embodiments, the modified polymerase or the biologically active fragment thereof comprises at least 50 contiguous amino acid residues of the polymerase DNA binding domain. In some embodiments, the modified polymerase or the biologically active fragment thereof comprises or consists of at least 100 contiguous amino acid residues of the polymerase DNA binding domain. In some embodiments, the modified polymerase or the biologically active fragment thereof comprises or consists of at least 100 contiguous amino acid residues of the polymerase DNA binding domain, while also having at least 80%, at least 85%, at least 90%, at least 95%, at least 98%, or at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the modified polymerase or the biologically active fragment thereof comprises or consists of at least 200 contiguous amino acid residues of the polymerase DNA binding domain, while also having at least 80%, at least 85%, at least 90%, at least 95%, at least 98%, or at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a composition comprising an isolated polypeptide having at least 80%, at least 85%, at least 90%, at least 95%, at least 97%, at least 98%, or at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a composition comprising an isolated nucleic acid having at least 80% identity to SEQ ID NO: 1 and further comprising at least one amino acid substitution selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 and L828, wherein the numbering is specific to the numbering of amino acid residues of SEQ ID NO: 1.

In some embodiments, the disclosure is generally related to a composition comprising an isolated nucleic acid having at least 80% identity to SEQ ID NO: 1 and further comprising at least one amino acid substitution selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A, wherein the numbering is specific to the numbering of amino acid residues of SEQ ID NO: 1.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 1 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 2 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 3 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, E790G, E794C and L828A.

In some embodiments, disclosure is generally related to an isolated and purified polypeptide comprising or consisting of at least 80%, at least 85%, at least 90%, at least 95%, at least 97%, at least 98%, or at least 99% identity to SEQ ID NO: 4 and having one or more amino acid mutations selected from the group consisting of P6N, A77E, A97V, L193V, K240I, R266Q, E267T, L287T, P291T, K292C, E295F or E295N, G418C, L490Q, A502S, S543V, D578E, R593G, L678F or L678T, S699W, E713W, V737A, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 5 and having one or more amino acid mutations selected from the group consisting of A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 6 and having one or more amino acid mutations selected from the group consisting of P6N, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 7 and having one or more amino acid mutations selected from the group consisting of P6N, A77E, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 8 and having one or more amino acid mutations selected from the group consisting of P6N, A77E, A97V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 9 and having one or more amino acid mutations selected from the group consisting of P6N, A77E, A97V, L193V, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 10 and having one or more amino acid mutations selected from the group consisting of P6N, A77E, A97V, L193V, K240I, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 11 and having one or more amino acid mutations selected from the group consisting of P6N, A77E, A97V, L193V, K240I, R266Q, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 12 and having one or more amino acid mutations selected from the group consisting of P6N, A77E, A97V, L193V, K240I, R266Q, E267T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 13 and having one or more amino acid mutations selected from the group consisting of P6N, A77E, A97V, L193V, K240I, R266Q, E267T, L287T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 14 and having one or more amino acid mutations selected from the group consisting of P6N, A77E, A97V, L193V, K240I, R266Q, E267T, L287T, P291T, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 15 and having one or more amino acid mutations selected from the group consisting of P6N, A77E, A97V, L193V, K240I, R266Q, E267T, L287T, P291T, K292C, E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 16 and having one or more amino acid mutations selected from the group consisting of P6N, A77E, A97V, L193V, K240I, R266Q, E267T, L287T, P291T, K292C, E295F, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 17 and having one or more amino acid mutations selected from the group consisting of P6N, A77E, A97V, L193V, K240I, R266Q, E267T, L287T, P291T, K292C, E295F or E295N, E397V, L490Q, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 18 and having one or more amino acid mutations selected from the group consisting of P6N, A77E, A97V, L193V, K240I, R266Q, E267T, L287T, P291T, K292C, E295F or E295N, E397V, G418C, A502S, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 19 and having one or more amino acid mutations selected from the group consisting of P6N, A77E, A97V, L193V, K240I, R266Q, E267T, L287T, P291T, K292C, E295F or E295N, E397V, G418C, L490Q, S543V, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 20 and having one or more amino acid mutations selected from the group consisting of P6N, A77E, A97V, L193V, K240I, R266Q, E267T, L287T, P291T, K292C, E295F or E295N, E397V, G418C, L490Q, A502S, D578E, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 21 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, R593G, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 22 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, L678F or L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 23 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678T, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 24 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F, S699W, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 25 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, E713W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 26 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, V737A, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 27 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, E745T, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 28 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, L763F, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 29 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, E790G, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 30 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E794C, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 31 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E805I and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 32 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C and L828A.

In some embodiments, the disclosure is generally related to an isolated and purified polypeptide comprising or consisting of at least 80%, at least 85%, at least 90%, at least 95%, at least 97%, at least 98%, or at least 99% identity to SEQ ID NO: 33 and having one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C and E805I.

In some embodiments, the composition comprises at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 and further comprises at least one amino acid substitution selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 and L828, wherein the numbering is specific to the numbering of amino acid residues of SEQ ID NO: 1. In some embodiments, the amino acid substitution comprises a conservative amino acid a substitution.

In some embodiments, the composition comprises at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 and further comprises at least one amino acid substitution selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A, wherein the numbering is specific to the numbering of amino acid residues of SEQ ID NO: 1.

In some embodiments, the composition comprises at least 85%, at least 90%, at least 95%, at least 98% or at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33, and further comprising at least one amino acid substitution selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A, wherein the numbering is specific to the numbering of amino acid residues of SEQ ID NO: 1.

In some embodiments, the modified polymerase can include anyone or more amino acid substitutions selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A, wherein the numbering is relative to the amino acid sequence of SEQ ID NO: 1. In some embodiments, the modified polymerase has improved accuracy and/or improved thermostability relative to the reference polymerase. Without being bound to any particular theory of operation, it can be observed that in some embodiments one or more of the aforementioned substitutions can alter, e.g., increase or decrease the accuracy or thermostability of the modified polymerase relative to a reference (e.g., unmodified) polymerase. In some embodiments, such increase in accuracy and/or thermostability can be observed as an increase in signal produced an ion-based sequencing reaction.

In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 1 or SEQ ID NO: 34.

In some embodiments, the disclosure is generally related to an isolated nucleic acid sequence comprising or consisting of a nucleic acid sequencing encoding a polypeptide having at least 80%, at least 85%, at least 90%, at least 95%, at least 97%, at least 98%, or at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a composition comprising an isolated nucleic acid sequence comprising or consisting of a nucleic acid sequence encoding a polypeptide having at least 80%, at least 85%, at least 90%, at least 95%, at least 97%, at least 98%, or at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33, and further comprising one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A.

In some embodiments, the disclosure is generally related to a vector comprising an isolated nucleic sequence encoding a polypeptide or a biologically active fragment thereof selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33. In some embodiments, the vector comprising the isolated nucleic acid sequence encoding a polypeptide or biologically active fragment thereof includes a DNA polymerase. In some embodiments, the DNA polymerase is a *Thermus aquaticus* (Taq) polymerase. In some embodiments, the DNA polymerase is a thermostable DNA polymerase. In some embodiments, the DNA polymerase is derived from a thermostable *Thermus aquaticus* (Taq) polymerase.

In some embodiments, the disclosure is generally related to a vector comprising an isolated nucleic acid sequence encoding a polypeptide or a biologically active fragment thereof that comprises a homolog of Taq DNA polymerase, wherein the homolog of Taq DNA polymerase includes at least one amino acid substitution corresponding to the amino acid substitutions present in any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure is generally related to a kit comprising an isolated polypeptide having at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the kit comprises an isolated polypeptide having at least 90%, at least 95%, at least 96%, at least 97%, at least 98% or at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the kit comprises an isolated polypeptide comprising or consisting of at least 250, at least 300, at least 350, at least 400, at least 450, at least 500, at least 550, at least 600, or at least 650 contiguous amino acid residues having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the kit further includes one or more suitable buffers, MgCl and dNTPs.

In some embodiments, the disclosure generally relates to a system (and related apparatus, kits, methods and compositions) for amplifying one or more nucleic acids. In some embodiments, the system can comprise a DNA polymerase having at least one mutation (e.g., substitution, insertion, deletion, fusion, and the like) as compared to the amino acid sequence of SEQ ID NO: 1 or SEQ ID NO: 34; a solid support comprising a nucleic acid molecule to be amplified; a mixture of nucleotides (e.g., dNTP, ddNTPs, and the like); and conditions under which the nucleic acid molecule is amplified on the solid support. In some embodiments, the amplification can include clonal amplification or bridge-PCR amplification. In some embodiments, the amplification can include proximity ligation amplification, rolling circle amplification, PCR amplification, isothermal amplification, recombinase polymerase amplification, strand displacement amplification, emulsion PCR amplification, and the like. In illustrative embodiments, the DNA polymerase is a modified polymerase that includes any of the following mutations: P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A, wherein the numbering is relative to the amino acid sequence of SEQ ID NO: 1.

In some embodiments, the disclosure generally relates to a polymerase or a biologically active fragment thereof having DNA polymerase activity and at least 80%, at least 90%, at least 95%, at least 96%, at least 97%, at least 98% or at least 99% identity identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33, wherein the polymerase or the biologically active fragment having DNA polymerase activity includes at least one amino acid substitution as compared to SEQ ID NO: 1 or SEQ ID NO: 34. In some embodiments the polymerase or biologically active fragment thereof includes at least two, three, four, five, or more amino acid substitutions as compared to SEQ ID NO: 1 or SEQ ID NO: 34.

In some embodiments, the at least one amino acid substitution as compared to SEQ ID NO: 1 or SEQ ID NO: 34 can impart a beneficial property to the polymerase or biologically active fragment thereof. In some embodiments, the beneficial property imparted to the polymerase or biologically active fragment thereof (as compared to SEQ ID NO: 1 or SEQ ID NO: 34) includes improved thermostability, improved read length, improved templating efficiency, improved performance in a high ionic strength solution or improved accuracy. In some embodiments, the beneficial property imparted to the polymerase or biologically active fragment thereof (as compared to SEQ ID NO: 1 or SEQ ID NO: 34) includes reduced strand bias of GC and AT rich nucleic acids. It will be generally understood to those of ordinary skill in the art that the beneficial property imparted to the polymerase or biological fragment (as compared to the properties of SEQ ID NO: 1 or SEQ ID NO: 34) can be determined by assessing and/or measuring such beneficial properties under identical conditions by any appropriate means (e.g., comparing the properties of SEQ ID NO: 1 against the polymerase or biologically active fragment thereof under identical conditions). For example, the accuracy of a DNA polymerase can be measured in terms of the longest perfect read (typically measured in terms of the number of nucleotides correctly included in the read) obtained from a nucleotide polymerization reaction. In some embodiments, the nucleotide polymerization reaction can be conducted using emulsion PCR, bridge PCR or hot-start PCR conditions. In some embodiments, one or more of the beneficial properties imparted to the polymerase or biologically active fragment thereof can be determined by assessing sequencing accuracy. In some embodiments, sequencing accuracy can be determined using any next-generation (i.e. massively parallel, high throughput) sequencing platform (e.g., Ion Torrent Systems, Illumina HiSeq or True Seq or X-10 systems). In some embodiments, sequencing accuracy can be determined using any ISFET based sequencing system. However, it will be apparent that other appropriate methods to determine improved thermostability and/or improved accuracy may be used and are contemplated within the scope of the present disclosure.

In some embodiments, the disclosure generally relates to a substantially purified polymerase having an amino acid sequence comprising or consisting of a biologically active fragment of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 that retains polymerase activity. In some embodiments, the polymerase activity, characteristic, or property is selected from primer extension activity, strand displacement activity, proofreading activity, nick-initiated polymerase activity, reverse transcriptase activity, accuracy, average read length, thermostability, processivity, strand bias or nucleotide polymerization activity. In some embodiments, the polymerase activity, characteristic, or property is selected from one or more sequencing based metrics selected from raw read accuracy, average read length, thermostability or processivity.

In some embodiments, the disclosure generally relates to a substantially purified polymerase having an amino acid sequence comprising or consisting of a biologically active fragment of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 having polymerase activity selected from improved read length, improved accuracy or improved thermostability as compared to polymerase activity of SEQ ID NO: 1 or SEQ ID NO: 34 under identical conditions. In some embodiments, the polymerase activity is determined in the presence of a high ionic strength solution. In some embodiments the high ionic strength solution is at least 120 mM Kcl. In some embodiments, the high ionic strength solution is from 125 mM KCl to 200 mM KCl.

In some embodiments, the disclosure generally relates to a substantially purified polymerase having an amino acid sequence comprising or consisting of at least 90% identity to SEQ ID NO: 1 and further comprising a E397 amino acid substitution, wherein the numbering is relative to SEQ ID NO: 1. In some embodiments, the disclosure generally relates to a substantially purified polymerase having an amino acid sequence comprising or consisting of at least 90% identity to SEQ ID NO: 1 and further comprising a E397V amino acid substitution, wherein the numbering is relative to SEQ ID NO: 1.

In some embodiments, the disclosure generally relates to a substantially purified polymerase having an amino acid sequence comprising or consisting of at least 90% identity to SEQ ID NO: 1 and further comprising a L763 amino acid substitution, wherein the numbering is relative to SEQ ID NO: 1. In some embodiments, the disclosure generally relates to a substantially purified polymerase having an amino acid sequence comprising or consisting of at least 90% identity to SEQ ID NO: 1 and further comprising a L763F amino acid substitution, wherein the numbering is relative to SEQ ID NO: 1.

In some embodiments, the disclosure generally relates to a substantially purified polymerase having an amino acid sequence comprising or consisting of at least 90% identity to SEQ ID NO: 1 and further comprising a E805 amino acid substitution, wherein the numbering is relative to SEQ ID NO: 1. In some embodiments, the disclosure generally relates to a substantially purified polymerase having an amino acid sequence comprising or consisting of at least 90% identity to SEQ ID NO: 1 and further comprising a E805I amino acid substitution, wherein the numbering is relative to SEQ ID NO: 1.

In some embodiments, the disclosure generally relates to a substantially purified polymerase having an amino acid sequence comprising or consisting of at least 90% identity to SEQ ID NO: 1 and further comprising a E745 amino acid substitution, wherein the numbering is relative to SEQ ID NO: 1. In some embodiments, the disclosure generally relates to a substantially purified polymerase having an amino acid sequence comprising or consisting of at least 90% identity to SEQ ID NO: 1 and further comprising a E745T amino acid substitution, wherein the numbering is relative to SEQ ID NO: 1.

In some embodiments, the disclosure generally relates to a substantially purified polymerase having an amino acid sequence comprising or consisting of at least 90% identity to SEQ ID NO: 34 and further comprising a E397 amino acid substitution, wherein the numbering is relative to SEQ ID NO: 34. In some embodiments, the disclosure generally relates to a substantially purified polymerase having an amino acid sequence comprising or consisting of at least 90% identity to SEQ ID NO: 34 and further comprising a E397V amino acid substitution, wherein the numbering is relative to SEQ ID NO: 34.

In some embodiments, the disclosure generally relates to a substantially purified polymerase having an amino acid sequence comprising or consisting of at least 90% identity to SEQ ID NO: 34 and further comprising a L763 amino acid substitution, wherein the numbering is relative to SEQ ID NO: 34. In some embodiments, the disclosure generally relates to a substantially purified polymerase having an amino acid sequence comprising or consisting of at least 90% identity to SEQ ID NO: 34 and further comprising a L763F amino acid substitution, wherein the numbering is relative to SEQ ID NO: 34.

In some embodiments, the disclosure generally relates to a substantially purified polymerase having an amino acid sequence comprising or consisting of at least 90% identity to SEQ ID NO: 34 and further comprising a E805 amino acid substitution, wherein the numbering is relative to SEQ ID NO: 34. In some embodiments, the disclosure generally relates to a substantially purified polymerase having an amino acid sequence comprising or consisting of at least 90% identity to SEQ ID NO: 34 and further comprising a E805 amino acid substitution, wherein the numbering is relative to SEQ ID NO: 34.

In some embodiments, the disclosure generally relates to a substantially purified polymerase having an amino acid sequence comprising or consisting of at least 90% identity to SEQ ID NO: 34 and further comprising a E745 amino acid substitution, wherein the numbering is relative to SEQ ID NO: 34. In some embodiments, the disclosure generally relates to a substantially purified polymerase having an amino acid sequence comprising or consisting of at least 90% identity to SEQ ID NO: 34 and further comprising a E745T amino acid substitution, wherein the numbering is relative to SEQ ID NO: 34.

In some embodiments, the disclosure generally relates to a substantially purified polymerase having an amino acid sequence comprising or consisting of at least 90% identity to SEQ ID NO: 1 and further comprising E397, E745 and L763 amino acid substitutions, wherein the numbering is relative to SEQ ID NO: 1. In some embodiments, the disclosure generally relates to a substantially purified polymerase having an amino acid sequence comprising or consisting of at least 90% identity to SEQ ID NO: 1 and further comprising E397V, E745T and L763F amino acid substitutions, wherein the numbering is relative to SEQ ID NO: 1.

In some embodiments, the disclosure generally relates to a substantially purified polymerase having an amino acid sequence comprising or consisting of at least 90% identity to SEQ ID NO: 34 and further comprising E397, E745 and L763 amino acid substitutions, wherein the numbering is relative to SEQ ID NO: 34. In some embodiments, the disclosure generally relates to a substantially purified polymerase having an amino acid sequence comprising or consisting of at least 90% identity to SEQ ID NO: 34 and further comprising E397V, E745T and L763F amino acid substitutions, wherein the numbering is relative to SEQ ID NO: 34.

In some embodiments, the disclosure generally relates to a substantially purified polymerase having an amino acid sequence comprising or consisting of at least 90% identity to SEQ ID NO: 1 and further comprising E805 and L763 amino acid substitutions, wherein the numbering is relative to SEQ ID NO: 1. In some embodiments, the disclosure generally relates to a substantially purified polymerase having an amino acid sequence comprising or consisting of at least 90% identity to SEQ ID NO: 1 and further comprising E805I and L763F amino acid substitutions, wherein the numbering is relative to SEQ ID NO: 1.

In some embodiments, the disclosure generally relates to a substantially purified polymerase having an amino acid sequence comprising or consisting of at least 90% identity to SEQ ID NO: 34 and further comprising E805 and L763 amino acid substitutions, wherein the numbering is relative to SEQ ID NO: 34. In some embodiments, the disclosure generally relates to a substantially purified polymerase having an amino acid sequence comprising or consisting of at least 90% identity to SEQ ID NO: 34 and further comprising E805I and L763F amino acid substitutions, wherein the numbering is relative to SEQ ID NO: 34.

In some embodiments, the reference polymerase has or comprises the amino acid sequence of SEQ ID NO: 2, SEQ ID NO: 3 or SEQ ID NO: 4, and the modified polymerase has or comprises the amino acid sequence of the reference polymerase, further including one or more amino acid mutations as compared to the reference polymerase. In some embodiments, the amino acid mutations include a substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 1. In some embodiments, the modified polymerase exhibits a change in any one or more parameters selected from the group consisting of: average read length, accuracy, total sequencing throughout, strand bias, lowered systematic error, enhanced polymerase performance in high ionic strength solution, improved processivity, improved performance in PCR, performance in emulsion PCR, relative to the reference polymerase. Optionally, the change in any one or more parameters is observed by comparing the performance of the reference and modified polymerases in an ion-based sequencing reaction.

Without being bound to any particular theory of operation, it can be observed that in some embodiments a modified polymerase including one or more of the disclosed amino acid substitutions exhibits an altered (e.g., increased) processivity relative to an unmodified polymerase, or an altered (e.g., decreased) strand bias relative to the unmodified polymerase. In some embodiments, the modified polymerase exhibits an altered (e.g., increased) accuracy relative to the unmodified polymerase. In some embodiments, the modified polymerase exhibits an altered, (e.g., increased) average error-free read length, or altered (e.g., increased) observed 100Q17 or 200Q17 values relative to the reference polymerase. In some embodiments, the modified polymerase has polymerase activity. In some embodiments, the modified polymerase or biologically active fragment can have primer extension activity in vivo or in vitro.

In some embodiments, the one or more mutations in the modified polymerase can include at least one amino acid substitution. The at least one amino acid substitution can optionally occur at any one or more positions selected from the group consisting of P6, A77, A97, L193, K240, R266, E267, L287, P291, K292, E295, E397, G418, L490, A502, S543, D578, R593, L678, S699, E713, V737, E745, L763, E790, E794, E805 and L828, wherein the numbering is relative to the amino acid sequence of SEQ ID NO: 1. In some embodiments, the modified polymerase includes at least two, three, four, five, or more amino acid substitutions occurring at positions selected from this group. In some embodiments, the at least one amino acid substitution can optionally occur at any one or more positions selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805 and L828A, wherein the numbering is relative to the amino acid sequence of SEQ ID NO: 1. In some embodiments, the modified polymerase includes at least two, three, four, five, or more amino acid substitutions occurring at positions selected from this group.

Without being bound to any particular theory of operation, it can be observed that in some embodiments a modified polymerase including any one of such amino acid substitutions exhibits an altered (e.g., increased or decreased) thermostability relative to an unmodified polymerase, or altered (e.g., increased or decreased) accuracy relative to the corresponding unmodified polymerase, or relative to the reference polymerase. It will be apparent to one of ordinary skill in the art, that some amino acid residues of the modified polymerase may be highly conserved amino acid residues. It is anticipated that one of ordinary skill in the art can construct, express, and determine which amino acid residues, if any, in a given polymerase are highly conserved by well known means (for example, see U.S. Pat. Nos.

5,436,149; 6,395,524; 6,982,144; 7,312,059 and 8,420,325, all of which are incorporated herein in their entireties).

In some embodiments, the modified polymerase can include aTaq DNA polymerase. In some embodiments, the polymerase can include a Taq DNA polymerase commercially available as Platinum Taq High Fidelity DNA polymerase (Life Technologies, CA), that includes one or more amino acid mutations as compared to the reference polymerase. In some embodiments, the modified polymerase can include a Taq DNA polymerase having, or comprising, the amino acid sequence of SEQ ID NO: 1, which is the amino acid sequence of the wild-type Taq DNA polymerase.

In some embodiments, the modified polymerase includes a mutant or variant form of a Taq DNA polymerase that retains a detectable level of polymerase activity. In order to retain the polymerase activity of the Taq DNA polymerase, any substitutions, deletions or chemical modifications will be made to amino acid residues that are not highly conserved, such as the invariant aspartic acid residues required for polymerase activity. In some embodiments, the modified polymerase can include Taq DNA polymerase, a hot-start Taq DNA polymerase, a chemical hot-start Taq DNA polymerase, a Platinium Taq DNA polymerase and the like.

In some embodiments, the modified polymerase can include an isolated variant of a polymerase having or comprising an amino acid sequence that is at least 90% identical to the amino acid sequence of SEQ ID NO: 2. In some embodiments, the polymerase is a variant of a Taq DNA polymerase comprising the amino acid sequence of SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the modified polymerase includes a mutant or variant form of Taq DNA polymerase having amino acid mutation E397V, wherein the numbering is relative to the amino acid sequence of SEQ ID NO: 1. In some embodiments, the modified Taq DNA polymerase can include amino acid mutation L763F, wherein the numbering is relative to the amino acid sequence of SEQ ID NO: 1. In some embodiments, the modified Taq DNA polymerase can include amino acid mutation E805I, wherein the numbering is relative to the amino acid sequence of SEQ ID NO: 1. In some embodiments, the modified Taq DNA polymerase can include amino acid mutation E745T, wherein the numbering is relative to the amino acid sequence of SEQ ID NO: 1. In some embodiments, the modified Taq DNA polymerase can include amino acid mutation A97V, wherein the numbering is relative to the amino acid sequence of SEQ ID NO: 1. In some embodiments, the modified Taq DNA polymerase can include amino acid mutation E295F, wherein the numbering is relative to the amino acid sequence of SEQ ID NO: 1. In some embodiments, the modified Taq DNA polymerase can include amino acid mutation P6N, wherein the numbering is relative to the amino acid sequence of SEQ ID NO: 1. In some embodiments a modified polymerase including one or more of the above mutations exhibits altered (e.g., increased or decreased) accuracy relative to the corresponding reference polymerase (e.g., unmodified polymerase SEQ ID NO: 1). In some embodiments, the modified Taq polymerase has an altered (e.g., increased or decreased) thermostability relative to the reference polymerase (e.g., unmodified polymerase SEQ ID NO: 1). In some embodiments, the modified Taq polymerase exhibits an altered (e.g., increased or decreased) read length, or an altered (e.g., increased or decreased) strand bias, or altered (e.g., increased or decreased) processivity, or altered systematic error (e.g., increased or decreased), or altered (e.g., increased or decreased) observed 100Q17 or 200Q17 values, or altered (e.g., increased or decreased) AQ17 or AQ20 values relative to the reference polymerase.

In some embodiments, the modified Taq polymerase exhibits a change in any one or more of the following parameters: average read length, performance in high ionic strength solution, improved processivity, improved templating efficiency, improved thermostability, improved performance in emulsion PCR, reduced strand bias in GC or AT rich sequences, or reduced systematic error relative to the reference polymerase. In one embodiment, the change in one or more of the parameters is observed by comparing the performance of the reference polymerase and modified polymerase under identical conditions. Optionally, the change in one or more parameters can be observed using in an ion-based sequencing reaction.

In some embodiments, the modified polymerase can include at least one amino acid substitution of an existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified Taq polymerase, or both the reference and modified Taq polymerase can further include a deletion of the methionine residue at position 1, or a substitution of the methionine residue at position 1 with any other amino acid residue, wherein the numbering is relative to the amino acid sequence of SEQ ID NO: 1

As the skilled artisan will readily appreciate, the scope of the present disclosure encompasses not only the specific amino acid and/or nucleotide sequences disclosed herein, but also, for example, many related sequences encoding genes and/or peptides with the functional properties described herein. For example, the scope and spirit of the disclosure encompasses any nucleotide and amino acid sequences encoding conservative variants of the various polymerases disclosed herein. It will also be readily apparent to the skilled artisan that the modified polymerases disclosed herein by amino acid sequence can be converted to the corresponding nucleotide sequence without undue experimentation, for example using a number of freely available sequence conversion applications (e.g., "in-silco").

It is anticipated that one of skill in the art, having identified one or more amino acid substitutions disclosed herein which impart a beneficial property to the modified polymerase (such as improved thermostability, improved accuracy, improved processivity, improved read length as compared to a reference polymerase) can be transferred to different polymerase species or polymerase family without undue experimentation. As a result, once an amino acid mutation is identified in a polymerase that provides altered catalytic or kinetic properties, the amino acid mutation can be screened using methods known to one of ordinary skill in the art (such as amino acid or nucleotide sequence alignment), to determine if the amino acid mutation can be readily transferred to a different polymerase, such as a different species, class or polymerase family. In some embodiments, the transferable (or homologous) amino acid mutation can include an amino acid mutation that enhances properties such as increased read-length, increased raw accuracy, decreased strand bias, reduced systematic error, increased total sequencing throughput, increased error-free read length, increased processivity, increased AQ values, and the like. In some embodiments, a transferable (or homologous) amino acid mutation can include transferring one or more amino acid mutations to another polymerase within, or between, DNA polymerase families, such as DNA polymerase family A or DNA polymerase family B. In some embodiments, a transferable (or homologous) amino acid mutation can include transferring one or more amino acid mutations to one or more polymerases within, or between, DNA polymerase families, such as across bacterial, viral, archaeal, eukaryotic or phage DNA polymerases.

In some embodiments, a modified polymerase according to the disclosure can include a polymerase having one or more amino acid mutations (such as a substitution, insertion, or deletion) that are homologous (a homolog) to one or more of the amino acid mutations disclosed herein. For example, the disclosure includes with its scope, a modified polymerase having one or more amino acid mutations that are homologous to any one of the amino acid mutations provided in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33. In some embodiments, a modified polymerase according to the disclosure can include any polymerase having one or more amino acid mutations that are homologous to one or more amino acid mutations provided herein for Taq DNA polymerase (e.g., one or more homologous amino acid mutations that correspond to one or more amino acid mutations of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33). One method for determining whether a polymerase is a homolog of one or more of the modified polymerases disclosed herein, includes comparing the amino acid or nucleic acid sequence alignment of the modified polymerase against the "test" polymerase. For example, the National Center for Biotechnology Information (NCBI) provides a variety of electronic databases (e.g., "HomoloGene" and "Protein Clusters") that allows a user to determine whether an amino acid sequence is present as a homolog in another organism.

In some embodiments, a modified polymerase or a biologically active fragment of a polymerase according to the disclosure can include a polymerase having one or more amino acid mutations that are homologous to one or more amino acid mutations of Taq DNA polymerase including, any one or more amino acid mutations selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A, wherein the numbering is relative to the amino acid sequence of SEQ ID NO: 1.

In some embodiments, the modified polymerase or a biologically active fragment thereof includes two, three, four, five, or more amino acid mutations that are homologous to any two, three, four, five, or more amino acid substitutions selected from the group consisting of P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A, wherein the numbering is relative to the amino acid sequence of SEQ ID NO: 1.

In some embodiments, a modified polymerase or any biologically active fragment of a polymerase having one or more amino acid mutations that are homologous to an amino acid mutation disclosed herein for Taq DNA polymerase can optionally include at least one amino acid substitution designed to replace a non-cysteine amino acid residue with a cysteine residue. A person of ordinary skill will be readily able to determine nucleotide sequences that encode any of the amino acid sequences of the disclosure based on the known correspondence between the nucleotide sequence and a corresponding protein sequence.

In some embodiments, the modified polymerase or any biologically active fragment of a polymerase can include one or more biotin moieties. As used herein, the terms "biotin" and "biotin moiety" and their variants comprise biotin (cis-hexahydro-2-oxo-1H-thieno[3,4]imidazole-4-pentanoic acid) and any derivatives and analogs thereof, including biotin-like compounds. Such compounds include, for example, biotin-ε-N-lysine, biocytin hydrazide, amino or sulfhydryl derivatives of 2-iminobiotin and biotinyl-ε-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin, and the like, as well as any biotin variants that can specifically bind to an avidin moiety. The terms "avidin" and "avidin moiety" and their variants, as used herein, comprise the native egg-white glycoprotein avidin, as well as any derivatives, analogs and other non-native forms of avidin, which can specifically bind to biotin moieties. In some embodiments, the avidin moiety can comprise deglycosylated forms of avidin, bacterial streptavidins produced by selected strains of Streptomyces, e.g., Streptomyces avidinii, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin®, Captavidin®, Neutravidin® and Neutralite Avidin®. All forms of avidin-type molecules, including both native and recombinant avidin and streptavidin as well as derivatized molecules, e.g. nonglycosylated avidins, N-acyl avidins and truncated streptavidins, are encompassed within the terms "avidin" and "avidin moiety". Typically, but not necessarily, avidin exists as a tetrameric protein, wherein each of the four tetramers is capable of binding at least one biotin moiety. As used herein, the term "biotin-avidin bond" and its variants refers to a specific linkage formed between a biotin moiety and an avidin moiety. Typically, a biotin moiety can bind with high affinity to an avidin moiety, with a dissociation constant $K_d$ typically in the order of $10^{-4}$ to $10^{-15}$ mol/L. Typically, such binding occurs via non-covalent interactions.

In some embodiments, the modified polymerase or any biologically active fragment of a polymerase can include one or more modified or substituted amino acids relative to the unmodified or reference polymerase, and can further include a biotin moiety that is linked to at least one of the one or more modified or substituted amino acids. The biotin moiety can be linked to the modified polymerase using any suitable linking method. In some embodiments, the modified polymerase includes one or more cysteine replacement substitutions, and the linking moiety includes a biotin moiety that is linked to at least one of the one or more cysteine replacement substitutions. In some embodiments, the modified polymerase can be chemically modified to be reversibly inactivated such that it is activated with heat (see e.g., U.S. Pat. No. 5,677,152, Birch et al.). In these embodiments, the modified polymerase is well suited for a hot start amplification method, such as a hot start PCR method.

In some embodiments, the modified polymerase is a biotinylated polymerase. The term "biotinylated" and its variants, as used herein, refer to any covalent or non-covalent adduct of biotin with other moieties such as biomolecules, e.g., proteins, nucleic acids (including DNA, RNA, DNA/RNA chimeric molecules, nucleic acid analogs and peptide nucleic acids), proteins (including enzymes, peptides and antibodies), carbohydrates, lipids, etc.

In some embodiments, the disclosure also relates generally to compositions (as well as related methods, kits, systems and apparatuses) comprising a modified polymerase including at least one amino acid modification relative to a reference polymerase, wherein the modified polymerase has improved processivity, improved thermostability and/or improved accuracy relative to a reference polymerase.

In some embodiments, the disclosure relates generally to a method for incorporating at least one nucleotide into a primer, comprising: contacting a nucleic acid complex including a template nucleic acid with primer and a modified polymerase in the presence of one or more nucleotides, and incorporating at least one of the one or more nucleotides into the primer in a template-dependent fashion using said modified polymerase.

Methods for nucleotide incorporation are well known in the art and typically comprise use of a polymerase reaction mixture in which the polymerase is contacted with the template nucleic acid under nucleotide incorporation conditions. When the nucleotide incorporation reaction comprises polymerization of nucleotides onto the end of a primer, the process is typically referred to as "primer extension." Typically, but not necessarily such nucleotide incorporation occurs in a template-dependent fashion. Primer extension and other nucleotide incorporation assays are typically performed by contacting the template nucleic acid with a polymerase in the presence of nucleotides in an aqueous solution under nucleotide incorporation conditions. In some embodiments, the nucleotide incorporation reaction can include a primer, which can optionally hybridize to the template to form a primer-template duplex. Typical nucleotide incorporation conditions are achieved once the template, polymerase, nucleotides and optionally primer are mixed with each other in a suitable aqueous formulation, thereby forming a nucleotide incorporation reaction mixture (or primer extension mixture). The aqueous formulation can optionally include divalent cations and/or salts, particularly $Mg^{++}$ and/or $Ca^{++}$ ions. The aqueous formulation can optionally include divalent anions and/or salts, particularly $SO_4^{2-}$. Typical nucleotide incorporation conditions have included well known parameters for time, temperature, pH, reagents, buffers, reagents, salts, co-factors, nucleotides, target DNA, primer DNA, enzymes such as nucleic acid-dependent polymerase, amounts and/or ratios of the components in the reactions, and the like. The reagents or buffers can include a source of monovalent ions, such as KCl, K-acetate, $NH_4$-acetate, K-glutamate, $NH_4Cl$, or ammonium sulfate. The reagents or buffers can include a source of divalent ions, such as $Mg^{2+}$ and/or $Mn^{2+}$, $MgCl_2$, or Mg-acetate. In some embodiments, the reagents or buffers can include a source of detergent such as Triton and/or Tween. Most polymerases exhibit some levels of nucleotide incorporation activity over a pH range of about 5.0 to about 9.5, more typically between about pH 7 and about pH 9, sometimes between about pH 6 to about pH 8, and sometimes between pH 7 and 8. In some embodiments, a nucleotide polymerization buffer can include chelating agents such as EDTA and/or EGTA, and the like. Although in some embodiments, nucleotide incorporation reactions may include buffering agents, such as Tris, Tricine, HEPES, MOPS, ACES, or MES, which can provide a pH range of about 5.0 to about 9.5, such buffering agents can optionally be reduced or eliminated when performing ion-based reactions requiring detection of ion byproducts. In some embodiments, the nucleotide incorporation reaction may include trehalose. Methods of performing nucleic acid synthesis are well known and extensively practiced in the art and references teaching a wide range of nucleic acid synthesis techniques are readily available. Some exemplary teachings regarding the performance of nucleic acid synthesis (including, for example, template-dependent nucleotide incorporation, as well as primer extension methods) can be found, for example, in Kim et al., Nature 376: 612-616 (2002); Ichida et al., Nucleic Acids Res. 33: 5214-5222 (2005); Pandey et al., European Journal of Biochemistry, 214:59-65 (1993); Blanco et al., J. Biol. Chem. 268: 16763-16770 (1993); U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617; U.S. patent application Ser. No. 12/748,359, now published as U.S. Patent Publication No. 20110014612. Given the ample teaching of primer extension and other nucleotide incorporation reactions in the art, suitable reaction conditions for using the modified polymerases of the disclosure to perform nucleotide incorporation will be readily apparent to the skilled artisan. In some embodiments, the methods (and related kits, apparatus, systems and compositions) can include incorporation of one or more nucleotide analogs and/or reversible terminators.

In some embodiments, the disclosure relates generally to reagents (e.g., buffer compositions) and kits useful for performance of nucleotide polymerization reactions using polymerases, including any of the exemplary modified polymerases described here. The nucleotide polymerization reactions can include without limitation nucleotide incorporation reactions (including both template-dependent and template-independent nucleotide incorporation reactions) as well as primer extension reactions. In some embodiments, the buffer composition can include any one or more of the following: a monovalent metal salt, a divalent metal salt, a divalent anion, and a detergent. For example, the buffer composition can include a potassium or sodium salt. In some embodiments, the buffer composition can include a manganese or magnesium salt. In some embodiments, the buffer composition can include a sulfate such as potassium sulfate and/or magnesium sulfate. In some embodiments, the buffer composition can include a detergent. In some embodiments, the buffer compositions can include a detergent selected from the group consisting of Triton and Tween. In some embodiments, the buffer can include a reagent for a hot start amplification step, such as an oligonucleotide or aptamer.

In some embodiments, the buffer composition can include at least one potassium salt, at least one manganese salt, and Triton X-100 (Pierce Biochemicals). The salt can optionally include a chloride salt or a sulfate salt. In some embodiments, the buffer composition can include a pH of about 7.3 to about 8.0. In some embodiments, the buffer composition can include a pH of about 7.4 to about 7.9. In some embodiments, the buffer composition includes a potassium salt at concentrations of between 5-250 mM, 50-225 mM, 125-200 mM (depending on the divalent).

In some embodiments, the buffer composition includes magnesium or manganese salt at a concentration of between 1 mM and 20 mM. In some embodiments, the buffer composition includes magnesium or manganese salt at a concentration of between 6-15 mM.

In some embodiments, the buffer composition includes a sulfate at a concentration of between 1 mM and 100 mM. In some embodiments, the buffer composition includes a sulfate at a concentration of between 5-50 mM.

In some embodiments, the buffer composition includes a detergent (e.g., Triton X-100 or Tween-20) at a concentration of between 0.001% to 1%. In some embodiments, the buffer composition includes a detergent (e.g., Triton X-100 or Tween-20) at a concentration of between 0.0025-0.0125%.

In some embodiments, the disclosed modified polymerase compositions, (as well as related methods, systems, apparatuses and kits) can be used to obtain sequence information from a nucleic acid molecule. Many methods of obtaining sequence information from a nucleic acid molecule are known in the art, and it will be readily appreciated that all such methods are within the scope of the present disclosure. Suitable methods of sequencing using the disclosed modified polymerases include without limitation: Sanger sequencing, ligation-based sequencing (also known as sequencing by hybridization) and sequencing by synthesis. Sequencing-by-synthesis methods typically involve template-dependent nucleic acid synthesis (e.g., using a primer that is hybridized to a template nucleic acid or a self-priming template, as will be appreciated by those of ordinary skill), based on the sequence of a template nucleic acid. That is, the sequence of the newly synthesized nucleic acid strand is typically complementary to the sequence of the template nucleic acid and therefore knowledge of the order and identity of nucleotide incorporation into the synthesized strand can provide information about the sequence of the template nucleic acid strand. Sequencing by synthesis using the modified polymerases of the disclosure will typically involve detecting the order and/or identity of nucleotide incorporation when nucleotides are polymerized in a template-dependent fashion by the modified polymerase. In some embodiments, sequencing-by-synthesis can include optical single molecule sequencing (e.g., sequencing in the absence of labeled nucleotides). Alternatively, some exemplary methods of sequence-by-synthesis using labeled nucleotides include single molecule sequencing (see, e.g., U.S. Pat. Nos. 7,329,492 and 7,033,764), which typically involve the use of labeled nucleotides to detecting nucleotide incorporation. In some embodiments, the disclosed polymerase compositions (and related methods, kits, systems and apparatuses) can be used to obtain sequence information. In some embodiments, the disclosed modified polymerase can be used to obtain sequence information for whole genome sequencing, amplicon sequencing, targeted re-sequencing, single molecule sequencing, multiplex and/or barcoded sequencing, or paired end sequencing applications, and the like.

In some embodiments, the disclosed modified polymerase compositions as well as related methods, systems, apparatuses and kits, can be used to amplify nucleic acid molecules. In some embodiments, a nucleic acid molecule can be amplified using a modified polymerase by any appropriate method. In some embodiments, a nucleic acid molecule can be amplified for example by pyrosequencing, ion-based ISFET sequencing, PCR, emulsion PCR or bridge polymerase chain reaction.

In some embodiments, the disclosed modified polymerase compositions (as well as related methods, systems, apparatuses and kits) can be used to generate nucleic acid libraries. In some embodiments, the disclosed modified polymerase compositions can be used to generate nucleic acid libraries for a variety of downstream processes. Many methods for generating nucleic acid libraries are known in the art, and it will be readily appreciated that all such methods are within the scope of the present disclosure. Suitable methods include, without limitation, nucleic acid libraries generated using emulsion PCR, bridge PCR, PCR, qPCR, RT-PCR, nested patch PCR, and other forms of nucleic acid amplification dependent on polymerization. In some embodiments, the methods can include template-dependent nucleic acid amplification. In some embodiments, the methods can include a primer:template duplex or a nucleic acid template to which the modified polymerase can perform nucleotide incorporation. In some embodiments, the nucleic acid can include a single stranded nucleic acid with a secondary structure such as a hair-pin or stem-loop that can provide a single-stranded overhang to which the modified polymerase can incorporate a nucleotide during polymerization. In some embodiments, methods for generating nucleic acid libraries using one or more of modified polymerases according to the disclosure can include the generation of a nucleic acid library of 50, 100, 200, 300, 400, 500, 600, 700, 800, or more base pairs in length. In some embodiments, the nucleic acid template to which the modified polymerase can perform nucleotide incorporation can be attached, linked or bound to a support, such as a solid support. In some embodiments, the support can include a planar support such as slide or flowcell. In some embodiments, the support can include a particle, such as a nucleic acid sequencing bead (e.g., an Ion Sphere™ particle (Life Technologies Corp., CA).

In some embodiments, the disclosure relates generally to a method for generating a nucleic acid library comprising contacting a nucleic acid template with a modified polymerase and one or more dNTPs under polymerizing conditions; thereby incorporating one or more dNTPs into the nucleic acid template to generate the nucleic acid library. In some embodiments, the method can further include generating a nucleic acid library or sequencing a nucleic acid library in the presence of a high ionic strength solution. In some embodiments, the disclosure relates generally to a modified polymerase that retains polymerase activity in the presence of a high ionic strength solution. In some embodiments, the high ionic strength solution can be at least 120 mM salt. In some embodiments, the high ionic strength solution can be from 125 mM to 200 mM salt. In some embodiments, the salt can include a potassium and/or sodium salt. In some embodiments, the salt can include NaCl and/or KCl. In some embodiments, the high ionic strength solution can further include a sulfate. In some embodiments, a modified polymerase is capable of amplifying (and/or sequencing) a nucleic acid molecule in the presence of a high ionic strength solution to a greater capacity (for example as measured by accuracy) than a reference polymerase lacking one or more of the corresponding amino acid mutations under identical conditions. In some embodiments, a modified polymerase is capable of amplifying (and/or sequencing) a nucleic acid molecule in the presence of a high ionic strength solution to a greater capacity (for example as measured by thermostability) than a reference polymerase lacking one or more of the amino acid mutations under identical conditions. In some embodiments, a modified polymerase is capable of amplifying (and/or sequencing) a nucleic acid molecule in the presence of a high ionic strength solution to a greater capacity (for example as measured by processivity) than a reference polymerase lacking one or more of the amino acid mutations under identical conditions.

Optionally, the method further includes repeating the addition of one or more dNTPs under polymerizing conditions to incorporate a plurality of dNTPs into the nucleic acid template to generate the nucleic acid library.

In some embodiments, the method can further include detecting a nucleotide incorporation by-product during the polymerization. In some embodiments, the nucleotide incorporation by-product can include a hydrogen and/or phosphate ion.

In some embodiments, the method further includes determining the identity of the incorporated dNTPs in the nucleic acid library. In some embodiments, the method further includes determining the number of incorporated nucleotides in the nucleic acid library. In some embodiments, the detecting can further include sequencing the nucleic acid library.

In some embodiments, the disclosed modified polymerase compositions, (as well as related methods, systems, apparatuses and kits) can be used to detect nucleotide incorporation through the generation of by-product formation during the nucleotide incorporation event. Many methods of detecting nucleotide incorporation by-products are known in the art, and it will be readily appreciated that all such methods are within the scope of the present disclosure. Suitable methods of nucleotide by-product detection include without limitation, detection of hydrogen ion, inorganic phosphate, inorganic pyrophosphate, and the like. Several of these by-product detection methods typically involve template-dependent nucleotide incorporation.

In some embodiments, the modified polymerase of the present disclosure can be used to perform label-free nucleic acid sequencing, and in particular, ion-based nucleic acid sequencing. The concept of label-free nucleic acid sequencing, including ion-based nucleic acid sequencing, including the following references that are incorporated by reference in their entirey: Rothberg et al, U.S. Patent Publication Nos. 2009/0026082, 2009/0127589, 2010/0301398, 2010/0300895, 2010/0300559, 2010/0197507, and 2010/0137143, which are incorporated by reference herein in their entireties. Briefly, in such nucleic acid sequencing applications, nucleotide incorporations are determined by detecting the presence of natural byproducts of polymerase-catalyzed nucleic acid synthesis reactions, including hydrogen ions, polyphosphates, PPi, and Pi (e.g., in the presence of pyrophosphatase).

In a typical embodiment of ion-based nucleic acid sequencing, nucleotide incorporations are detected by detecting the presence and/or concentration of hydrogen ions generated by polymerase-catalyzed nucleic acid synthesis reactions, including for example primer extension reactions. In one embodiment, templates that are operably bound to a primer and a polymerase and that are situated within reaction chambers (such as the microwells disclosed in Rothberg et al, cited above), are subjected to repeated cycles of polymerase-catalyzed nucleotide addition to the primer ("adding step") followed by washing ("washing step"). In some embodiments, such templates may be attached as clonal populations to a solid support, such as a microparticle, nucleic acid sequencing bead, or the like, and said clonal populations are loaded into reaction chambers. As used herein, "operably bound" means that a primer is annealed to a template so that the primer can be extended by a polymerase and that a polymerase is bound to such primer-template duplex, or in close proximity thereof so that primer extension takes place whenever sufficient nucleotides are supplied.

In each adding step of the cycle, the polymerase extends the primer by incorporating added nucleotide in a template-dependent fashion, such that the nucleotide is incorporated only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. In some embodiments, the production of hydrogen ions is proportional to (e.g., monotonically related) to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, is proportional to the number of contiguous identical complementary bases. If the next base in the template is not complementary to the added nucleotide, then no incorporation occurs and no hydrogen ion is released.

In some embodiments, after each step of adding a nucleotide, a washing step is performed, in which an unbuffered wash solution at a predetermined pH is used to remove the nucleotide of the previous step in order to prevent miscorporations in later cycles (incomplete extension). In some embodiments, after each step of adding a nucleotide, an additional step may be performed wherein the reaction chambers are treated with a nucleotide-destroying agent, such as apyrase, to eliminate any residual nucleotides remaining in the chamber, thereby minimizing the probability of spurious extensions in subsequent cycles. In some embodiments, the treatment may be included as part of the washing step itself.

In one exemplary embodiment, different kinds (or "types") of nucleotides are added sequentially to the reaction chambers, so that each reaction is exposed to the different nucleotide types one at a time. For example, nucleotide types can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired. In some embodiments, the time taken to apply each nucleotide sequentially to the reaction chamber (i.e. flow cycle) can be varied depending on the sequencing information desired. For example, the flow cycle can in some instances be reduced when sequencing long nucleic acid molecules to reduce the overall time needed to sequence the entire nucleic acid molecule. In some embodiments, the flow cycle can be increased, for example when sequencing short nucleic acids or amplicons. In some embodiments, the flow cycle can be about 0.5 seconds to about 3 seconds. In some embodiments, the flow cycle can be about 1 second to about 1.5 seconds.

In one embodiment, the disclosure relates generally to a method of detecting a nucleotide incorporation, including: performing a nucleotide incorporation using a modified polymerase and generating one or more byproducts of the nucleotide incorporation; and detecting the presence of at least one of the one or more byproducts of the nucleotide incorporation, thereby detecting the nucleotide incorporation.

In some embodiments, the method can further include repeating the performing and detecting steps at least once. In some embodiments, the modified polymerase exhibits increased read length and/or processivity relative to a reference polymerase under otherwise similar or identical reaction conditions.

In some embodiments, detecting the presence of the sequencing byproduct includes contacting the reaction mixture with a sensor capable of sensing the presence of the sequencing byproduct. The sensor can include a field effect transistor, for example a chemFET or an ISFET. In some embodiments, sequencing byproducts of nucleotide incorporation can include a hydrogen ion, a dye-linked moiety, a polyphosphate, a pyrophosphate or a phosphate moiety, and detecting the presence of the sequencing byproduct includes using an ISFET to detect the sequencing byproduct. In some embodiments, the detecting step includes detecting a hydrogen ion using the ISFET.

In some embodiments, the modified polymerase includes a polymerase linked to a bridging moiety. The bridging moiety is optionally linked to the polymerase through one or more attachment sites within the modified polymerase. In some embodiments, the bridging moiety is linked to the polymerase through a linking moiety. The linking moiety can be linked to at least one of the one or more attachment sites of the polymerase. In some embodiments, the polymerase of the modified polymerase includes a single attachment site, and the bridging moiety is linked to the polymerase through the single attachment site, either directly or through a linking moiety. In some embodiments, the single attachment site can be linked to a biotin moiety, and the bridging moiety can include an avidin moiety. In some embodiments, the bridging moiety is linked to the polymerase through at least one biotin-avidin bond. In some embodiments, the modified polymerase exhibits increased read length and/or processivity and/or read accuracy, increased total throughput, reduced strand bias, lowered systematic error relative to a reference polymerase under otherwise similar or identical reaction conditions.

In some embodiments, the disclosure relates generally to a method of detecting a change in ion concentration during a nucleotide polymerization reaction, including: performing a nucleotide polymerization reaction using a modified polymerase including a polymerase linked to a bridging moiety, wherein the concentration of at least one type of ion changes during the course of the nucleotide polymerization reaction; and detecting a signal indicating the change in concentration of the at least one type of ion.

In some embodiments, the disclosure relates generally to a method of detecting a change in ion concentration during a nucleotide polymerization reaction, including: performing a nucleotide polymerization reaction using a modified polymerase including a polymerase linked to a bridging moiety, wherein the concentration of at least one type of ion changes during the course of the nucleotide polymerization reaction; and detecting a signal indicating the change in concentration of the at least one type of ion.

In some embodiments, the method can further include repeating the performing and detecting steps at least once. In some embodiments, detecting the change in concentration of the at least one type of ion includes using a sensor capable of sensing the presence of the byproduct. The sensor can include a field effect transistor, for example a chemFET or an ISFET. In some embodiments, the at least type of ion includes a hydrogen ion, a polyphosphate, a pyrophosphate or a phosphate moiety, and detecting the change in concentration of the at least one type of ion includes using an ISFET to detect the at least one type of ion. In some embodiments, the at least one type of ion includes a hydrogen ion, and detecting the presence of the at least one type of ion includes detecting the hydrogen ion using an ISFET.

In some embodiments, the disclosure relates generally to methods (and related kits, systems, apparatuses and compositions) for performing a nucleotide polymerization reaction comprising or consisting of contacting a modified polymerase or a biologically active fragment thereof with a nucleic acid template in the presence of one or more nucleotides, where the modified polymerase or the biologically active fragment thereof includes one or more amino acid modifications relative to a reference polymerase, and where the modified polymerase or the biologically active fragment thereof has improved accuracy, coverage and/or processivity as compared to the reference polymerase, and polymerizing at least one of the one or more nucleotides using the modified polymerase or the biologically active fragment thereof.

In some embodiments, the disclosure relates generally to methods (and related kits, systems, apparatuses and compositions) for performing a nucleotide polymerization reaction comprising or consisting of contacting a modified polymerase or a biologically active fragment thereof with a nucleic acid template in the presence of one or more nucleotides, where the modified polymerase or the biologically active fragment thereof includes one or more amino acid modifications relative to a reference polymerase, and where the modified polymerase or the biologically active fragment thereof has an increased thermostability relative to the reference polymerase, and polymerizing at least one of the one or more nucleotides using the modified polymerase or the biologically active fragment thereof. In some embodiments, the method includes polymerizing at least one of the one or more nucleotides using the modified polymerase or the biologically active fragment thereof in the presence of a high ionic strength solution. In some embodiments, a high ionic strength solution can include a solution in excess of 100 mM KCl. In some embodiments, a high ionic strength solution includes a solution that is at least 120 mM KCl. In some embodiments, a high ionic strength solution includes a solution that is 125 mM to 200 mM KCl.

In some embodiments, the method can further include polymerizing one of the at least one nucleotides in a template-dependent fashion. In some embodiments, the polymerizing is performed under thermocycling conditions. In some embodiments, the method can further include hybridizing a primer to the nucleic acid template prior to, during, or after the contacting, and where the polymerizing includes polymerizing one of the at least one nucleotides onto an end of the primer using the modified polymerase or the biologically active fragment thereof. In some embodiments, the polymerizing is performed in the proximity of a sensor that is capable of detecting the polymerization of the at least one nucleotide by the modified polymerase or the biologically active fragment thereof. In some embodiments, the method can further include detecting a signal indicating the polymerization of the at least one nucleotide by the modified polymerase or the biologically active fragment thereof using a sensor. In some embodiments, the sensor is an ISFET. In some embodiments, the sensor can include a detectable label or detectable reagent within the polymerizing reaction.

In some embodiments, the disclosure generally relates to methods (and related kits, apparatus, systems and compositions) for performing nucleic acid amplification comprising or consisting of generating an amplification reaction mixture having a modified polymerase typically having 70, 75, 80, 85, 90, 95, 96, 97, 98, or 99% sequence identity to SEQ ID NO:1 or SEQ ID NO:34, or a biologically active fragment thereof, a primer, a nucleic acid template, and one or more nucleotides, where the modified polymerase or the biologically active fragment thereof includes one or more amino acid modifications relative to a reference polymerase and has improved thermostability relative to the reference polymerase; and subjecting the amplification reaction mixture to amplifying conditions, where at least one of the one or more nucleotides is polymerized onto the end of the primer using the modified polymerase or the biologically active fragment thereof. In some embodiments, the modified polymerase or the biologically active fragment thereof having improved thermostability relative to the reference polymerase (e.g., SEQ ID NO: 1 or SEQ ID NO: 34), comprises or consists of at least 80% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure generally relates to methods (and related kits, apparatus, systems and compositions) for performing nucleic acid amplification comprising or consisting of generating an amplification reaction mixture having a modified polymerase, typically having 70, 75, 80, 85, 90, 95, 96, 97, 98, or 99% sequence identity to SEQ ID NO:1 or SEQ ID NO:34, or a biologically active fragment thereof, a primer, a nucleic acid template, and one or more nucleotides, where the modified polymerase or the biologically active fragment thereof includes one or more amino acid modifications relative to a reference polymerase and has improved accuracy relative to the reference polymerase; and subjecting the amplification reaction mixture to amplifying conditions, where at least one of the one or more nucleotides is polymerized onto the end of the primer using the modified polymerase or the biologically active fragment thereof. In some embodiments, the modified polymerase or the biologically active fragment having improved accuracy relative to the reference polymerase (e.g., SEQ ID NO: 1 or SEQ ID NO: 34) comprises or consists of at least 80% identity SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In illustrative embodiments, the method is an emulsion PCR method. As such, it will be understood that the amplification reaction mixture is added to an emulsion oil composition before exposing the nucleic acid template to amplifying conditions. The addition can take place over a period of seconds rather than all at once, and can occur while the emulsion oil composition is being agitated.

The solution that includes the emulsion oil and the amplification reaction mixture can then be agitated for example, for 30 seconds to 30 minutes, 1 minute to 20 minutes, 2 minutes to 10 minutes, or for example, for 5 minutes before being exposed to amplification conditions. The amplification can occur after dispensing the reaction mixture after the agitation into PCR compatible places, which can then be loaded onto a thermocycler. In certain embodiments, the emulsion PCR is performed in a reaction mixture that includes 120 to 200 mM salt, such as 120 mM to 150 mM KCl.

In some embodiments, the method further includes determining the identity of the one or more nucleotides polymerized by the modified polymerase. In some embodiments, the method further includes determining the number of nucleotides polymerized by the modified polymerase. In some embodiments, at least 50% of the one or more nucleotides polymerized by the modified polymerase are identified. In some embodiments, substantially all of the one or more nucleotides polymerized by the modified polymerase are identified. In some embodiments, the polymerization occurs in the presence of a high ionic strength solution. In some embodiments the high ionic strength solution comprises 125 mM to 200 mM salt. In some embodiments, the polymerization occurs in the presence of an ionic strength solution of at least 120 mM salt. In some embodiments, the high ionic strength solution comprises KCl and/or NaCl.

In some embodiments, the disclosure generally relates to methods (and related kits, systems, apparatuses and compositions) for performing a nucleotide polymerization reaction comprising or consisting of mixing a modified polymerase or a biologically active fragment thereof with a nucleic acid template in the presence of one or more nucleotides, where the modified polymerase or the biologically active fragment thereof includes one or more amino acid modifications relative to a reference polymerase (such as SEQ ID NO: 1 or SEQ ID NO: 34; and polymerizing at least one of the one or more nucleotides using the modified polymerase or the biologically active fragment thereof in the mixture. In some embodiments, the modified polymerase or the biologically active fragment thereof has increased accuracy as determined by measuring increased accuracy in the presence of a high ionic strength solution. In some embodiments, the high ionic strength solution refers to a reaction mixture for performing nucleotide polymerization having at least 120 mM KCl. In some embodiments, a high ionic strength solution includes a solution that is 125 mM to 200 mM KCl.

In some embodiments, the methods (and related kits, apparatus, systems and compositions) comprise a modified polymerase or a biologically active fragment thereof comprising or consisting of at least 80% identity to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure generally relates to methods (and related kits, systems, apparatus and compositions) for detecting nucleotide incorporation comprising or consisting of performing a nucleotide incorporation reaction using a modified polymerase or a biologically active fragment thereof having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33, a nucleic acid template, and one or more nucleotide triphosphates; generating the nucleotide incorporation; and detecting the nucleotide incorporation. Detecting nucleotide incorporation can occur via any appropriate means such as PAGE, fluorescence, dPCR quantitation, nucleotide by-product production (e.g., hydrogen ion or pyrophosphate detection; suitable nucleotide by-product detection systems include without limitation, next-generation (i.e. massively parallel, high throughput) sequencing platforms such as Rain Dance, Roche 454, and Ion Torrent Systems)) or nucleotide extension product detection (e.g., optical detection of extension products or detection of labelled nucleotide extension products). In some embodiments, the methods (and related kits, systems, apparatus and compositions) for detecting nucleotide incorporation include or consist of detecting nucleotide incorporation using a modified polymerase or a biologically active fragment thereof that includes at least 95% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the method of detecting nucleotide incorporation includes or consists of detecting nucleotide incorporation using a modified polymerase or a biologically active fragment thereof that includes at least 98% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the method of detecting nucleotide incorporation includes or consists of detecting nucleotide incorporation by a modified polymerase or a biologically active fragment thereof that includes at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the method further comprises determining the identity of one or more nucleotides in the nucleotide incorporation. In some embodiments, the byproduct of the nucleotide incorporation is a hydrogen ion. In some embodiments, the byproduct of the nucleotide incorporation is a pyrophosphate. In some embodiments, the byproduct of the nucleotide incorporation is a labeled nucleotide extension product. In some embodiments, the method of detecting nucleotide incorporation includes generating the nucleotide incorporation under emulsion PCR or bridge PCR conditions.

In some embodiments, the disclosure generally relates to methods (and related kits, systems, apparatus and compositions) for detecting a change in ion concentration during a nucleotide polymerization reaction comprising or consisting of performing a first nucleotide polymerization reaction on a nucleic acid template or nucleic acid library in the presence of one of more nucleotides to be incorporated during the first nucleotide polymerization reaction, wherein the first nucleotide polymerization reaction includes a modified polymerase or a biologically active fragment thereof having at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; and performing a second nucleotide polymerization reaction, wherein the second nucleotide polymerization reaction detects at least one type of ion concentration change during the course of the second nucleotide polymerization reaction and provides a signal indicating a change in ion concentration of the at least one type of ion. In some embodiments, the ion is a hydrogen ion. In some embodiments, the ion is a pyrophosphate ion. In some embodiments, the signal indicating a change in ion concentration is a relative increase in the production of hydrogen ions in the polymerization reaction. In some embodiments, detection of at least one type of ion concentration change is monitored using an ISFET. In some embodiments, the modified polymerase or the biologically active fragment from the first nucleotide polymerization reaction comprises or consists of at least 150 contiguous amino acid residues of a polymerase having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the modified polymerase or the biological active fragment from the first nucleotide polymerization reaction comprises or consists of at least 200 contiguous amino acid resides of the polymerase having at least 95% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the modified polymerase or the biological active fragment from the first nucleotide polymerization reaction comprises or consists of at least 250 contiguous amino acid resides of the polymerase having at least 98% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In some embodiments, the modified polymerase or the biological active fragment from the first nucleotide polymerization reaction comprises or consists of a polymerase having at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

In some embodiments, the disclosure generally relates to methods (and related kits, systems, apparatus and compositions) for amplifying a nucleic acid comprising or consisting of contacting a nucleic acid with a polymerase or a biologically active fragment thereof comprising at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 under suitable conditions for amplification of the nucleic acid; and amplifying the nucleic acid. In some embodiments, the amplifying is performed using a polymerase chain reaction, emulsion polymerase chain reaction, isothermal amplification reaction, recombinase polymerase amplification reaction, proximity ligation amplification, rolling circle amplification or strand displacement amplification. In some embodiments, the amplifying includes clonally amplifying the nucleic acid in solution. In some embodiments, the amplifying includes clonally amplifying the nucleic acid on a solid support such as a nucleic acid bead, flow cell, nucleic acid array, or wells present on the surface of the solid support. In some embodiments, the amplifying is performed using a polymerase or biologically active fragment comprising a thermostable DNA polymerase. In some embodiments, the polymerase or biologically active fragment comprises a DNA polymerase having improved thermostability as compared to a reference polymerase, such as SEQ ID NO: 1 or SEQ ID NO: 34. In some embodiments, the polymerase or biologically active fragment comprises a DNA polymerase having improved accuracy as compared to a reference polymerase, such as SEQ ID NO: 1 or SEQ ID NO: 34.

In some embodiments, the methods (and related kits, systems, apparatus and compositions) for amplifying a nucleic acid comprising contacting a nucleic acid with a polymerase or a biologically active fragment thereof comprising at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 under suitable conditions for amplification of the nucleic acid; and amplifying the nucleic acid. In some embodiments, the polymerase or biologically active fragment comprises a DNA polymerase having an improved average read length as compared to the average read length obtained using a DNA polymerase encoded by SEQ ID NO: 1 or SEQ ID NO: 34 under identical amplification conditions.

In some embodiments, the methods for amplifying a nucleic acid comprise contacting a nucleic acid with a polymerase or a biologically active fragment thereof comprising at least 95% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 under suitable conditions for amplification of the nucleic acid; and amplifying the nucleic acid. In some embodiments, the method includes a polymerase or biologically active fragment having an improved average read length as compared to the average read length obtained using a DNA polymerase encoded by SEQ ID NO: 1 or SEQ ID NO: 34 under identical amplification conditions.

In some embodiments, the methods for amplifying a nucleic acid comprise contacting a nucleic acid with a polymerase or a biologically active fragment thereof comprising at least 98% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 under suitable conditions for amplification of the nucleic acid; and amplifying the nucleic acid. In some embodiments, the method includes a polymerase or biologically active fragment having an improved average read length as compared to the average read length obtained using a DNA polymerase encoded by SEQ ID NO: 1 or SEQ ID NO: 34 under identical amplification conditions.

In some embodiments, the methods for amplifying a nucleic acid comprise contacting a nucleic acid with a polymerase or a biologically active fragment thereof comprising at least 99% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33 under suitable conditions for amplification of the nucleic acid; and amplifying the nucleic acid. In some embodiments, the method includes a polymerase or biologically active fragment having an improved average read length as compared to the average read length obtained using a DNA polymerase encoded by SEQ ID NO: 1 or SEQ ID NO: 34 under identical amplification conditions.

In some embodiments, average read length is determined by analyzing the read length of the amplified nucleic acids obtained using one or more of the modified polymerase provided herein, across all reads to establish an average read length and comparing the average read length to the average read length obtained using the reference polymerase.

In some embodiments, the disclosure generally relates to methods for amplifying a nucleic acid comprising or consisting of contacting a nucleic acid with a polymerase or a biologically active fragment thereof comprising at least 80% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33, under suitable conditions for amplification of the nucleic acid; and amplifying the nucleic acid. In some embodiments, the amplifying is performed by a polymerase or biologically active fragment having improved templating efficiency as compared to a reference sample, such as SEQ ID NO: 1 or SEQ ID NO: 34. In some embodiments the method for amplifying a nucleic acid comprises amplifying the nucleic acid under emulsion PCR conditions. In some embodiments the method for amplifying a nucleic acid comprises amplifying the nucleic acid under bridge PCR conditions. In some embodiments, the bridge PCR conditions include hybridizing one or more of the amplified nucleic acids to a solid support. In some embodiments, the hybridized one or more amplified nucleic acids can be used as a template for further amplification. In some embodiments, the modified polymerase or biologically active fragment thereof comprises a polymerase that is derived from *Thermus aquaticus* DNA polymerase (Taq). SEQ ID NO: 1 is the full-length, wild-type, nucleic acid sequence of the DNA polymerase, *Thermus aquaticus* (Taq). In some embodiments, Taq DNA polymerase can be used as a reference polymerase in the methods, kits, apparatus, systems and compositions described herein.

In some embodiments, the disclosure generally relates to methods (and related kits, systems, apparatus and compositions) for synthesizing a nucleic acid comprising or consisting of incorporating at least one nucleotide onto the end of a primer using a modified polymerase or a biologically active fragment thereof having at least 90% identity to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. Optionally, the method further comprises detecting incorporation of the at least one nucleotide onto the end of the primer. In some embodiments, the method further includes determining the identity of at least one of the at least one nucleotide incorporated onto the end of the primer. In some embodiments, the method can include determining the identity of all nucleotides incorporated onto the end of the primer. In some embodiments, the method includes synthesizing the nucleic acid in a template-dependent manner. In some embodiments, the method can include synthesizing the nucleic acid in solution, on a solid support, or in an emulsion (such as emPCR).

In some embodiments, provided herein are kits that include at least two vessels, such as tubes, each containing one or more reaction mixture or reaction mixture component as provided herein, such as a nucleotide tri-phosphate and/or a buffer that is effective for nucleic acid polymerization, amplification, and/or sequencing reactions. At least one of the vessels includes a modified polymerase or biologically active fragment thereof, of the invention and one or more other tubes can include nucleotides and/or a buffer appropriate for one of the methods provided herein, for example. In some embodiments, the kits can be virtual kits wherein a number of separate reagents are listed, marketed and/or sold together, such as on a web page or a smart phone application that lists different reagents that can be purchased together.

In some embodiments, a kit useful for performing a nucleic acid polymerization reaction includes a buffer, at least one type of nucleotide triphosphate, and a modified polymerase or biologically active fragment thereof, of the invention.

In some embodiments, a kit useful for performing a nucleic acid polymerization reaction includes a buffer, at least one type of nucleotide triphosphate, optionally a salt such as sodium chloride or potassium chloride, and optionally $MgCl_2$, and a second tube comprising a modified polymerase of the invention, or biologically active fragment thereof. The tube comprising the polymerase, can include stabilizers and other components such as glycerol and a detergent such as, for example, Tween-20 or NP-40. In some illustrative embodiments, the kit can include a third vessel that contains a solid support, such as beads, that optionally contain primers for performing a method provided herein. In certain embodiment, the kit can further include a tube that includes oil useful for forming emulsions for emulsion PCR and optionally emulsion stabilizers. For example, and not intended to be limiting, such tube can include a biocompatible mineral oil, Allox 4912, and Span 80, In some embodiments, one tube of the kit includes a buffer composition that includes any one or more of the following: a monovalent metal salt, a divalent metal salt, a divalent anion, and a detergent. For example, the buffer composition can include a potassium or sodium salt. For example, the buffer composition can include a potassium or sodium salt. For example, the buffer composon can include 50 to 200 mM salt, 50 to 100 mM salt, 120 to 200 mM salt, such as 120 to 150 mM KC. In some embodiments, the buffer composition can include a manganese or magnesium salt. In some embodiments, the buffer composition can include a sulfate such as potassium sulfate and/or magnesium sulfate. In some embodiments, the buffer composition can include a detergent. In some embodiments, the buffer compositions can include a detergent such as Triton and/or Tween.

In some embodiments, the kit includes a tube with a buffer composition that includes at least one potassium salt, at least one manganese salt, and Triton X-100 (Pierce Biochemicals). The salt can optionally include a chloride salt or a sulfate salt. In some embodiments, the buffer composition can include a pH of about 7.3 to about 8.0. In some embodiments, the buffer composition can include a pH of about 7.4 to about 7.9. In some embodiments, the buffer composition includes a potassium salt at concentrations of between 5-250 mM, 50-225 mM, 125-200 mM (depending on the divalent).

In some embodiments, the buffer composition included in a tube of a kit includes magnesium or manganese salt at a concentration of between 1 mM and 20 mM. In some embodiments, the buffer composition includes magnesium or manganese salt at a concentration of between 6-15 mM. In some embodiments, the buffer composition includes a sulfate at a concentration of between 1 mM and 100 mM. In some embodiments, the buffer composition includes a sulfate at a concentration of between 5-50 mM. In some embodiments, the buffer composition of the kit includes a detergent (e.g., Triton X-100 or Tween-20) at a concentration of between 0.001% to 1%. In some embodiments, the buffer composition includes a detergent (e.g., Triton X-100 or Tween-20) at a concentration of between 0.0025-0.0125%.

In some embodiments, the kit further includes a nucleic acid capture bead. These kits can include a tube with an emulsion oil such as mineral oil.

The following non-limiting examples are provided purely by way of illustration of exemplary embodiments, and in no way limit the scope and spirit of the present disclosure. Furthermore, it is to be understood that any inventions disclosed or claimed herein encompass all variations, combinations, and permutations of any one or more features described herein. Any one or more features may be explicitly excluded from the claims even if the specific exclusion is not set forth explicitly herein. It should also be understood that disclosure of a reagent for use in a method is intended to be synonymous with (and provide support for) that method involving the use of that reagent, according either to the specific methods disclosed herein, or other methods known in the art unless one of ordinary skill in the art would understand otherwise. In addition, where the specification and/or claims disclose a method, any one or more of the reagents disclosed herein may be used in the method, unless one of ordinary skill in the art would understand otherwise.

EXAMPLES

Example 1: Production & Purification of Exemplary Modified Polymerases

Amino acid mutations were introduced via site-directed mutagenesis into an exemplary reference polymerase having the amino acid sequence of SEQ ID NO: 1. In this example, wild-type full length Taq DNA Polymerase (832 amino acids in length) was used as the reference polymerase from which exemplary mutations were introduced via site-directed saturation mutagenesis.

Here, 831 amino acid residues of SEQ ID NO: 1 after methionine (at amino acid position 1 of SEQ ID NO: 1) were substituted with every possible amino acid, at each amino acid residue along the polymerase. Recombinant expression constructs encoding these modified polymerases were transformed into bacteria. Colonies containing expression constructs were inoculated into BRM media, grown to OD=0.600 and induced by adding IPTG to a final concentration of 1 mM. The cells were then grown for a further 3 hours at 37° C.

The induced cells were centrifuged for 10 minutes at 6000 rpm, supernatant was discarded, and the cells were resuspended in resuspension buffer (10 mM Tris, pH 7.5, 100 mM NaCl). The resuspended cells were sonicated at a setting of 60 (amplitude) for one minute, and then placed on ice for 1 minute. The sonication was repeated in this manner for a total of 5 times. The samples were incubated at 65° C. for 10 minutes. The samples were centrifuged at 9000 rpm for 30 minutes. The supernatant was recovered and further purified over a Heparin column.

Purified polymerases were assessed for expression and/or polymerase activity as compared to SEQ ID NO: 1. The number of amino acid residues substituted along the entire length of the WT Taq DNA polymerase was 831. The average number of amino acid variants observed at each amino acid residue along the polymerase was 17.8 variants per amino acid residue. The total number of polymerase clones (each consisting of a single amino acid substitution as compared to SEQ ID NO: 1) achieved using this method was 14,833. The total number of clones possessing characteristics that were substantially superior to characteristics observed for polymerase performance using SEQ ID NO: 1 under standard emulsion PCR conditions was 332 clones. These superior characteristics or properties included thermostability and/or polymerase activity in 125 mM KCl or NaCL and/or at least one of the following characteristics or properties associated with a sequencing reaction when the mutant polymerases were used in a template emulsion PCR amplification step of the nucleic acids analyzed in the sequencing reaction: read length, accuracy, strand bias, systematic error, and total sequencing throughput. The number of clones that were assessed for secondary characterization was 31 clones, where each clone consisted of a single amino acid substitution as compared to SEQ ID NO: 1. As provided herein, exemplary modified polymerases SEQ ID NO: 5 through SEQ ID NO: 33 are modified polymerases consisting of a single amino acid substitution as compared to SEQ ID NO: 1.

Example 2: Production & Purification of Exemplary Double, Triple, and Quadruple Modified Polymerases Double, triple, and quadruple amino acid substitutions were introduced via site-directed mutagenesis into an exemplary reference polymerase having amino acid sequence of SEQ ID NO: 1. In this example, wild-type full length Taq DNA Polymerase (SEQ ID NO: 1) was used as the reference polymerase from which exemplary double, triple, and quadruple amino acid mutations were introduced.

Here, modified polymerases were prepared according to Example 1. Several of the 31 clones assessed for secondary characterization were used as the basis to combine multiple single amino acid substitutions into the reference polymerase according to the method set forth in Example 1.

Briefly, clones of interest from Example 1 were assessed as possessing superior polymerase performance as compared to WT Taq DNA polymerase under identical emPCR conditions. The selected individual amino acid substitutions were then introduced into the reference polymerase (SEQ ID NO: 1) via site-directed mutagenesis to create a plurality of different double, triple, and quadruple amino acid substitution polymerases. Recombinant expression constructs encoding these modified polymerases were transformed into bacteria. Colonies containing expression constructs were inoculated into BRM media, grown to OD=0.600 and induced by adding IPTG to a final concentration of 1 mM. The cells were then grown for a further 3 hours at 37° C.

The induced cells were centrifuged for 10 minutes at 6000 rpm, supernatant was discarded, and the cells were resuspended in resuspension buffer (10 mM Tris, pH 7.5, 100 mM NaCl). The resuspended cells were sonicated at a setting of 60 (amplitude) for one minute, and then placed on ice for 1 minute. The sonication was repeated in this manner for a total of 5 times. The samples were incubated at 65° C. for 10 minutes. The samples were centrifuged at 9000 rpm for 30 minutes. The supernatant was recovered and further purified over a Heparin column.

Purified double, triple, and quadruple polymerases were assessed for expression and/or polymerase activity as compared to SEQ ID NO: 1. As provided herein, SEQ ID NO: 3 and SEQ ID NO: 4 represent exemplary double and triple amino acid substitution polymerases, respectively, possessing superior PCR performance under emulsion PCR conditions as compared to WT Taq DNA Polymerase (SEQ ID NO:1). These superior characteristics or properties included thermostability and/or polymerase activity in 125 mM KCl or NaCL and/or at least one of the following characteristics or properties associated with a sequencing reaction when the mutant polymerases were used in a template emulsion PCR amplification step of the nucleic acids analyzed in the sequencing reaction: read length, accuracy, strand bias, systematic error, and total sequencing throughput. It is believed that these improvements, at least in part, were the result of increased processivity.

SEQ ID NO: 3 consists of a double amino acid substitution polymerase (L763F+E805I) wherein the numbering is relative to WT Taq DNA polymerase (SEQ ID NO: 1).

SEQ ID NO: 4 consists of a triple amino acid substitution polymerase (E397V+E745T+L763F) wherein the numbering is relative to WT Taq DNA polymerase (SEQ ID NO: 1).

Example 3: Comparing Performance of Modified and Reference Polymerases in Emulsion PCR A modified isolated polymerase comprising a mutant Taq DNA polymerase (SEQ ID NO: 2) including an amino acid substitution E397V (wherein the numbering is relative to the amino acid sequence of SEQ ID NO: 1) was purified essentially as described in Example 1. Both the modified polymerase (SEQ ID NO: 2) and a reference polymerase (SEQ ID NO: 1)(control reaction) were then evaluated for performance in emulsion based PCR reactions under identical conditions.

The library of nucleic acid molecules to be amplified under the emulsion PCR conditions included amplicons that were known to be particularly difficult to amplify under standard emPCR conditions. The library of nucleic acid molecules included 55 amplicons that included high or extreme GC content (>60% GC); 42 amplicons having high or extreme AT content (>60% AT); 299 amplicons that included homopolymer (HP) regions of differing lengths (e.g., 2 HP-9 HP); 95 amplicons which prematurely attenuated under standard emPCR conditions; 20 amplicons of 320 bp insert length; and 20 amplicons of 420 bp insert length.

Briefly, the library of nucleic acid molecules was adapter-ligated and size selected as described in User Guide for the Ion Fragment Library Kit (Ion Torrent Systems, Part No. 4466464; Publication Part No. 4467320 Rev B). The library of nucleic acid molecules were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) (incorporated by reference herein in its entirety) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463), except that the on-test or reference polymerase was used in place of the polymerase provided in the kit. The amplified nucleic acid molecules were then loaded into a PGM™ 314 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923). Ion Torrent Systems is a subsidiary of Life Technologies Corp., Carlsbad, Calif.).

The resulting sequencing data using the reference or modified polymerase was analyzed to measure AQ20 mean read length (MRL), strand bias, base coverage, accuracy, sequencing throughput (Mb) and uniformity of coverage.

Using the standard software supplied with the PGM™ sequencing system, the sequencing reaction data using the reference or modified polymerases for emPCR were measured and compared. The exemplary modified polymerase including the amino acid substitution E397V (SEQ ID NO: 2) provided significantly increased AQ20 MRL reads, reduced strand bias, increased base coverage, increased accuracy, increased sequencing throughput (Mb) and increased uniformity of coverage relative to the reference polymerase (SEQ ID NO: 1)(data not shown).

The amino acid sequence corresponding to the modified polymerase provided in this example is SEQ ID NO: 2. It will be readily apparent to one of ordinary skill in the art, that any one or more of the modified polymerases disclosed, or suggested, by the disclosure can be readily converted (e.g., reverse translated) to the corresponding nucleic acid sequence encoding the modified polymerase. It will also be apparent to the skilled artisan that the nucleic acid sequence for each polypeptide is variable due to the degenerate nature of codons. For example, there are six codons that code for leucine (CTT, CTC, CTA, CTG, TTA and TTG). Thus, the base at position 1 of this codon can be a C or T, position 2 of this codon is always a T, and the base at position 3 can be T, C, A or G. Accordingly, any modified polymerase disclosed or suggested by the disclosure can be translated to any one or more of the degenerate codon nucleic acid sequences.

Example 4: Evaluating Modified Polymerase Performance in High Ionic Strength Emulsion PCR A variety of modified polymerases consisting of single amino acid substitutions were prepared according to Example 1. The modified DNA polymerases were then evaluated for performance in emulsion PCR to generate nucleic acid libraries essentially according to Example 3. The library of nucleic acid molecules to be amplified under emulsion PCR conditions included amplicons that were known to be particularly difficult to amplify under standard emPCR conditions (see Example 3).

In this example, a salt titration experiment was performed to determine the functionality of the modified polymerases at high ionic strength conditions. The salt titration included evaluation at 75 mM salt, 100 mM salt and high ionic strength solution (125 mM salt). In this example, the high ionic strength condition included 125 mM KCl.

Briefly, the library of nucleic acid molecules was adapter-ligated and size selected as described in User Guide for the Ion Fragment Library Kit (Ion Torrent Systems, Part No. 4466464; Publication Part No. 4467320 Rev B). The library of nucleic acid molecules were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463), except that the on-test or reference polymerase was used in place of the polymerase provided in the kit.

The amplified nucleic acid molecules were then loaded into a PGM™ 314 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923). Ion Torrent Systems is a subsidiary of Life Technologies Corp., Carlsbad, Calif.).

FIGS. 1A-1E depict exemplary results of several modified polymerases consisting of a single amino acid substitution prepared according to Example 1 and evaluated under emPCR conditions at various salt concentrations. The first bar (reading from left to right) at each salt concentration represents the sequencing throughput obtained for each modified polymerase. The second bar (reading from left to right) at each salt concentration represents the mean read length (MRL) obtained for each modified polymerase. The last bar (reading from left to right) at each salt concentration represents the key signal (which is a control to demonstrate if emPCR occurred). Generally, the level of sequencing throughput for each of the five modified polymerases presented, increased in reaction conditions that included 125 mM KCl compared to 75 mM KCl during the emPCR reaction.

Example 5: Evaluating a Double Amino Acid Substitution Mutant Polymerase for Performance in Emulsion PCR A modified polymerase prepared according to Example 2 comprising a double amino acid substitution of Taq DNA polymerase (E397V+E745T, where the numbering is relative to the amino acid residues of SEQ ID NO: 1) was compared to a Taq DNA polymerase having a single amino acid substitution (SEQ ID NO: 34) for performance in emulsion PCR (emPCR) reactions that generate nucleic acid libraries.

The nucleic acid libraries were produced from *Rhodopseudomonas palustris* (which is 5,459,213 base-pair circular chromosome having a GC content of 65.05% (see Larimer et al., *Nature Biotechnology*, 2004, Volume 22, Number 1, pg 55-61) and evaluated under high ionic strength conditions (125 mM salt; here, 125 mM KCl).

The libraries obtained using the modified polymerases from the emPCR step were applied downstream in an ion-based sequencing reaction using the Ion Torrent PGM™ sequencing system (Ion Torrent Systems, Part No. 4462917).

Briefly, the library *Rhodopseudomonas palustris* was adapter-ligated and size selected (here, the insert was a 420 bp insert) as described in User Guide for the Ion Fragment Library Kit (Ion Torrent Systems, Part No. 4466464; Publication Part No. 4467320 Rev B). The library of nucleic acid molecules were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463), except that the on-test or reference polymerase was used in place of the polymerase provided in the kit.

The amplified library was then loaded into a PGM™ 314 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923). Ion Torrent Systems is a subsidiary of Life Technologies Corp., Carlsbad, Calif.).

The resulting sequencing data obtained using the modified polymerases during high ionic strength emPCR was analyzed to measure the number of AQ20 bases, accuracy, and the average perfect read length of the 420 bp insert. The data for the exemplary sequencing run performed as outlined in this example is shown in FIGS. 2A1-2B2. As can be seen, the sequencing data from 125 mM KCl emPCR conditions obtained from a double amino acid substitution polymerase (E397V+E745T) possessed improved AQ20 reads (386 bp v. 359 bp), improved read accuracy (99.8% v. 99.6%), and improved perfect read length (331 bp v. 290 bp) as compared to a single amino acid substitution polymerase (SEQ ID NO: 34). Both modified DNA polymerases were capable of generating significant sequencing data, as a result of having created substantial numbers of nucleic acid libraries during the emPCR process under high ionic strength conditions. However, the double amino acid substitution polymerase outperformed the single amino acid polymerase substitution (SEQ ID NO: 34) under identical conditions.

Example 6: Amino Acid Substitution Taq Polymerase Mutants for Performance in Emulsion PCR A variety of modified polymerases prepared according to Example 1 consisting of different single amino acid substitutions was compared to a Taq DNA polymerase mutant also consisting of a single amino acid substitution (SEQ ID NO: 34) for performance in emulsion PCR reactions that generate nucleic acid libraries. The nucleic acid libraries were produced from *Rhodopseudomonas palustris* and were evaluated under various ionic strength conditions (e.g., 75 mm to 150 mM KCl).

The libraries obtained using the modified polymerases from the emPCR were applied downstream in an ion-based sequencing reaction using the Ion Torrent PGM™ sequencing system (Ion Torrent Systems, Part No. 4462917).

Briefly, the library *Rhodopseudomonas palustris* was adapter-ligated and size selected (here, the insert was a 420 bp insert) as described in User Guide for the Ion Fragment Library Kit (Ion Torrent Systems, Part No. 4466464; Publication Part No. 4467320 Rev B). The library of nucleic acid molecules were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463), except that the on-test or reference polymerase was used in place of the polymerase provided in the kit.

The amplified library was then loaded into a PGM™ 314 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923). Ion Torrent Systems is a subsidiary of Life Technologies Corp., Carlsbad, Calif.).

The resulting exemplary sequencing data obtained using the modified polymerases during emPCR was analyzed to measure the number of AQ20 total base count, AQ17 mean, AQ20 mean, uniformity of coverage, strand bias, total base coverage, systematic sequencing error (SSE) among other criteria. The data for the sequencing runs performed as outlined in this example is shown in FIGS. 3A-3B. As can be seen, the sequencing data obtained from several of the single amino acid substitution polymerases possessed improved AQ20 total base count, improved AQ20 reads, reduced strand bias and reduced SSE as compared to the single amino acid substitution polymerase (SEQ ID NO: 34). For example, the single amino acid substitution polymerases (E397V, E794C or R593G) each outperformed the single amino acid polymerase substitution (SEQ ID NO: 34) under identical conditions.

Example 7: Evaluating Mutant Polymerases with Respect to Thermostability (GC Coverage)

A modified polymerase comprising a single amino acid substitution (E397V) of Taq DNA polymerase having the amino acid sequence of SEQ ID NO: 2 was compared to a different single amino acid substitution of Taq DNA polymerase (SEQ ID NO: 34) for performance in emulsion PCR reactions that generate nucleic acid libraries. The nucleic acid libraries were produced from *Rhodopseudomonas palustris* which contains a GC content of over 65%. The ability of each mutant polymerase to function during emPCR under high ionic strength solution was evaluated (e.g., 125 mM KCl).

The libraries obtained using the modified Taq DNA polymerases from the emPCR step were applied downstream in an ion-based sequencing reaction using the Ion Torrent PGM™ sequencing system (Ion Torrent Systems, Part No. 4462917).

Briefly, the library *Rhodopseudomonas palustris* was adapter-ligated and size selected (here, the insert was a 420 bp insert) as described in User Guide for the Ion Fragment Library Kit (Ion Torrent Systems, Part No. 4466464; Publication Part No. 4467320 Rev B). The library of nucleic acid molecules were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463), except that the on-test or reference polymerase was used in place of the polymerase provided in the kit.

The amplified library was then loaded into a PGM™ 314 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923). Ion Torrent Systems is a subsidiary of Life Technologies Corp., Carlsbad, Calif.).

The resulting exemplary sequencing data obtained using the modified Taq DNA polymerases as outlined in this example is shown in FIG. 4. In FIG. 4, "Taqlr1" refers to SEQ ID NO: 34 (D732R); while reference to "Hit #1" refers to amino acid substitution "E397V" (SEQ ID NO: 2). Taqlr1 or Taq-LR1 polymerase was engineered to have higher template affinity than Wild type Taq polymerase. This increased template affinity has allowed for templating of longer libraries, presumably caused by improved fidelity and processivity. As is evident from the data, the single amino acid substitution polymerase "E397V" outperforms with respect to read length, sequencing throughput, and uniformity of coverage as compared to Taq-LR1 (SEQ ID NO: 34) under identical emPCR conditions.

Additionally, the nucleic acid library amplified during emPCR was a library from a species of bacteria having at least 65% GC content. It is well known in the art that nucleic acid amplification of nucleic acid molecules having high GC content is usually difficult compared to non-GC rich targets (McDowell et al., *Nucleic Acids Research*, 1998; 26: 3340-3347). It is also well known in the art, that GC content is predictive of melting temperature. Thus, a high GC content genome will possess a higher melting temperature than a lower GC content genome. Here, the "E397V" modified polymerase offered substantially greater amplification of a high GC content nucleic acid library as compared to SEQ ID NO: 34. Based on the overall sequencing data in this example, it was determined that the modified polymerase (SEQ ID NO: 2) resulted in less than 5 gaps of genomic coverage per gigabyte of sequencing data; while SEQ ID NO: 34 offered at least 99 gaps of genomic coverage per gigabyte of sequencing data.

The ability to accurately and faithfully sequence the content of GC rich organisms and GC rich regions is useful in a variety of fields, including bacterial studies, where several genuses of bacteria possess greater than 65% GC content (e.g., some species of *Streptomyces* and *Mycobacterium*). A polymerase that generates 99 or more gaps of genomic coverage per gigabyte of sequencing data is less useful for DNA sequencing, detection methods, and the like, than a polymerase that produces a genomic map having fewer than 20, 10, or 5 gaps of genomic coverage per gigabyte of sequencing data. In order for a user to complete the genome using the former polymerase, a user would need to perform additional amplifications of the genome using "finishing reactions" which comprise designing and purchasing a pair of primers for each gap per gigabyte of sequencing data. Once successfully designed, the 99 or more primer pair reactions per gigabyte of sequencing data must undergo sufficient amplification to span the gaps present across the entire genome. However, using the latter polymerase (e.g., SEQ ID NO: 2), a user could establish most of the genome of *Rhodopseudomonas palustris* in a single emPCR reaction. Only if necessary, would the user need to prepare 5 primer pairs per gigabyte of sequencing data to complete the genome.

Not to be limited by theory, a modified polymerase having improved GC content coverage as defined herein can also correspond to a modified polymerase having improved thermostability (see Example 10). During emPCR, the nucleic acid library must be denatured in order for the amplification step to proceed. If the GC content of the nucleic acid library is high, it is likely that the nucleic acid library will be less likely to denature, or that any primers present will correctly anneal to the template strand, and as a result, it is less likely that the modified polymerase can initiate polymerization of the primers. Modified polymerase "E397V" was found to possess higher thermostability at 96° C. as compared to SEQ ID NO: 1 (see Example 10). Modified polymerase "E397V" also demonstrated higher coverage uniformity and longer read length at 97° C. as compared to the same reaction at 96° C. (see FIG. 4.) Accordingly, modified polymerase "E397V" possesses greater thermostability as compared to SEQ ID NO: 1 under identical emPCR conditions.

Example 8: Evaluating Double Amino Acid Substitution Mutants for Polymerase Performance in Emulsion PCR In this example, four polymerases each having a double amino acid substitution (E397V+E745T; P6N+E295F; P6N+E397V; or E745T+E794C) were prepared according to Example 2 and compared to a Taq DNA polymerase having a single amino acid substitution (SEQ ID NO: 34) for performance in emPCR reactions under high ionic strength conditions.

The nucleic acid libraries were prepared using an *E. coli* 500 bp insert. The nucleic acid libraries obtained from the emPCR reactions were applied downstream in an ion-based sequencing reaction using the Ion Torrent PGM™ sequencing system (Ion Torrent Systems, Part No. 4462917).

Briefly, the template DNA was purified, adapter-ligated and size selected as described in User Guide for the Ion Fragment Library Kit (Ion Torrent Systems, Part No. 4466464; Publication Part No. 4467320 Rev B). The library of nucleic acid molecules were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463), except that the on-test or reference polymerase was used in place of the polymerase provided in the kit.

The amplified library was then loaded into a PGM™ 318 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923). Ion Torrent Systems is a subsidiary of Life Technologies Corp., Carlsbad, Calif.).

Figure 5B:
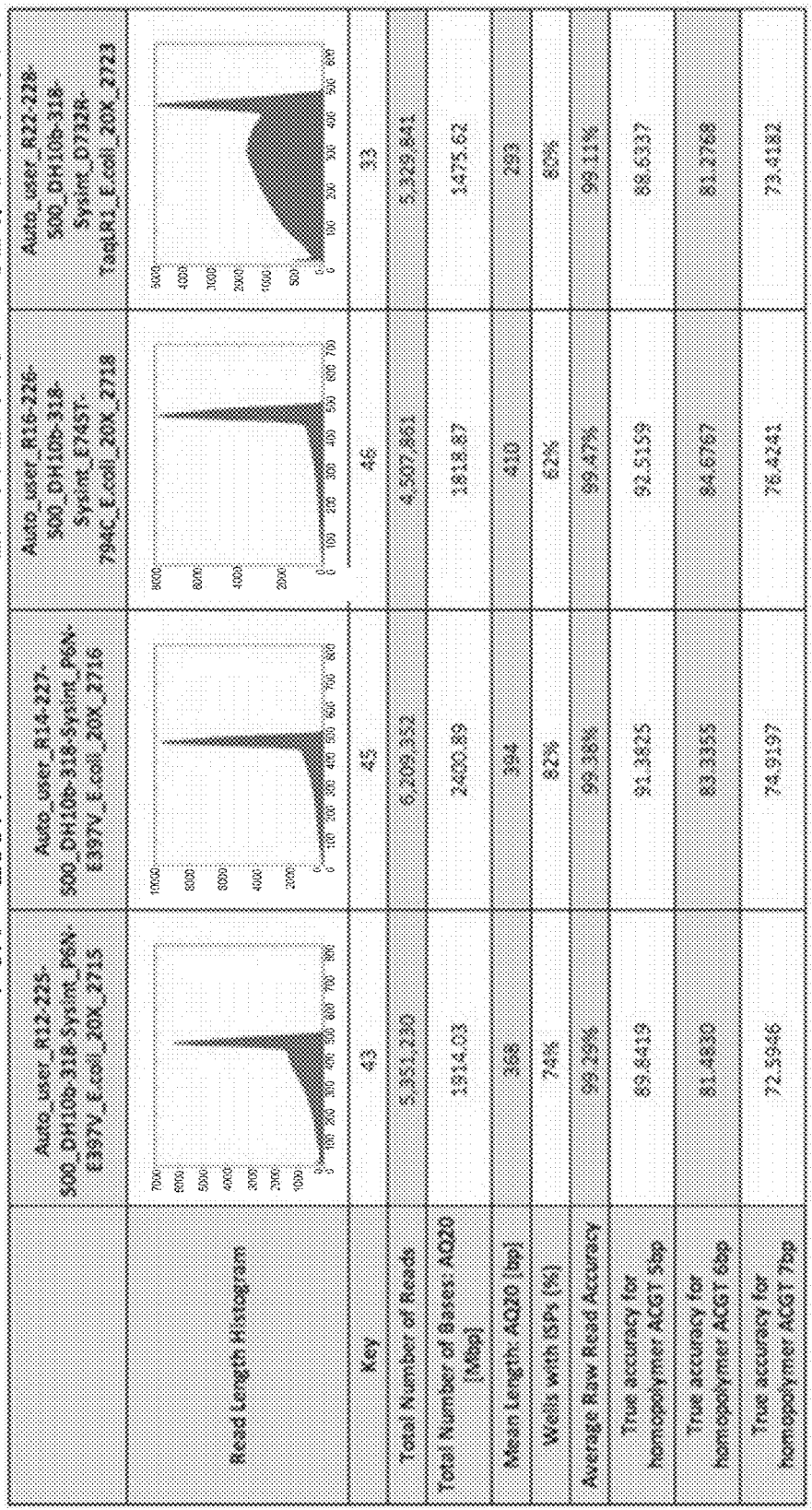
Figure 7:
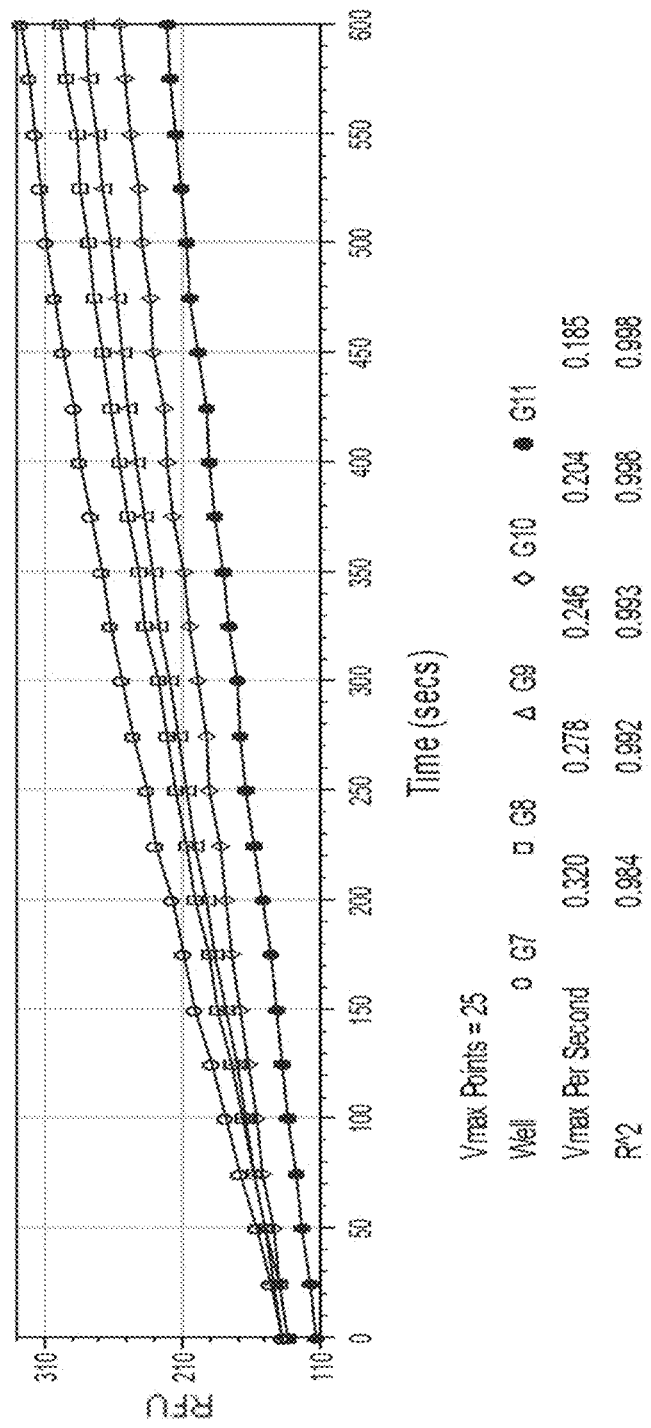
FIG. 7 shows a graph providing exemplary thermostability data obtained using an exemplary modified polymerase according to the disclosure.
Figure 8:
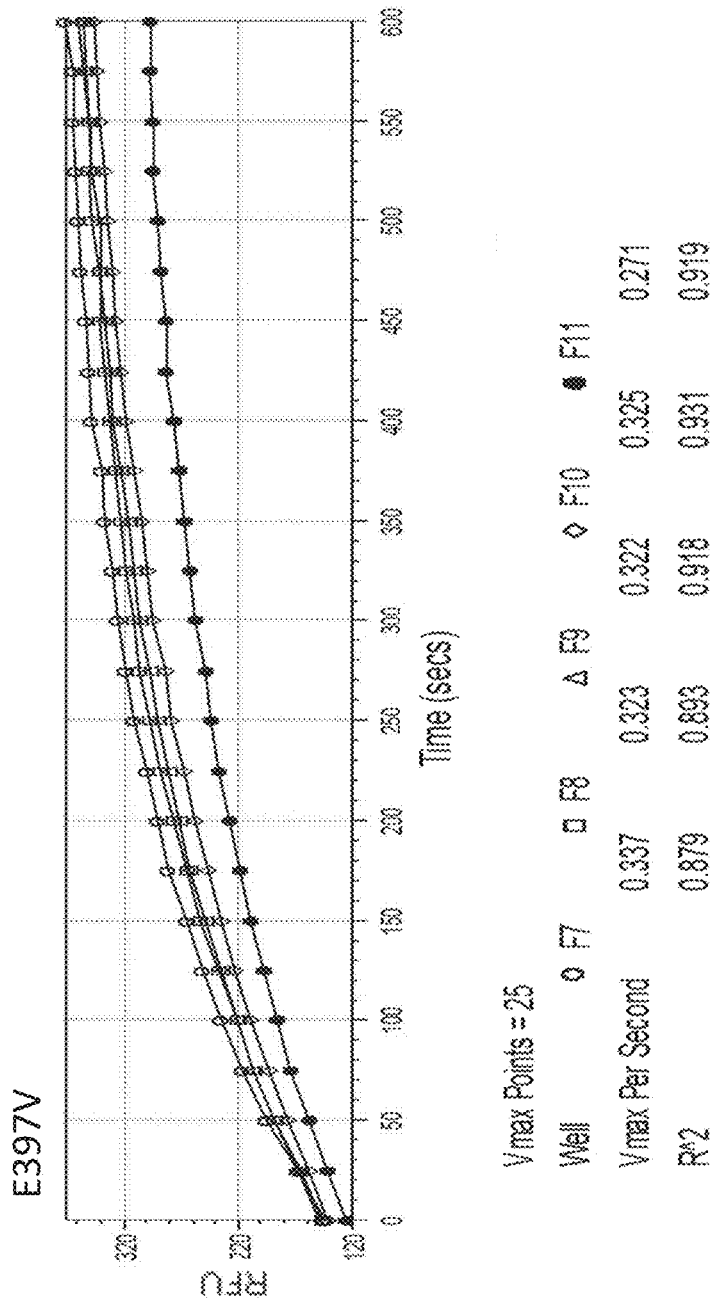
FIG. 8 shows a graph providing exemplary thermostability data obtained using an exemplary modified polymerase according to the disclosure.
Figure 9:
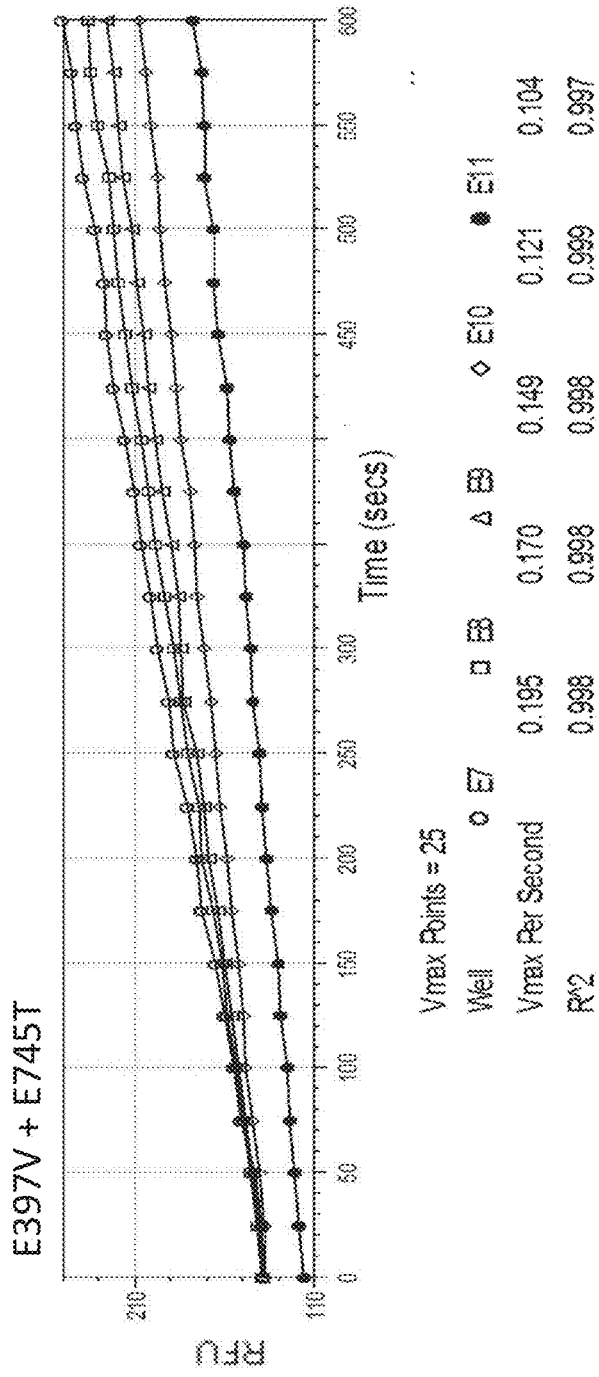
FIG. 9 shows a graph providing exemplary thermostability data obtained using an exemplary modified polymerase according to the disclosure.
Figure 10:
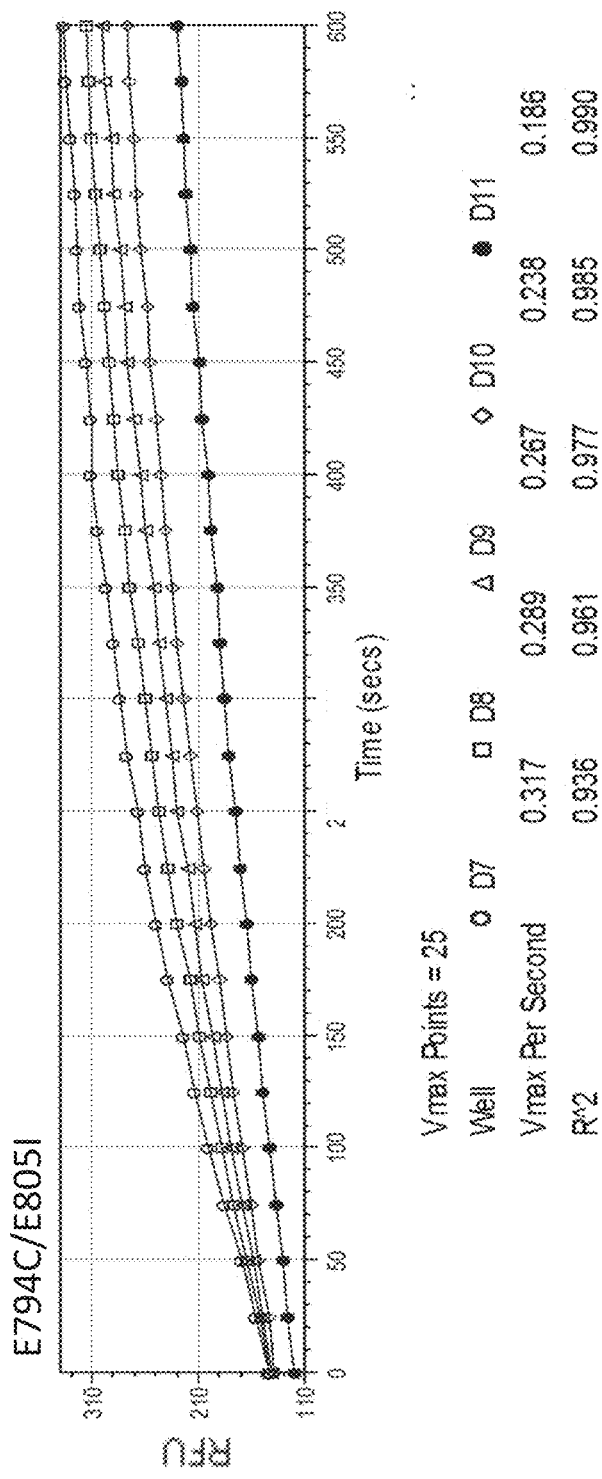
FIG. 10 shows a graph providing exemplary thermostability data obtained using an exemplary modified polymerase according to the disclosure.

The resulting sequencing data obtained using the modified polymerases under high ionic strength emPCR (125 mM KCl) was analyzed to measure the number of AQ20 bases, raw read accuracy, and true accuracy for homopolymers (HP) of 5 bp, 6 bp, or 7 bp in length. The data for the exemplary sequencing runs performed as outlined in this example is shown in FIGS. 5A-5B. As can be seen, the sequencing data from all four polymerase consisting of a double amino acid substitution outperformed the single amino acid substitution polymerase (SEQ ID NO: 34) in all observed metrics.

Example 9: Evaluating Double & Triple Amino Acid Substitution Polymerase Mutants for Performance in Emulsion PCR In this example, three polymerases, each having one or more amino acid substitutions were prepared according to Example 1 or Example 2 and compared to a Taq DNA polymerase having a single amino acid substitution (SEQ ID NO: 34) for performance in emPCR reactions under high ionic strength conditions (e.g., 125 mM KCl).

The nucleic acid libraries were prepared using an *E. coli* 500 bp insert. The nucleic acid libraries obtained from the emPCR reactions were applied downstream in an ion-based sequencing reaction using the Ion Torrent PGM™ sequencing system (Ion Torrent Systems, Part No. 4462917).

Briefly, the template DNA was purified, adapter-ligated and size selected as described in User Guide for the Ion Fragment Library Kit (Ion Torrent Systems, Part No. 4466464; Publication Part No. 4467320 Rev B). The library of nucleic acid molecules were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463), except that the on-test or reference polymerase was used in place of the polymerase provided in the kit.

The amplified library was then loaded into a PGM™ 318 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923). Ion Torrent Systems is a subsidiary of Life Technologies Corp., Carlsbad, Calif.).

The resulting sequencing data obtained using the modified polymerases under high ionic strength emPCR was analyzed to measure the number of AQ20 bases, raw accuracy, systematic sequencing error (SSE) and total sequencing throughput (AQ20 bases) among other metrics. The data for the exemplary sequencing runs performed as outlined in this example is shown in FIG. 6. As can be seen, the sequencing data from the mutant polymerase "E397V" outperformed the single amino acid substitution polymerase (SEQ ID NO: 34) based on all observed metrics. The "E397V" modified polymerase also outperformed both the double and triple amino acid substitution polymerases under identical emPCR conditions.

Example 10: Comparing Thermostability Performance of Modified and Reference Polymerases In this example, various modified polymerases containing one or more amino acid substitutions were prepared according to Example 1 or Example 2. Modified polymerase "E397V" consisting of a single amino acid substitution at amino acid residue 397 relative to the numbering of amino acid residues of SEQ ID NO: 1 was prepared according to Example 1. Modified polymerase "SEQ ID NO: 34" consisting of a single amino acid substitution as compared to SEQ ID NO: 1 was prepared according to Example 1.

Modified polymerase "E794C+E805I" consisted of a double amino acid substitution relative to the amino acid numbering of SEQ ID NO: 1 and was prepared according to Example 2. Additionally, modified polymerase "E397V+E745T" consisted of a double amino acid substitution relative to the amino acid numbering of SEQ ID NO: 1 and was prepared according to Example 2.

Figure 14:
FIG. 14 is a schematic outlining an exemplary thermostability activity assay performed according to the disclosure.

The polymerases described above were each prepared for thermostability testing as a PCR strip as follows for thermocycling at 95° C.: 15 mM Tris pH 7.5, 100 mM KCl, 30% Trehalose, 0.1% NP40 (a detergent) and 50 nM of polymerase (see FIG. 14).

The PCR strips were incubated at various time points of heat treatment (no heat control=0 min; 2 mins; 4 mins; 6 mins or 8 mins). After heat treatment at 95° C. or 96° C. was completed, the reaction mixtures were placed on ice. The reaction mixtures were then transferred to plates for polymerase activity assays.

Here, the polymerase activity assay was prepared as follows: 15 mM Tris pH 7.5, 100 mM KCl, 8 mM MgCl$_2$, 150 nm Oligo 221 and 5 nM of polymerase reaction mixture from the heat-treatment step (10 ul) were combined. Oligo 221 is a hairpin oligo with a fluorescent dye attached (TTTTTTTGCAGGTGACAGGTTTTTCCTGT-CACCXGC (SEQ ID NO: 50), where X is a fluorescein-dT residue). Upon addition of dATP, oligo 221 is extended, resulting in release of the florescence (See Nikiforov, *Analytical Biochemistry*, (2011) 229-236, incorporated herein by reference in its entirety).

In order to initiate the polymerase activity assay, 20 uM of dATP was added to each reaction. Changes in fluorescence for each heat-treated polymerase at each time point (0, 2, 4, 6 and 8 mins) were measured and plotted (see FIGS. 7-10). Here, the fluorescence signal at 525 nm was measured over a period of time using an excitation wavelength of 490 nm.

The thermostability of a variety of additional single or double amino acid substitution polymerases prepared according to Example 1 or Example 2 was also assessed as outlined in this example.

Figure 11:
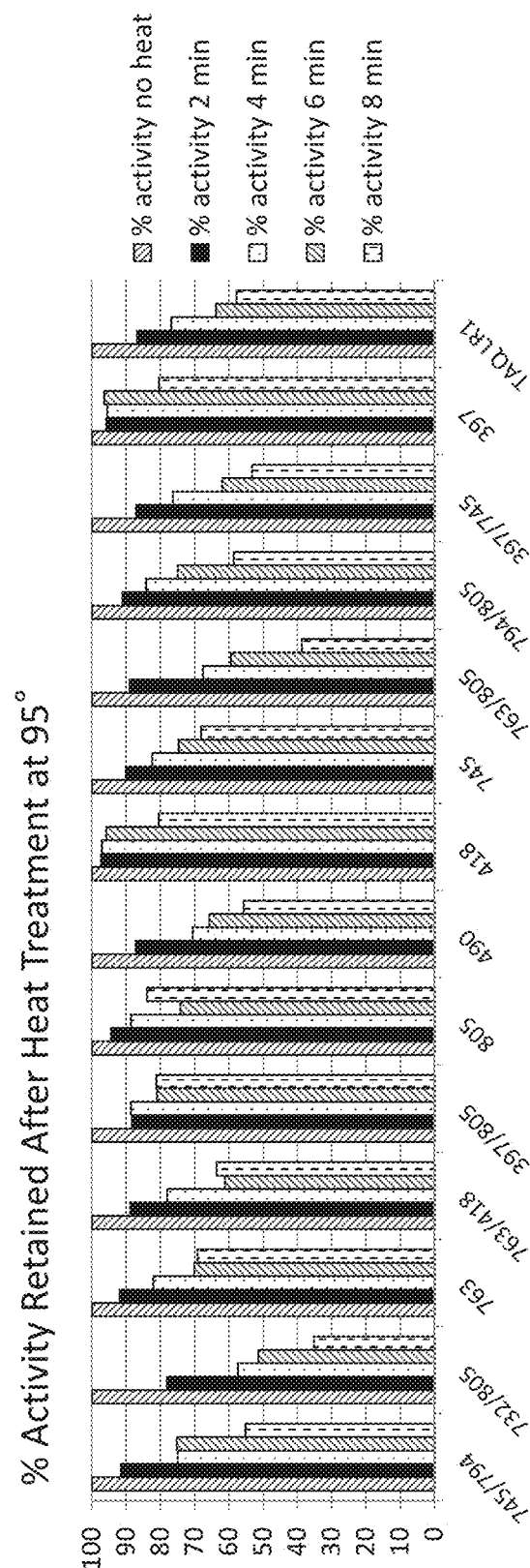
FIG. 11 shows a graph providing exemplary thermostability data at 95° C. obtained using exemplary modified polymerases according to the disclosure.

FIG. 11 provides exemplary thermostability data obtained for a plurality of single or double amino acid mutant polymerases compared to SEQ ID NO: 34 (TAQ LR1) at 95° C. in the presence of Trehalose. Mutant polymerase "E397V" and mutant polymerase "G418C" demonstrated greatest thermostability at 95° C. under the test conditions. It should be noted that the amino acid residue numbers in FIGS. 11-14 represent the residue that is mutated in the following manner: P6N, A77E, A97V, L193V, K240I, R266Q, E267T, L287T, P291T, K292C, E295F or E295N, E397V, G418C, L490Q, A502S, S543V, D578E, R593G, L678F or L678T, S699W, E713W, V737A, E745T, L763F, E790G, E794C, E805I and L828A. Two numbers separated by a slash represent a double mutant with the above mutations at the noted residues.

Figure 12:
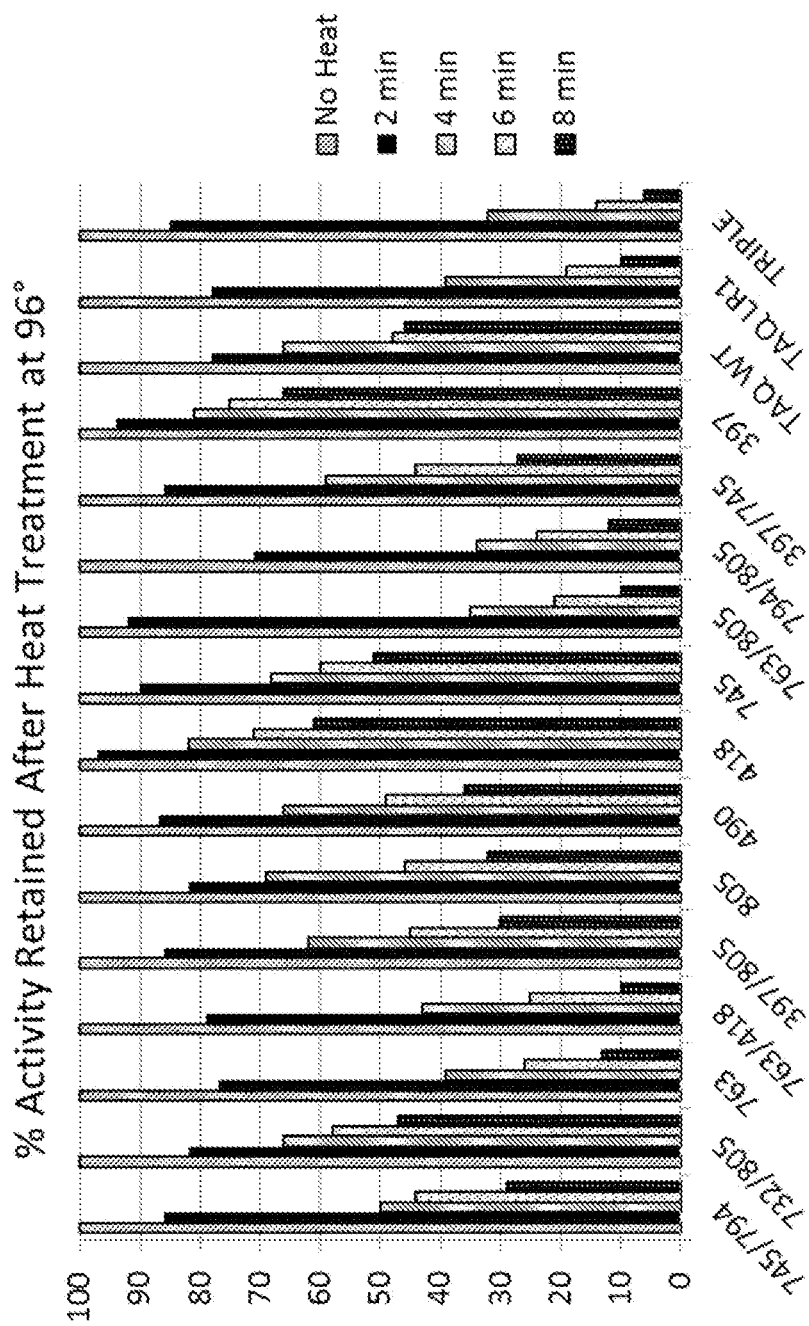
FIG. 12 shows a graph providing exemplary thermostability data obtained at 96° C. using exemplary modified polymerases according to the disclosure.

FIG. 12 provides exemplary thermostability data obtained for the same single or double amino acid mutant polymerases as compared against WT Taq DNA polymerase (SEQ ID NO: 1)(TAQ WT) and SEQ ID NO: 34 (TAQ LR1) at 96° C. in the presence of Trehalose. Mutant polymerase "E397" and mutant polymerase "G418C" demonstrated greatest thermostability at 96° C. under the test conditions.

Figure 13:
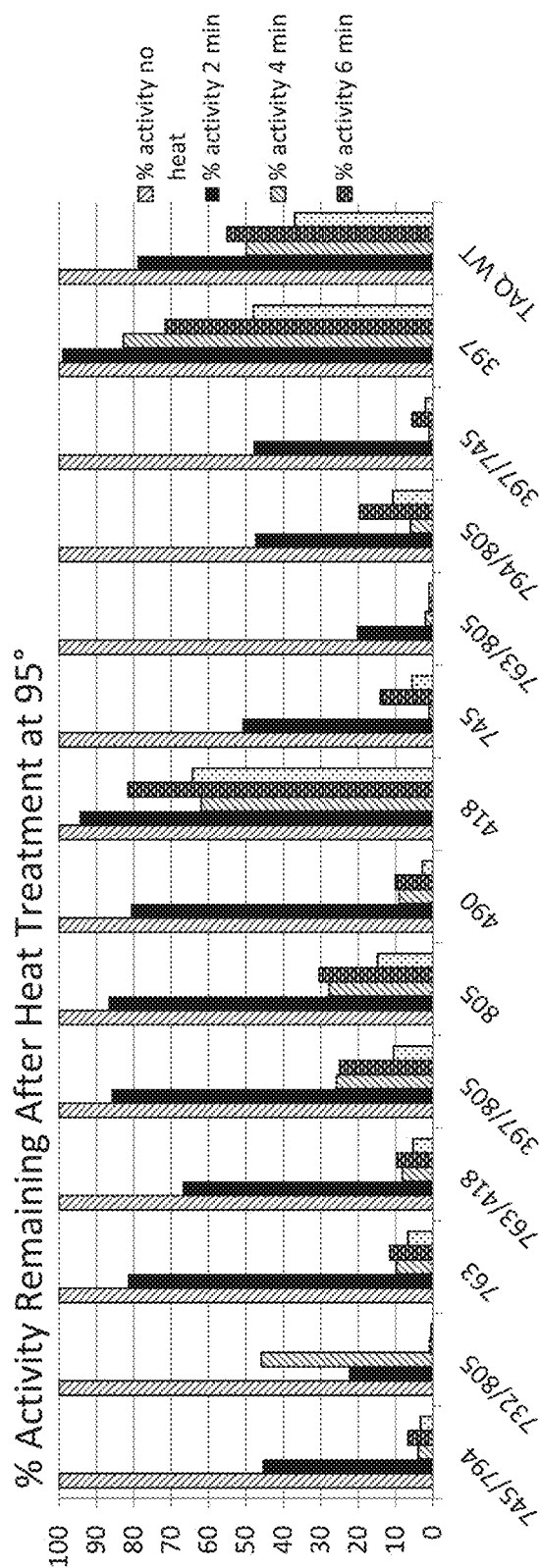
FIG. 13 shows a graph providing exemplary thermostability data obtained at 95° C. in the absence of trehalose using exemplary modified polymerases according to the disclosure.

FIG. 13 provides exemplary thermostability data obtained for the same single or double amino acid mutant polymerases as compared against WT Taq DNA polymerase (TAQ WT) at 95° C. in the absence of Trehalose (during the heat-treatment step). Here, mutant polymerase "E397V" and mutant polymerase "G418C" demonstrated superior thermostability at 95° C. in the absence of trehalose as compared to WT Taq (SEQ ID NO: 1) under the test conditions.

It will be apparent to one of ordinary skill in the art that the foregoing thermostability assay is provided as an exemplary thermostability assay and is not meant as limiting or restricting in any manner. As such, other variations to the thermostability assay provided herein, or other forms of thermostability assays or other means by which to assess residual polymerase activity are contemplated within the scope of the present invention.

What is claimed is:

1. A composition comprising a modified polypeptide consisting of the amino acid sequence of SEQ ID NO: 1 having one or more amino acid substitutions selected from the group consisting of L763F, L763F+E805I, or L763F+E397V+E745T, wherein the modified polypeptide exhibits polymerase activity and exhibits an improvement in one or more properties selected from thermostability and/or a sequencing property selected from read length, accuracy, strand bias, systematic error, and total sequencing throughput when the modified polypeptide is used in an emulsion PCR template amplification step of a sequencing workflow, relative to a reference polymerase of SEQ ID NO:1 and/or SEQ ID NO:34.

2. The composition according to claim 1, wherein the modified polypeptide has improved thermostability at 95° C. for 6 minutes as compared to the thermostability of SEQ ID NO: 1 at 95° C. for 6 minutes.

3. The composition according to claim 2, wherein the modified polypeptide includes L763F+E805I.

4. The composition of claim 2, wherein the modified polypeptide includes L763F+E397V+E745T.

5. A reaction mixture comprising the composition of claim 1, a primer, a nucleic acid template, and one or more nucleotides.

6. The reaction mixture of claim 5, wherein the reaction mixture further comprises a solid support.

7. A method for amplifying a nucleic acid, comprising contacting the nucleic acid with the composition according to claim 1 under suitable conditions for amplifying the nucleic acid, and amplifying the nucleic acid.

8. The method according to claim 7, wherein the modified polypeptide has improved thermostability at 95° C. for 6 minutes as compared to the thermostability of SEQ ID NO: 1 at 95° C. for 6 minutes.

9. The method according to claim 8, wherein the modified polypeptide includes L763F+E805I.

10. The method of claim 8, wherein the modified polypeptide includes L763F+E397V+E745T.

11. The method of claim 7, wherein the suitable conditions comprise suitable conditions for performing a polymerase chain reaction.

12. The method of claim 7, wherein the suitable conditions comprise suitable conditions for performing an emulsion polymerase chain reaction.

13. The method of claim 7, wherein the amplifying is clonally amplifying the nucleic acid in solution or on a solid support.

14. The method of claim 7, further comprising determining the nucleic acid sequence of at least a portion of the nucleic acid.

15. A composition comprising a modified polypeptide consisting of the amino acid sequence of SEQ ID NO: 1 having amino acid substitutions consisting of L763F+E805I, wherein the modified polypeptide exhibits polymerase activity and exhibits an improvement in one or more properties selected from thermostability and/or a sequencing property selected from read length, accuracy, strand bias, systematic error, and total sequencing throughput when the modified polypeptide is used in an emulsion PCR template amplification step of a sequencing workflow, relative to a reference polymerase of SEQ ID NO:1 and/or SEQ ID NO:34.

16. A composition comprising a modified polypeptide consisting of the amino acid sequence of SEQ ID NO: 1 having amino acid substitutions L763F+E397V+E745T, wherein the modified polypeptide exhibits polymerase activity and exhibits an improvement in one or more properties selected from thermostability and/or a sequencing property selected from read length, accuracy, strand bias, systematic error, and total sequencing throughput when the modified polypeptide is used in an emulsion PCR template amplification step of a sequencing workflow, relative to a reference polymerase of SEQ ID NO:1 and/or SEQ ID NO:34.

\* \* \* \* \*

SEQUENCE LISTING

```
<160> NUMBER OF SEQ ID NOS: 44

<210> SEQ ID NO 1
<211> LENGTH: 832
<212> TYPE: PRT
<213> ORGANISM: Thermus aquaticus
<220> FEATURE:
<221> NAME/KEY: misc_feature
<223> OTHER INFORMATION: Wild Type Taq Polymerase

<400> SEQUENCE: 1
```

-continued

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
        130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415
```

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

```
<210> SEQ ID NO 2
<211> LENGTH: 832
<212> TYPE: PRT
<213> ORGANISM: Artificial Sequence
<220> FEATURE:
<223> OTHER INFORMATION: Synthetic:  Taq mutant E397V (Hit #1)

<400> SEQUENCE: 2

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
```

```
                    370                 375                 380
Thr Thr Pro Glu Gly Val Ala Arg Arg Tyr Gly Gly Val Trp Thr Glu
385                 390                 395                 400

Glu Ala Gly Glu Arg Ala Ala Leu Ser Glu Arg Leu Phe Ala Asn Leu
                    405                 410                 415

Trp Gly Arg Leu Glu Gly Glu Arg Leu Leu Trp Leu Tyr Arg Glu
                    420                 425                 430

Val Glu Arg Pro Leu Ser Ala Val Leu Ala His Met Glu Ala Thr Gly
                    435                 440                 445

Val Arg Leu Asp Val Ala Tyr Leu Arg Ala Leu Ser Leu Glu Val Ala
                    450                 455                 460

Glu Glu Ile Ala Arg Leu Gly Ala Glu Val Phe Arg Leu Ala Gly His
465                 470                 475                 480

Pro Phe Asn Leu Asn Ser Arg Asp Gln Leu Glu Arg Val Leu Phe Asp
                    485                 490                 495

Glu Leu Gly Leu Pro Ala Ile Gly Lys Thr Glu Lys Thr Gly Lys Arg
                    500                 505                 510

Ser Thr Ser Ala Ala Val Leu Glu Ala Leu Arg Glu Ala His Pro Ile
                    515                 520                 525

Val Glu Lys Ile Leu Gln Tyr Arg Glu Leu Thr Lys Leu Lys Ser Thr
                    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                    565                 570                 575

Ser Asp Pro Asn Leu Gln Asn Ile Pro Val Arg Thr Pro Leu Gly Gln
                    580                 585                 590

Arg Ile Arg Arg Ala Phe Ile Ala Glu Glu Gly Trp Leu Leu Val Ala
                    595                 600                 605

Leu Asp Tyr Ser Gln Ile Glu Leu Arg Val Leu Ala His Leu Ser Gly
                    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                    645                 650                 655

Leu Met Arg Arg Ala Ala Lys Thr Ile Asn Phe Gly Val Leu Tyr Gly
                    660                 665                 670

Met Ser Ala His Arg Leu Ser Gln Glu Leu Ala Ile Pro Tyr Glu Glu
                    675                 680                 685

Ala Gln Ala Phe Ile Glu Arg Tyr Phe Gln Ser Phe Pro Lys Val Arg
                    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                    725                 730                 735

Val Lys Ser Val Arg Glu Ala Ala Glu Arg Met Ala Phe Asn Met Pro
                    740                 745                 750

Val Gln Gly Thr Ala Ala Asp Leu Met Lys Leu Ala Met Val Lys Leu
                    755                 760                 765

Phe Pro Arg Leu Glu Glu Met Gly Ala Arg Met Leu Leu Gln Val His
                    770                 775                 780

Asp Glu Leu Val Leu Glu Ala Pro Lys Glu Arg Ala Glu Ala Val Ala
785                 790                 795                 800
```

```
Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 3
<211> LENGTH: 832
<212> TYPE: PRT
<213> ORGANISM: Artificial Sequence
<220> FEATURE:
<223> OTHER INFORMATION: Synthetic:  (L763F + E805I)

<400> SEQUENCE: 3

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335
```

```
Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750
```

```
Val Gln Gly Thr Ala Ala Asp Leu Met Lys Phe Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Ile Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 4
<211> LENGTH: 832
<212> TYPE: PRT
<213> ORGANISM: Artificial Sequence
<220> FEATURE:
<223> OTHER INFORMATION: Synthetic: (E397V + E745T + L763F)

<400> SEQUENCE: 4

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285
```

```
Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Val Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
```

```
            705                 710                 715                 720
Glu Thr Leu Phe Gly Arg Arg Tyr Val Pro Asp Leu Glu Ala Arg
                    725                 730                 735

Val Lys Ser Val Arg Glu Ala Ala Thr Arg Met Ala Phe Asn Met Pro
                740                 745                 750

Val Gln Gly Thr Ala Ala Asp Leu Met Lys Phe Ala Met Val Lys Leu
                755                 760                 765

Phe Pro Arg Leu Glu Glu Met Gly Ala Arg Met Leu Leu Gln Val His
                770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 5
<211> LENGTH: 832
<212> TYPE: PRT
<213> ORGANISM: Artificial Sequence
<220> FEATURE:
<223> OTHER INFORMATION: Synthetic: P6N

<400> SEQUENCE: 5

Met Arg Gly Met Leu Asn Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
                35                  40                  45

Lys Ser Leu Leu Lys Ala Leu Lys Glu Asp Gly Asp Ala Val Ile Val
            50                  55                  60

Val Phe Asp Ala Lys Ala Pro Ser Phe Arg His Glu Ala Tyr Gly Gly
65              70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
                115                 120                 125

Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
                195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
```

```
                        245                 250                 255
Asp Phe Ala Lys Arg Glu Pro Asp Arg Glu Arg Leu Arg Ala Phe
                    260                 265                 270

Leu Glu Arg Leu Glu Phe Gly Ser Leu Leu His Glu Phe Gly Leu Leu
                275                 280                 285

Glu Ser Pro Lys Ala Leu Glu Ala Pro Trp Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670
```

```
Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 6
<211> LENGTH: 832
<212> TYPE: PRT
<213> ORGANISM: Artificial Sequence
<220> FEATURE:
<223> OTHER INFORMATION: Synthetic: A77E

<400> SEQUENCE: 6

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Glu Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205
```

```
Glu Glu Trp Gly Ser Leu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620
```

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 7
<211> LENGTH: 832
<212> TYPE: PRT
<213> ORGANISM: Artificial Sequence
<220> FEATURE:
<223> OTHER INFORMATION: Synthetic: A97V

<400> SEQUENCE: 7

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
            85                  90                  95

Val Leu Ile Lys Glu Leu Val Asp Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

```
Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
```

```
                580                 585                 590
Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 8
<211> LENGTH: 832
<212> TYPE: PRT
<213> ORGANISM: Artificial Sequence
<220> FEATURE:
<223> OTHER INFORMATION: Synthetic: L193V

<400> SEQUENCE: 8

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
```

-continued

```
            115                 120                 125
Ala Glu Lys Glu Gly Tyr Glu Val Arg Ile Leu Thr Ala Asp Lys Asp
            130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                    165                 170                 175
Asp Gln Trp Ala Asp Tyr Arg Ala Leu Thr Gly Asp Glu Ser Asp Asn
                180                 185                 190
Val Pro Gly Val Lys Gly Ile Gly Glu Lys Thr Ala Arg Lys Leu Leu
            195                 200                 205
Glu Glu Trp Gly Ser Leu Glu Ala Leu Leu Lys Asn Leu Asp Arg Leu
        210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                    245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
            275                 280                 285
Glu Ser Pro Lys Ala Leu Glu Glu Ala Pro Trp Pro Pro Pro Glu Gly
        290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                    325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
        370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                    405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
        450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                    485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
        530                 535                 540
```

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 9
<211> LENGTH: 832
<212> TYPE: PRT
<213> ORGANISM: Artificial Sequence
<220> FEATURE:
<223> OTHER INFORMATION: Synthetic: K240I

<400> SEQUENCE: 9

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

-continued

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Ile
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

```
Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Thr Gly Arg Leu Ser Ser
                565                 570                 575

Ser Asp Pro Asn Leu Gln Asn Ile Pro Val Arg Thr Pro Leu Gly Gln
        580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
        660                 665                 670

Met Ser Ala His Arg Leu Ser Gln Glu Leu Ala Ile Pro Tyr Glu Glu
    675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
        740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
        820                 825                 830

<210> SEQ ID NO 10
<211> LENGTH: 832
<212> TYPE: PRT
<213> ORGANISM: Artificial Sequence
<220> FEATURE:
<223> OTHER INFORMATION: Synthetic: R266Q

<400> SEQUENCE: 10

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30
```

-continued

```
Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Gln Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
```

```
            450                 455                 460
Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 11
<211> LENGTH: 832
<212> TYPE: PRT
<213> ORGANISM: Artificial Sequence
<220> FEATURE:
<223> OTHER INFORMATION: Synthetic: E267T
```

<400> SEQUENCE: 11

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Thr Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415
```

```
Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
                820                 825                 830
```

<210> SEQ ID NO 12
<211> LENGTH: 832
<212> TYPE: PRT
<213> ORGANISM: Artificial Sequence
<220> FEATURE:
<223> OTHER INFORMATION: Synthetic: L287T

<400> SEQUENCE: 12

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Thr Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365
```

```
Pro Gly Asp Asp Pro Met Leu Leu Ala Tyr Leu Leu Asp Pro Ser Asn
    370             375                 380
Thr Thr Pro Glu Gly Val Ala Arg Arg Tyr Gly Gly Glu Trp Thr Glu
385             390                 395                 400
Glu Ala Gly Glu Arg Ala Ala Leu Ser Glu Arg Leu Phe Ala Asn Leu
                405                 410                 415
Trp Gly Arg Leu Glu Gly Glu Arg Leu Leu Trp Leu Tyr Arg Glu
            420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Gly Trp Leu Leu Val Ala
            595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
            755                 760                 765
Phe Pro Arg Leu Glu Glu Met Gly Ala Arg Met Leu Leu Gln Val His
770                 775                 780
Asp Glu Leu Val Leu Glu Ala Pro Lys Glu Arg Ala Glu Ala Val Ala
```

```
                785                 790                 795                 800
Arg Leu Ala Lys Glu Val Met Glu Gly Val Tyr Pro Leu Ala Val Pro
                    805                 810                 815
Leu Glu Val Glu Val Gly Ile Gly Glu Asp Trp Leu Ser Ala Lys Glu
                    820                 825                 830

<210> SEQ ID NO 13
<211> LENGTH: 832
<212> TYPE: PRT
<213> ORGANISM: Artificial Sequence
<220> FEATURE:
<223> OTHER INFORMATION: Synthetic: P291T

<400> SEQUENCE: 13

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Thr Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
```

```
                       325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
            450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
            530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
            595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
            690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
```

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 14
<211> LENGTH: 832
<212> TYPE: PRT
<213> ORGANISM: Artificial Sequence
<220> FEATURE:
<223> OTHER INFORMATION: Synthetic: K292C

<400> SEQUENCE: 14

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

```
Glu Ser Pro Cys Ala Leu Glu Ala Pro Trp Pro Pro Glu Gly
    290             295             300

Ala Phe Val Gly Phe Val Leu Ser Arg Lys Glu Pro Met Trp Ala Asp
305             310             315             320

Leu Leu Ala Leu Ala Ala Arg Gly Gly Arg Val His Arg Ala Pro
            325             330             335

Glu Pro Tyr Lys Ala Leu Arg Asp Leu Lys Glu Ala Arg Gly Leu Leu
            340             345             350

Ala Lys Asp Leu Ser Val Leu Ala Leu Arg Glu Gly Leu Gly Leu Pro
            355             360             365

Pro Gly Asp Asp Pro Met Leu Leu Ala Tyr Leu Leu Asp Pro Ser Asn
            370             375             380

Thr Thr Pro Glu Gly Val Ala Arg Arg Tyr Gly Gly Glu Trp Thr Glu
385             390             395             400

Glu Ala Gly Glu Arg Ala Ala Leu Ser Glu Arg Leu Phe Ala Asn Leu
                405             410             415

Trp Gly Arg Leu Glu Gly Glu Glu Arg Leu Leu Trp Leu Tyr Arg Glu
            420             425             430

Val Glu Arg Pro Leu Ser Ala Val Leu Ala His Met Glu Ala Thr Gly
            435             440             445

Val Arg Leu Asp Val Ala Tyr Leu Arg Ala Leu Ser Leu Glu Val Ala
450             455             460

Glu Glu Ile Ala Arg Leu Glu Ala Glu Val Phe Arg Leu Ala Gly His
465             470             475             480

Pro Phe Asn Leu Asn Ser Arg Asp Gln Leu Glu Arg Val Leu Phe Asp
            485             490             495

Glu Leu Gly Leu Pro Ala Ile Gly Lys Thr Glu Lys Thr Gly Lys Arg
            500             505             510

Ser Thr Ser Ala Ala Val Leu Glu Ala Leu Arg Glu Ala His Pro Ile
            515             520             525

Val Glu Lys Ile Leu Gln Tyr Arg Glu Leu Thr Lys Leu Lys Ser Thr
530             535             540

Tyr Ile Asp Pro Leu Pro Asp Leu Ile His Pro Arg Thr Gly Arg Leu
545             550             555             560

His Thr Arg Phe Asn Gln Thr Ala Thr Ala Thr Gly Arg Leu Ser Ser
            565             570             575

Ser Asp Pro Asn Leu Gln Asn Ile Pro Val Arg Thr Pro Leu Gly Gln
            580             585             590

Arg Ile Arg Arg Ala Phe Ile Ala Glu Glu Gly Trp Leu Leu Val Ala
            595             600             605

Leu Asp Tyr Ser Gln Ile Glu Leu Arg Val Leu Ala His Leu Ser Gly
            610             615             620

Asp Glu Asn Leu Ile Arg Val Phe Gln Glu Gly Arg Asp Ile His Thr
625             630             635             640

Glu Thr Ala Ser Trp Met Phe Gly Val Pro Arg Glu Ala Val Asp Pro
            645             650             655

Leu Met Arg Arg Ala Ala Lys Thr Ile Asn Phe Gly Val Leu Tyr Gly
            660             665             670

Met Ser Ala His Arg Leu Ser Gln Glu Leu Ala Ile Pro Tyr Glu Glu
            675             680             685

Ala Gln Ala Phe Ile Glu Arg Tyr Phe Gln Ser Phe Pro Lys Val Arg
            690             695             700
```

```
Ala Trp Ile Glu Lys Thr Leu Glu Glu Gly Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
        740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830
```

<210> SEQ ID NO 15
<211> LENGTH: 832
<212> TYPE: PRT
<213> ORGANISM: Artificial Sequence
<220> FEATURE:
<223> OTHER INFORMATION: Synthetic: E295F

<400> SEQUENCE: 15

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240
```

```
Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
        260                 265                 270

Leu Glu Arg Leu Glu Phe Gly Ser Leu Leu His Glu Phe Gly Leu Leu
    275                 280                 285

Glu Ser Pro Lys Ala Leu Phe Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
        340                 345                 350

Ala Lys Asp Leu Ser Val Leu Ala Leu Arg Glu Gly Leu Gly Leu Pro
    355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
```

```
                    660               665               670
Met Ser Ala His Arg Leu Ser Gln Glu Leu Ala Ile Pro Tyr Glu Glu
            675               680               685

Ala Gln Ala Phe Ile Glu Arg Tyr Phe Gln Ser Phe Pro Lys Val Arg
    690               695               700

Ala Trp Ile Glu Lys Thr Leu Glu Glu Gly Arg Arg Gly Tyr Val
705             710              715              720

Glu Thr Leu Phe Gly Arg Arg Tyr Val Pro Asp Leu Glu Ala Arg
                725              730              735

Val Lys Ser Val Arg Glu Ala Ala Glu Arg Met Ala Phe Asn Met Pro
            740              745              750

Val Gln Gly Thr Ala Ala Asp Leu Met Lys Leu Ala Met Val Lys Leu
            755              760              765

Phe Pro Arg Leu Glu Glu Met Gly Ala Arg Met Leu Leu Gln Val His
    770              775              780

Asp Glu Leu Val Leu Glu Ala Pro Lys Glu Arg Ala Glu Ala Val Ala
785             790              795              800

Arg Leu Ala Lys Glu Val Met Glu Gly Val Tyr Pro Leu Ala Val Pro
                805              810              815

Leu Glu Val Glu Val Gly Ile Gly Glu Asp Trp Leu Ser Ala Lys Glu
            820              825              830

<210> SEQ ID NO 16
<211> LENGTH: 832
<212> TYPE: PRT
<213> ORGANISM: Artificial Sequence
<220> FEATURE:
<223> OTHER INFORMATION: Synthetic: E295N

<400> SEQUENCE: 16

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
```

```
            195                 200                 205
Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Asn Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
    610                 615                 620
```

```
Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
        660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 17
<211> LENGTH: 832
<212> TYPE: PRT
<213> ORGANISM: Artificial Sequence
<220> FEATURE:
<223> OTHER INFORMATION: Synthetic: G418C

<400> SEQUENCE: 17

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160
```

```
Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Cys Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575
```

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 18
<211> LENGTH: 832
<212> TYPE: PRT
<213> ORGANISM: Artificial Sequence
<220> FEATURE:
<223> OTHER INFORMATION: Synthetic: L490Q

<400> SEQUENCE: 18

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

-continued

```
Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
```

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 19
<211> LENGTH: 832
<212> TYPE: PRT
<213> ORGANISM: Artificial Sequence
<220> FEATURE:
<223> OTHER INFORMATION: Synthetic: A502S

<400> SEQUENCE: 19

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly

```
                65                  70                  75                  80
Tyr Lys Ala Gly Arg Ala Pro Thr Pro Glu Asp Phe Pro Arg Gln Leu
                    85                  90                  95
Ala Leu Ile Lys Glu Leu Val Asp Leu Leu Gly Leu Ala Arg Leu Glu
                    100                 105                 110
Val Pro Gly Tyr Glu Ala Asp Val Leu Ala Ser Leu Ala Lys Lys
                    115                 120                 125
Ala Glu Lys Glu Gly Tyr Glu Val Arg Ile Leu Thr Ala Asp Lys Asp
            130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                    165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
                    195                 200                 205
Glu Glu Trp Gly Ser Leu Glu Ala Leu Leu Lys Asn Leu Asp Arg Leu
            210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                    245                 250                 255
Asp Phe Ala Lys Arg Arg Glu Pro Asp Arg Glu Arg Leu Arg Ala Phe
                    260                 265                 270
Leu Glu Arg Leu Glu Phe Gly Ser Leu Leu His Glu Phe Gly Leu Leu
            275                 280                 285
Glu Ser Pro Lys Ala Leu Glu Glu Ala Pro Trp Pro Pro Pro Glu Gly
            290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                    325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
        370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                    405                 410                 415
Trp Gly Arg Leu Glu Gly Glu Glu Arg Leu Leu Trp Leu Tyr Arg Glu
                    420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
        450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                    485                 490                 495
```

```
Glu Leu Gly Leu Pro Ser Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 20
<211> LENGTH: 832
<212> TYPE: PRT
<213> ORGANISM: Artificial Sequence
<220> FEATURE:
<223> OTHER INFORMATION: Synthetic: S543V

<400> SEQUENCE: 20

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30
```

```
Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
                115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
                195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
    275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
    355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445
```

```
Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Val Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 21
<211> LENGTH: 832
<212> TYPE: PRT
<213> ORGANISM: Artificial Sequence
<220> FEATURE:
<223> OTHER INFORMATION: Synthetic: D578E
```

<400> SEQUENCE: 21

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
```

```
                    405                 410                 415
Trp Gly Arg Leu Glu Gly Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
                515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Glu Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
                610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
                675                 680                 685

Ala Gln Ala Phe Ile Glu Arg Tyr Phe Gln Ser Phe Pro Lys Val Arg
                690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
                755                 760                 765

Phe Pro Arg Leu Glu Glu Met Gly Ala Arg Met Leu Leu Gln Val His
                770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830
```

<210> SEQ ID NO 22
<211> LENGTH: 832
<212> TYPE: PRT
<213> ORGANISM: Artificial Sequence
<220> FEATURE:
<223> OTHER INFORMATION: Synthetic: R593G

<400> SEQUENCE: 22

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365
```

```
Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
    580                 585                 590

Gly Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
    675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
    770                 775                 780
```

```
Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
        820                 825                 830

<210> SEQ ID NO 23
<211> LENGTH: 832
<212> TYPE: PRT
<213> ORGANISM: Artificial Sequence
<220> FEATURE:
<223> OTHER INFORMATION: Synthetic: L678F

<400> SEQUENCE: 23

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
            85                  90                  95

Ala Leu Ile Lys Glu Leu Val Asp Leu Leu Gly Leu Ala Arg Leu Glu
        100                 105                 110

Val Pro Gly Tyr Glu Ala Asp Asp Val Leu Ala Ser Leu Ala Lys Lys
    115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
            165                 170                 175

Asp Gln Trp Ala Asp Tyr Arg Ala Leu Thr Gly Asp Glu Ser Asp Asn
        180                 185                 190

Leu Pro Gly Val Lys Gly Ile Gly Glu Lys Thr Ala Arg Lys Leu Leu
    195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
        260                 265                 270

Leu Glu Arg Leu Glu Phe Gly Ser Leu Leu His Glu Phe Gly Leu Leu
    275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320
```

```
Leu Leu Ala Leu Ala Ala Arg Gly Gly Arg Val His Arg Ala Pro
            325                 330                 335
Glu Pro Tyr Lys Ala Leu Arg Asp Leu Lys Glu Ala Arg Gly Leu Leu
        340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
370                 375                 380
Thr Thr Pro Glu Gly Val Ala Arg Arg Tyr Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Arg Leu Leu Trp Leu Tyr Arg Glu
                420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
        450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
        530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
        595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Phe Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
        690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
```

```
                        740                 745                 750
Val Gln Gly Thr Ala Ala Asp Leu Met Lys Leu Ala Met Val Lys Leu
                755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 24
<211> LENGTH: 832
<212> TYPE: PRT
<213> ORGANISM: Artificial Sequence
<220> FEATURE:
<223> OTHER INFORMATION: Synthetic: L678T

<400> SEQUENCE: 24

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
```

-continued

```
                275                 280                 285
Glu Ser Pro Lys Ala Leu Glu Ala Pro Trp Pro Pro Glu Gly
    290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
            420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
    450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
    530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
            595                 600                 605
Leu Asp Tyr Ser Gln Ile Glu Leu Arg Val Leu Ala His Leu Ser Gly
    610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Thr Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
    690                 695                 700
```

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
            725                 730                 735

Val Lys Ser Val Arg Glu Ala Ala Glu Arg Met Ala Phe Asn Met Pro
        740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 25
<211> LENGTH: 832
<212> TYPE: PRT
<213> ORGANISM: Artificial Sequence
<220> FEATURE:
<223> OTHER INFORMATION: Synthetic: S699W

<400> SEQUENCE: 25

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

```
Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Ala Pro Trp Pro Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655
```

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Trp Phe Pro Lys Val Arg
    690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 26
<211> LENGTH: 832
<212> TYPE: PRT
<213> ORGANISM: Artificial Sequence
<220> FEATURE:
<223> OTHER INFORMATION: Synthetic: E713W

<400> SEQUENCE: 26

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

```
Leu Pro Gly Val Lys Gly Ile Gly Glu Lys Thr Ala Arg Lys Leu Leu
        195                 200                 205
Glu Glu Trp Gly Ser Leu Glu Ala Leu Leu Lys Asn Leu Asp Arg Leu
        210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
        275                 280                 285
Glu Ser Pro Lys Ala Leu Glu Glu Ala Pro Trp Pro Pro Glu Gly
        290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
        340                 345                 350
Ala Lys Asp Leu Ser Val Leu Ala Leu Arg Glu Gly Leu Gly Leu Pro
        355                 360                 365
Pro Gly Asp Asp Pro Met Leu Leu Ala Tyr Leu Leu Asp Pro Ser Asn
        370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
        435                 440                 445
Val Arg Leu Asp Val Ala Tyr Leu Arg Ala Leu Ser Leu Glu Val Ala
        450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
        515                 520                 525
Val Glu Lys Ile Leu Gln Tyr Arg Glu Leu Thr Lys Leu Lys Ser Thr
        530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
                580                 585                 590
Arg Ile Arg Arg Ala Phe Ile Ala Glu Glu Gly Trp Leu Leu Val Ala
        595                 600                 605
Leu Asp Tyr Ser Gln Ile Glu Leu Arg Val Leu Ala His Leu Ser Gly
```

-continued

```
            610                 615                 620
Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Trp Gly Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Glu Arg Met Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 27
<211> LENGTH: 832
<212> TYPE: PRT
<213> ORGANISM: Artificial Sequence
<220> FEATURE:
<223> OTHER INFORMATION: Synthetic: V737A

<400> SEQUENCE: 27

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
```

```
            145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
                195                 200                 205

Glu Glu Trp Gly Ser Leu Glu Ala Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575
```

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Val Ala
        595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Ala Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 28
<211> LENGTH: 832
<212> TYPE: PRT
<213> ORGANISM: Artificial Sequence
<220> FEATURE:
<223> OTHER INFORMATION: Synthetic: E745T

<400> SEQUENCE: 28

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

```
Val Pro Gly Tyr Glu Ala Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525
```

```
Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Thr Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 29
<211> LENGTH: 832
<212> TYPE: PRT
<213> ORGANISM: Artificial Sequence
<220> FEATURE:
<223> OTHER INFORMATION: Synthetic: L763F

<400> SEQUENCE: 29

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60
```

```
Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
```

485                 490                 495
Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Phe Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 30
<211> LENGTH: 832
<212> TYPE: PRT
<213> ORGANISM: Artificial Sequence
<220> FEATURE:
<223> OTHER INFORMATION: Synthetic: E790G

<400> SEQUENCE: 30

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly

```
                20              25              30
Leu Thr Thr Ser Arg Gly Glu Pro Val Gln Ala Val Tyr Gly Phe Ala
                35              40              45
Lys Ser Leu Leu Lys Ala Leu Lys Glu Asp Gly Asp Ala Val Ile Val
            50              55              60
Val Phe Asp Ala Lys Ala Pro Ser Phe Arg His Glu Ala Tyr Gly Gly
65              70              75              80
Tyr Lys Ala Gly Arg Ala Pro Thr Pro Glu Asp Phe Pro Arg Gln Leu
                85              90              95
Ala Leu Ile Lys Glu Leu Val Asp Leu Gly Leu Ala Arg Leu Glu
                100             105             110
Val Pro Gly Tyr Glu Ala Asp Val Leu Ala Ser Leu Ala Lys Lys
            115             120             125
Ala Glu Lys Glu Gly Tyr Glu Val Arg Ile Leu Thr Ala Asp Lys Asp
        130             135             140
Leu Tyr Gln Leu Leu Ser Asp Arg Ile His Val Leu His Pro Glu Gly
145             150             155             160
Tyr Leu Ile Thr Pro Ala Trp Leu Trp Glu Lys Tyr Gly Leu Arg Pro
                165             170             175
Asp Gln Trp Ala Asp Tyr Arg Ala Leu Thr Gly Asp Glu Ser Asp Asn
            180             185             190
Leu Pro Gly Val Lys Gly Ile Gly Glu Lys Thr Ala Arg Lys Leu Leu
            195             200             205
Glu Glu Trp Gly Ser Leu Glu Ala Leu Leu Lys Asn Leu Asp Arg Leu
        210             215             220
Lys Pro Ala Ile Arg Glu Lys Ile Leu Ala His Met Asp Asp Leu Lys
225             230             235             240
Leu Ser Trp Asp Leu Ala Lys Val Arg Thr Asp Leu Pro Leu Glu Val
                245             250             255
Asp Phe Ala Lys Arg Arg Glu Pro Asp Arg Glu Arg Leu Arg Ala Phe
            260             265             270
Leu Glu Arg Leu Glu Phe Gly Ser Leu Leu His Glu Phe Gly Leu Leu
        275             280             285
Glu Ser Pro Lys Ala Leu Glu Glu Ala Pro Trp Pro Pro Pro Glu Gly
        290             295             300
Ala Phe Val Gly Phe Val Leu Ser Arg Lys Glu Pro Met Trp Ala Asp
305             310             315             320
Leu Leu Ala Leu Ala Ala Ala Arg Gly Gly Arg Val His Arg Ala Pro
            325             330             335
Glu Pro Tyr Lys Ala Leu Arg Asp Leu Lys Glu Ala Arg Gly Leu Leu
            340             345             350
Ala Lys Asp Leu Ser Val Leu Ala Leu Arg Glu Gly Leu Gly Leu Pro
        355             360             365
Pro Gly Asp Asp Pro Met Leu Leu Ala Tyr Leu Leu Asp Pro Ser Asn
        370             375             380
Thr Thr Pro Glu Gly Val Ala Arg Arg Tyr Gly Gly Glu Trp Thr Glu
385             390             395             400
Glu Ala Gly Glu Arg Ala Ala Leu Ser Glu Arg Leu Phe Ala Asn Leu
                405             410             415
Trp Gly Arg Leu Glu Gly Glu Glu Arg Leu Leu Trp Leu Tyr Arg Glu
            420             425             430
Val Glu Arg Pro Leu Ser Ala Val Leu Ala His Met Glu Ala Thr Gly
            435             440             445
```

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Gly Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 31
<211> LENGTH: 832
<212> TYPE: PRT
<213> ORGANISM: Artificial Sequence
<220> FEATURE:

<223> OTHER INFORMATION: Synthetic: E794C

<400> SEQUENCE: 31

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400
```

```
Glu Ala Gly Glu Arg Ala Leu Ser Glu Arg Leu Phe Ala Asn Leu
                405                 410                 415
Trp Gly Arg Leu Glu Gly Glu Arg Leu Leu Trp Leu Tyr Arg Glu
            420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
    450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
        515                 520                 525
Val Glu Lys Ile Leu Gln Tyr Arg Glu Leu Thr Lys Leu Lys Ser Thr
    530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
    595                 600                 605
Leu Asp Tyr Ser Gln Ile Glu Leu Arg Val Leu Ala His Leu Ser Gly
610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
        675                 680                 685
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
        755                 760                 765
Phe Pro Arg Leu Glu Glu Met Gly Ala Arg Met Leu Leu Gln Val His
    770                 775                 780
Asp Glu Leu Val Leu Glu Ala Pro Lys Cys Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
```

-continued

```
           820             825             830
```

<210> SEQ ID NO 32
<211> LENGTH: 832
<212> TYPE: PRT
<213> ORGANISM: Artificial Sequence
<220> FEATURE:
<223> OTHER INFORMATION: Synthetic: E805I

<400> SEQUENCE: 32

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
```

```
                355                 360                 365
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
                450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
                515                 520                 525
Val Glu Lys Ile Leu Gln Tyr Arg Glu Leu Thr Lys Leu Lys Ser Thr
                530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
                580                 585                 590
Arg Ile Arg Arg Ala Phe Ile Ala Glu Glu Gly Trp Leu Leu Val Ala
                595                 600                 605
Leu Asp Tyr Ser Gln Ile Glu Leu Arg Val Leu Ala His Leu Ser Gly
                610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
                675                 680                 685
Ala Gln Ala Phe Ile Glu Arg Tyr Phe Gln Ser Phe Pro Lys Val Arg
                690                 695                 700
Ala Trp Ile Glu Lys Thr Leu Glu Glu Gly Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
                740                 745                 750
Val Gln Gly Thr Ala Ala Asp Leu Met Lys Leu Ala Met Val Lys Leu
                755                 760                 765
Phe Pro Arg Leu Glu Glu Met Gly Ala Arg Met Leu Leu Gln Val His
                770                 775                 780
```

```
Asp Glu Leu Val Leu Glu Ala Pro Lys Glu Arg Ala Glu Val Ala
785                 790                 795                 800

Arg Leu Ala Lys Ile Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830
```

<210> SEQ ID NO 33
<211> LENGTH: 832
<212> TYPE: PRT
<213> ORGANISM: Artificial Sequence
<220> FEATURE:
<223> OTHER INFORMATION: Synthetic: L828A

<400> SEQUENCE: 33

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320
```

```
Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735
```

-continued

```
Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Ala Ser Ala Lys Glu
            820                 825                 830
```

<210> SEQ ID NO 34
<211> LENGTH: 832
<212> TYPE: PRT
<213> ORGANISM: Artificial Sequence
<220> FEATURE:
<223> OTHER INFORMATION: Synthetic: (REF POLY) - (Taq-LR1) D732R

<400> SEQUENCE: 34

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270
```

-continued

Leu Glu Arg Leu Glu Phe Gly Ser Leu Leu His Glu Phe Gly Leu Leu
            275                 280                 285

Glu Ser Pro Lys Ala Leu Glu Ala Pro Trp Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
        420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
        500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
        580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
        660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg

```
            690                 695                 700
Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Arg Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
                755                 760                 765

Phe Pro Arg Leu Glu Glu Met Gly Ala Arg Met Leu Leu Gln Val His
                770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830
```

```
<210> SEQ ID NO 35
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 35

Asp Xaa Ser Xaa Xaa Glu
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(7)
<223> OTHER INFORMATION: Xaa can be any naturally occurring amino acid

<400> SEQUENCE: 36

Lys Xaa Xaa Xaa Xaa Xaa Xaa Tyr Gly
1               5

<210> SEQ ID NO 37
<211> LENGTH: 4
<212> TYPE: PRT
<213> ORGANISM: Artificial Sequence
<220> FEATURE:
<223> OTHER INFORMATION: Synthetic peptide

<400> SEQUENCE: 37

Val His Asp Glu
1

<210> SEQ ID NO 38
```

```
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 38

Asp Xaa Xaa Ser Leu Tyr Pro Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 39

Lys Xaa Xaa Xaa Asn Ser Xaa Tyr Gly
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide

<400> SEQUENCE: 40

Tyr Gly Asp Thr Asp Ser
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is Phe or Tyr

<400> SEQUENCE: 41

Asp Xaa Xaa Xaa Xaa Xaa
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa is Ser or Ala

<400> SEQUENCE: 42

Phe Xaa Gly Xaa Xaa Xaa Xaa
1               5

<210> SEQ ID NO 43
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 43

Tyr Xaa Asp Asp
1

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(8)
<223> OTHER INFORMATION: Xaa can be any naturally occurring amino acid

<400> SEQUENCE: 44

Gly Xaa Xaa Xaa Xaa Xaa Xaa Xaa Lys
1               5
```